United States Patent
Barr et al.

(10) Patent No.: US 9,556,168 B2
(45) Date of Patent: Jan. 31, 2017

(54) N-ALKYLATED INDOLE AND INDAZOLE COMPOUNDS AS RORGAMMAT INHIBITORS AND USES THEREOF

(71) Applicant: Merck Sharp & Dohme Corp., Rahway, NJ (US)

(72) Inventors: Kenneth J. Barr, Boston, MA (US); Corey E. Bienstock, Natick, MA (US); John K. Maclean, Brookline, MA (US); Hongjun Zhang, Newton, MA (US); Richard T. Beresis, Shanghai (CN); Neville J. Anthony, Northborough, MA (US); Blair T. Lapointe, Brookline, MA (US); Nunzio Sciammetta, Sudbury, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/421,052

(22) PCT Filed: Aug. 14, 2013

(86) PCT No.: PCT/US2013/054893
§ 371 (c)(1),
(2) Date: Feb. 11, 2015

(87) PCT Pub. No.: WO2014/028591
PCT Pub. Date: Feb. 20, 2014

(65) Prior Publication Data
US 2015/0210687 A1    Jul. 30, 2015

(30) Foreign Application Priority Data
Aug. 15, 2012 (CN) .................. PCT/CN2012/080134

(51) Int. Cl.
| | |
|---|---|
| A61K 31/00 | (2006.01) |
| C07D 471/04 | (2006.01) |
| C07D 231/56 | (2006.01) |
| A61K 31/416 | (2006.01) |
| A61K 31/437 | (2006.01) |
| C07D 403/06 | (2006.01) |

(52) U.S. Cl.
CPC ........... *C07D 471/04* (2013.01); *A61K 31/416* (2013.01); *A61K 31/437* (2013.01); *C07D 231/56* (2013.01); *C07D 403/06* (2013.01)

(58) Field of Classification Search
None
See application file for complete search history.

(56) References Cited

U.S. PATENT DOCUMENTS

| | | | |
|---|---|---|---|
| 4,670,447 A | 6/1987 | Strupczewski | |
| 5,639,780 A * | 6/1997 | Lau et al. ..................... | 514/419 |
| 6,133,290 A | 10/2000 | Krushinski, Jr. et al. | |
| 7,355,042 B2 | 4/2008 | Edgar et al. | |
| 7,514,465 B2 * | 4/2009 | Kuo et al. ..................... | 514/406 |
| 7,696,229 B2 | 4/2010 | Dunn et al. | |
| 7,772,252 B2 | 8/2010 | Hendrix et al. | |
| 9,095,583 B2 | 8/2015 | Karstens et al. | |
| 9,273,070 B2 | 3/2016 | Knochel et al. | |
| 2006/0030612 A1 | 2/2006 | Steffan et al. | |
| 2006/0100218 A1 | 5/2006 | Ibrahim et al. | |
| 2009/0124616 A1 | 5/2009 | Song et al. | |
| 2009/0233955 A1 | 9/2009 | Frazee et al. | |
| 2010/0317863 A1 | 12/2010 | Kuzmich et al. | |
| 2011/0150864 A1 | 6/2011 | Bignan et al. | |
| 2011/0263046 A1 | 10/2011 | Deuschle et al. | |
| 2015/0191434 A1 | 7/2015 | Barr et al. | |
| 2015/0218096 A1 | 8/2015 | Barr et al. | |
| 2015/0218169 A1 | 8/2015 | Barr et al. | |
| 2015/0297566 A1 | 10/2015 | Karstens et al. | |

FOREIGN PATENT DOCUMENTS

| | | |
|---|---|---|
| EP | 0429257 A2 | 5/1991 |
| EP | 2181710 A1 | 5/2010 |
| EP | 2487159 A1 | 8/2012 |
| JP | 2007238463 A | 9/2007 |

(Continued)

OTHER PUBLICATIONS

Lee, F.-Y. et al., J. Med. Chem. 2001 vol. 44 pp. 3746-3749.*
Annunziato et al., "Type 17 T helper cells—origins, features and possible roles in rheumatic disease," 5 *Nat. Rev. Rheumatol.* 325-31 (2009).
Boaventura et al., "Human mucosal leishmaniasis: Neutrophils infiltrate areas of tissue damage that express high levels of Th17-related cytokines," 40 *Eur. J. Immunol.* 2830-36 (2010).
Bundgaard (ed.), *Design of Prodrugs*, Elsevier (1985).

(Continued)

*Primary Examiner* — Heidi Reese
(74) *Attorney, Agent, or Firm* — Goodwin Procter LLP

(57) ABSTRACT

The present invention relates to compounds according to Formula I and pharmaceutically acceptable salts or solvates thereof. Such compounds can be used in the treatment of RORgammaT-mediated diseases or conditions.

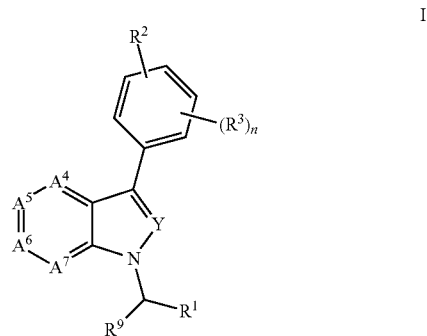

23 Claims, No Drawings

(56) References Cited

FOREIGN PATENT DOCUMENTS

| WO | WO-96/37467 A1 | 11/1996 |
|---|---|---|
| WO | WO-2006/063167 A1 | 6/2006 |
| WO | WO-2007/144327 A2 | 12/2007 |
| WO | WO-2008/132434 A2 | 11/2008 |
| WO | WO-2008/138889 A2 | 11/2008 |
| WO | WO-2008/153858 A1 | 12/2008 |
| WO | WO-2009/015067 A2 | 1/2009 |
| WO | WO-2010/050837 A1 | 5/2010 |
| WO | WO-2010/068483 A2 | 6/2010 |
| WO | WO-2010/150837 A1 | 12/2010 |
| WO | WO-2011/014775 A1 | 2/2011 |
| WO | WO-2011/103189 A1 | 8/2011 |
| WO | WO-2011/146313 A1 | 11/2011 |
| WO | WO-2012/064744 A2 | 5/2012 |
| WO | WO-2012/106995 A1 | 8/2012 |
| WO | WO-2012/176763 A1 | 12/2012 |

OTHER PUBLICATIONS

Buonocore et al., "Innate lymphoid cells drive interleukin-23-dependent innate intestinal pathology," 464 *Nature* 1371-75 (2010).
Eberl et al., "An essential function for the nuclear receptor RORγt in the generation of fetal lymphoid tissue inducer cells," 5(1) *Nat. Immunol.* 64-73 (2004).
Figueroa-Vega et al., "Increased Circulating Pro-Inflammatory Cytokines and Th17 Lymphocytes in Hashimoto's Thyroiditis," 95(2) *J. Clin. Endocrinol. Metab.* 953-62 (2010).
Gennaro (ed.), *Remington: The Science and Practice of Pharmacy*, 20th edition (2000).
He et al., "RORγt, a Novel Isoform of an Orphan Receptor, Negatively Regulates Fas Ligand Expression and IL-2 Production in T Cells," 9 Immunity 797-806 (1998).
Higuchi et al. (eds.), *Pro drugs as Novel Delivery Systems*, 14 A.C.S. Symposium Series (1975).
Hirose et al., "RORγ: the third member of ROR/RZR orphan receptor subfamily that is highly expressed in skeletal muscle," 205 Biochem. Biophys. Res. Comm. 1976-83 (1994).
Hueber et al., "Cutting Edge: Mast Cells Express IL-17A in Rheumatoid Arthritis Synovium," 184 *J. Immunol.* 3336-40 (2010).
Ivanov et al., "The Orphan Nuclear Receptor RORγt Directs the Differentiation Program of Proinflammatory IL-17+ T Helper Cells," 126 *Cell* 1121-33 (2006).
Jia et al., "The T helper type 17/regulatory T cell imbalance in patients with acute Kawasaki disease," 162 *Clin. Exp. Immunol.* 131-37 (2010).
Jin et al., "Structural Basis for Hydroxycholesterols as Natural Ligands of Orphan Nuclear Receptor RORγ," 24(5) *Mol. Endocrinol.* 923-29 (2010).
Kastelein et al., "Discovery and Biology of IL-23 and IL-27: Related but Functionally Distinct Regulators of Inflammation," 25 *Annu. Rev. Immunol.* 221-42 (2007).
Kurebayashi et aL, "Selective LXXLL peptides antagonize transcriptional activation by the retinoid-related orphan receptor RORγ," 315 *Biochem. Biophys. Res. Comm.* 919-27 (2004).
Louten et al., "Development and function of TH17 cells in health and disease," 123(5) *J. Allergy Clin. Immunol.* 1004-11 (2009).
Miossec et al., "Interleukin-17 and Type 17 Helper T Cells," 361(9) *New Eng. J. Med.* 888-98 (2009.
Roche (ed.), *Bioreversible Carriers in Drug Design*, Pergamon Press (1987).
Sun et al.,"Requirement for RORγin Thymocyte Survival and Lymphoid Organ Development," 288 *Science* 2369-72 (2000).
Sutton et al., "Interleukin-1 and IL-23 Induce Innate IL-17 Production from γδ T Cells, Amplifying Th17 Responses and Autoimmunity," 31 *Immunity* 331-41 (2009).
Varnavas et al., "Anthranilic acid based CCK$_1$ receptor antagonists: preliminary investigation on their second 'touch point,'" 40(6) Euro. J. Med. Chem. 563-81 (2005).

Wang et al., "Identification of SR1078, a Synthetic Agonist for the Orphan Nuclear Receptors RORα and RORγ," 5(11) ACS Chem. Biol. 1029-34 (2010).
Wang et al., "Modulation of Retinoic Acid Receptor-related Orphan Receptor α and γ Activity by 7-Oxygenated Sterol Ligands," 285(7) J. Bio. Chem. 5013-25 (2010).
Xie et al., "RORγt Recruits Steroid Receptor Coactivators to Ensure Thymocyte Survival," 175(6) *J. Immunol.* 3800-09 (2005).
Yang et al., "T Helper 17 Lineage Differentiation is Programmed by Orphan Nuclear Receptors RORα and RORγ," 28 *Immunity* 29-39 (2008).
Zhou et al., "Use of Homogeneous Time-Resolved Fluorescence Energy Transfer in the Measurement of Nuclear Receptor Activation," 25 *Methods* 54-61 (2001).
PCT International Search Report (PCT Article 18 and Rules 43 and 44) for PCT/US2013/054893, Feb. 24, 2014.
PCT Written Opinion of the International Searching Authority (PCT Rule 43*bis*.1) for PCT/US2013/054893, Feb. 24, 2014.
Chen, Hua-Sin et al., "Synthesis and antiplatelet activity of ethyl 4-(1-benzyl-1 *H* -indazol-3-yl)benzoate (YD-3) derivatives," *Bioorganic & Medicinal Chemistry*, vol. 16, pp. 1262-1278, (2008).
André et al., "Disruption of retinoid-related orphan receptor β changes circadian behaviour, causes retinal degeneration and leads to vacillans phenotype in mice," 17(14) The EMBO J. 3867-77 (1998).
Becker-André et al., "Identification of nuclear receptor mRNAs by RT-PCR amplification of conserved zinc-finger motif sequences," 194(3) Biochem. Biophys. Res. Comm. 1371-79 (1993).
Bernhardt et al., "Preparation of Solid Salt-Stabilized Functionalized Organozinc Compounds and their Application to Cross-Coupling and Carbonyl Addition Reactions," 50(39) Angew. Chem. Int. Ed. 9205-9209 (2011).
Boltze et al., "Chemische Struktur and antiphlogistische Wirkung in der Reihe der substituierten Indol-3-essigsauren," 30(8A) Arzneimittel-Forschung 1314-25 (1980).
Burris et al., "Targeting Orphan Nuclear Receptors for Treatment of Metabolic Diseases and Autoimmunity," 19(1) Chem. Biol. 51-59 (2012).
Cai, et al., "Pivotal Role of Dermal IL-17-Producing γδ T Cells in Skin Inflammation", Immunity (2011) vol. 35, pp. 596-610.
Carlberg et al., "RZRs, a new family of retinoid-related orphan receptors that function as both monomers and homodimers," 8 Mol. Endocrinol. 757-70 (1994).
D. van der Heijde, et al., "Secukinumab Provides Significant and Sustained Inhibition of Joint Structural Damage in a Phase III Study of Active Psoriatic Arthritis" Arthritis & Rheumatology Brief Report, Accepted Article DOI: 10/1002/art, American College of Rheumatology, (2016) pp. 1-27.
Dr. Baeton, et al., "Secukinumab, an Interleukin-17A Inhibitor, in Ankylosing Spondylitis", The New England Journal of Medicine, (2015) vol. 373, pp. 2534-2548.
Dussault et al., "Orphan nuclear receptor RORα-deficient mice display the cerebellar defects of staggerer," 70 Mech. Develop. 147-53 (1998).
El-Sawy et al., "Synthesis, antimicrobial and anti-cancer activities of some new N-ethyl, N-benzyl and N-benzoyl-3-indolyl heterocycles," 62 Acta Pharm. 157-179 (2012).
Extended European Search Report, EP Application No. 12744370.3, Sep. 9, 2014.
Giguère et al., "Isoform-specific amino-terminal domains dictate DNA-binding properties of RORα, a novel family of orphan hormone nuclear receptors," 8 Genes & Develop. 538-53 (1994).
Guo et al., "Stereospecific microbial reduction of ethyl 1-benzyl-3-oxo-piperidine-4-carboxylate," 17(13) Tetrahedron: Asymmetry 2015-2020 (2006).
Hirose et al., "Benzoheterocyclic derivatives. XI. Synthesis and pharmacological actions of indoline derivatives. 2," CA76:46035 (1971).
Huh et al., "Small molecule inhibitors of RORγt: Targeting Th17 cells and other applications," 42 Eur. J. Immunol. 2232-2237 (2012).

(56) References Cited

OTHER PUBLICATIONS

Inamoto et al., "Palladium-Catalyzed C—H Activation/Intramolecular Amination Reaction: A New Route to 3-Aryl/Alkylindazoles," 9(15) Org. Letts. 2931-34 (2007).

Julia et al., "Research in the indole series. IX. Certain 3-indolylsuccinic acids and the corresponding succinimides and pyrrolidines," CA61:92261 (1964).

Krueger, "A welcome surprise in psoriasis", Nature Medicine, (2012) vol. 18, No. 12, pp. 1750-1751.

Larhed et al., "Rapid Microwave-Assisted Suzuki Coupling on Solid-Phase," 37(45) Tetrahedron Letters 8219-22 (1996).

Leonardi, et al., "Anti-Interleukin-17 Monoclonal Antibody Ixekizumab in Chronic Plaque Psoriasis", The New England Journal of Medicine, (2012) vol. 366, Iss. 13, pp. 1-10.

Martinez, "Th17-biased RORγt transgenic mice become susceptible to a viral model for multiple sclerosis", Brain, Behavior, and Immunity, (2014) vol. 43, pp. 86-97.

Medvedev et al., "Cloning of a cDNA encoding the murine orphan receptor RZR/RORγ and characterization of its response element," 181 Gene 199-206 (1996).

Nakajima, et al., "IL-17A as an Inducer for Th2 Immune Responses in Murine Atopic Dermatitis Models", Journal of Investigative Dermatology, (2014) vol. 134, pp. 2122-2130.

Ortiz et al., "TOR: a new orphan receptor expressed in the thymus that can modulate retinoid and thyroid hormone signals," 9 Mol. Endocrinol. 1679-91 (1995).

Papp, et al. "Brodalumab, an Anti-Interleukin-17-Receptor Antibody for Psoriasis", The New England Journal of Medicine, (2012) vol. 366, Iss. 13, 9 pgs.

Reckenbeil et al., "Supramolekulare Phosphorylierung kationischer Alkohole mit 3-Arylindol-4-carboxamidin-Struktur," Liebigs Ann. Chem. 1219-29 (1994).

Skepner, et al., "Pharmacologic Inhibition of RORγt Regulates Th17 Signature Gene Expression and Suppresses Cutaneous Inflammation in Vivo", The Journal of Immunology, (2014) pp. 1-12.

Smith, "The Bench-to-Bedside Story of IL-17 and the Therapeutic Efficacy of its Targeting in Spondyloarthritis", Curr Rheumatol Rep. (2016) vol. 18, pp. 1-10.

Solt et al., "Action of RORs and their ligands in (patho)physiology," 23(12) Trends in Endocrinology and Metabolism. 619-627 (2012).

Tlustochowicz, et al. "Efficacy and Safety of Subcutaneous and Intravenous Loading Dose Regimens of Secukinumab in Patients with Active Rheumatoid Arthritis: Results from a Randomized Phase II Study" The Journal of Rheumatology, (2016) vol. 43, No. 3, pp. 495-503.

Villey et al., "RORγT, a thymus-specific isoform of the orphan nuclear receptor RORγ/TOR, is up-regulated by signaling through the pre-T cell receptor and binds to the TEA promoter," 29 Eur. J. Immunol. 4072-80 (1999).

Whelligan et al., "Aminopyrazine Inhibitors Binding to an Unusual Inactive Conformation of the Mitotic Kinase Nek2: SAR and Structural Characterization," 53 J. Med. Chem. 7682-98 (2010).

Wiesenberg et al., "Transcriptional activation of the nuclear receptor RZRα by the pineal gland hormone melatonin and identification of CGP 52608 as a synthetic ligand," 23(3) Nucl. Acids Res. 327-33 (1995).

Xiao, et al., "Small-Molecule RORγt Antagonists Inhibit T Helper 17 Cell Transcriptional Network by Divergent Mechanisms", Immunity (2014) vol. 40, pp. 477-489.

International Search Report and Written Opinion for PCT/US2013/054887, mailed Mar. 18, 2014 (5 pages).

International Search Report and Written Opinion for PCT/US2013/054902, mailed Feb. 28, 2014 (5 pages).

International Search Report and Written Opinion for PCT/US2013/054911 dated Mar. 4, 2014 (9 pages).

International Search Report from PCT/CN2012/071017, mailed May 24, 2012.

Cheng et al., "Design and synthesis of heterocyclic malonyl-CoA decarboxylase inhibitors," 16 Bioorg. Med. Chem. Lett. 695-700 (2006).

Ciattini et al., "An Efficient Synthesis of 3-Substituted Indoles by Palladium-Catalyzed Coupling Reaction of 3-Tributylstannylindoles with Organic Triflates and Halides," 35(15) Tetrahedron Letters 2405-08 (1994).

\* cited by examiner

```
                     SEQUENCE LISTING

<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: SRC1_2 peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 1

Leu Xaa Xaa Leu Leu
1               5
```

```
<210> SEQ ID NO 2
<211> LENGTH: 25
<212> TYPE: PRT
<213> ORGANISM: Artificial Sequence
<220> FEATURE:
<223> OTHER INFORMATION: SRC1_2 peptide

<400> SEQUENCE: 2

Cys Pro Ser Ser His Ser Ser Leu Thr Glu Arg His Lys Ile Leu His
1               5                   10                  15

Arg Leu Leu Gln Glu Gly Ser Pro Ser
            20                  25
```

N-ALKYLATED INDOLE AND INDAZOLE COMPOUNDS AS RORGAMMAT INHIBITORS AND USES THEREOF

CROSS REFERENCE TO RELATED APPLICATIONS

This application is a national stage of International (PCT) Patent Application Ser. No. PCT/US2013/054893, filed Aug. 14, 2013, which claims the benefit of and priority to Patent Application Ser. No. PCT/CN2012/080134, filed August 15, 2012.

BACKGROUND OF THE INVENTION

Upon activation by antigen-presenting cells naïve T helper cells undergo clonal expansion and will ultimately differentiate in cytokine secreting effector T cells, such as Th1 and Th2 subtypes. A third and distinct effector subset has been identified, which plays a key role in providing immunity to bacteria and fungi at mucosal surfaces (Kastelein et al., Annu. Rev. Immunol. 25: 221-242, 2007). This effector T helper cell subset can be distinguished based on its ability to produce large quantities of IL-17/F, IL-21 and IL-22, and is named Th17 (Miossec et al., New Eng. J. Med. 2361: 888-898, 2009).

Different T helper subsets are characterized by the expression of lineage specific master transcription factors. Th1 and Th2 effector cells express Tbet and GATA3, respectively. A Thymocyte/T cell specific variant of Retinoic Acid Receptor-related Orphan Receptor (ROR), RORgammaT, is highly expressed in Th17 cells (He et al., Immunity 9: 797-806, 1998). RORgammaT belongs to the nuclear hormone receptor superfamily (Hirose et al., Biochem. Biophys. Res. Comm. 205: 1976-1983, 1994). RORgammaT is a truncated form of RORgamma, lacking the first N-terminal 21 amino acids and is, in contrast to RORgamma which is expressed in multiple tissues (heart, brain, kidney, lung, liver, and muscle), exclusively expressed in cells of the lymphoid lineage and embryonic lymphoid tissue inducers (Sun et al., Science 288: 2369-2372, 2000; Eberl et al., Nat Immunol. 5: 64-73, 2004).

Studies using heterozygous knock-in mice replacing the RORgammaT open reading frame with GFP (green fluorescent protein), revealed a constitutive expression of GFP in approximately 10% of the CD4+ T cells in the small intestinal lamina propria (LP), co-expressing the Th17 cytokines IL-17/F and IL-22 (Ivanov et al., Cell 126: 1121-1133, 2006). In mice deficient for RORgammaT, the number of Th17 cells was markedly decreased in the LP; and in vitro stimulation of CD4+ T cells under Th17 polarizing conditions resulted in a drastic decrease of IL-17 expression. These results were further substantiated via forced expression of RORgammaT in naïve CD4+ T cells, which resulted in an induction of IL-17/F and IL-22 (Ivanov et al., Cell 126: 1121-1133, 2006). The foregoing studies demonstrate the importance of RORgammaT in differentiation and stabilization of the Th17 lineage. In addition, a ROR family member, RORalpha, has been demonstrated to be involved in Th17 differentiation and stabilization (Yang et al., Immunity 28: 29-39, 2008).

Recently, RORgammaT was shown to play a crucial role in non-Th17 lymphoid cells. In these studies, RORgammaT was critically important in innate lymphoid cells expressing Thy1, SCA-1, and IL-23R proteins. Genetic disruption of RORgamma in a mouse colitis model dependent on these innate lymphoid cells prevented colitis development (Buonocore et al., Nature 464: 1371-1375, 2010). In addition, RORgammaT was shown to play a crucial role in other non-Th17 cells, such as mast cells (Hueber et al., J. Immunol. 184: 3336-3340, 2010). Finally, RORgammaT expression and secretion of Th17-type of cytokines was reported for Lymphoid Tissue Inducer cells, NK T-cells, NK cells (Eberl et al., Nat. Immunol. 5: 64-73, 2004) and gamma-delta T-cells (Sutton et al., Nat. Immunol. 31: 331-341, 2009; Louten et al., J. Allergy Clin. Immunol. 123: 1004-1011, 2009), suggesting an important function for RORgammaT in these subtypes of cells.

Based on the role of IL-17 producing cells (either Th17 or non-Th17 cells) RORgammaT has been identified as a key mediator in the pathogenesis of several diseases (Louten et al., J. Allergy Clin. Immunol. 123: 1004-1011, 2009; Annuziato et al., Nat. Rev. Rheumatol. 5: 325-331, 2009). This was confirmed using several disease models representative of autoimmune diseases. Genetic ablation of the RORgamma gene in mice prevented the development of experimental autoimmune diseases, such as experimental autoimmune encephalomyelitis (EAE) and colitis (Ivanov et al., Cell 126:1121-33, 2006; Buonocore et al., Nature 464: 1371-1375, 2010).

With RORgammaT being a critical mediator in Th17-cells and non-Th17 cells, antagonism of the transcriptional activity of RORgammaT is expected to have a beneficial effect on autoimmune diseases, such as but not limited to rheumatoid arthritis, psoriasis, multiple sclerosis, inflammatory bowel disease, Crohn's disease, and asthma (Annunziato et al., Nat. Rev. Immunol. 5: 325-331, 2009; Louten et al., J. Allergy Clin. Immunol. 123: 1004-1011, 2009). Antagonism of RORgammaT may also be beneficial in other diseases that are characterized by increased levels of Th17 cells and/or elevated levels of Th17 hallmark cytokines such as IL-17, IL-22 and IL-23. Examples of such diseases are Kawasaki Disease (Jia et al., Clin. Exp. Immunol. 162: 131-137, 2010) and Hashimoto's thyroiditis (Figueroa-Vega et al., J. Clin. Endocrinol. Metab. 95: 953-62, 2010). Another example includes infectious diseases, such as but not limited to mucosal leishmaniasis (Boaventura et al., Eur. J. Immunol. 40: 2830-2836, 2010). In each of the above examples the inhibition may be enhanced by simultaneous inhibition of RORalpha.

Compounds modulating RORgammaT have been reported. Examples of agonists include T0901317 and SR1078 (Wang et al., ACS Chem. Biol. 5:1029-1034, 2010). In addition, antagonists have been reported such as 7-oxygenated sterols (Wang et al., J. Biol. Chem. 285: 5013-5025, 2009) and compounds described in EP2181710 A1.

Numerous immune and inflammatory disorders continue to afflict millions of patients worldwide. Although significant advances have been made in treating these disorders, current therapies do not provide satisfactory results for all patients due to, for example, detrimental side effects or insufficient efficacy. One exemplary immune disorder in need of better therapy is psoriasis. Various therapeutics have been developed in an attempt to treat psoriasis. However, the traditional therapies for psoriasis often have toxic adverse effects. An exemplary inflammatory disorder in need of better treatment is rheumatoid arthritis. Numerous therapeutics have been developed in an attempt to treat this disorder. However, some patients develop resistance to current therapies.

Accordingly, a need exists for improved treatments for immune disorders and inflammatory disorders. The present invention addresses this need and provides other related advantages.

SUMMARY OF THE INVENTION

The present invention provides compounds that alter the interaction of coregulator proteins with RORgammaT and thereby antagonize RORgammaT-mediated transcriptional activity, their use for the treatment of RORgammaT-mediated diseases or conditions, in particular autoimmune diseases and inflammatory diseases, as well as pharmaceutical compositions comprising such compounds and pharmaceutical carriers.

DETAILED DESCRIPTION OF THE INVENTION

The present invention provides a compound according to Formula I

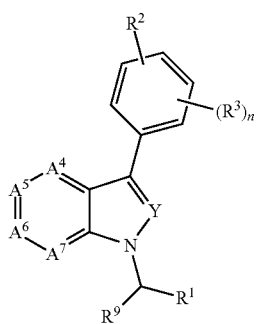

I or a pharmaceutically acceptable salt or solvate thereof, wherein:

Y is CH, N or $CR^a$;

n=0, 1, 2, 3 or 4;

$A^4$ is $CR^4$ or N, $A^5$ is $CR^5$ or N, $A^6$ is $CR^6$ or N, $A^7$ is $CR^7$ or N, with the proviso that no more than two of $A^4$-$A^7$ can be N;

$R^a$ is $(C_{1-4})$alkyl;

$R^1$ is
  (i) $(C_{3-12})$carbocyclyl; or
  (ii) a 4- to 12-membered heterocyclyl,
  both (i) and (ii) optionally substituted with one, two, three, four or five $R^8$;

$R^2$ is hydroxycarbonyl, hydroxycarbonyl$(C_{1-10})$alkyl, $(C_{1-10})$alkylsulfoxyaminocarbonyl, or carbamoyl;

$R^3$ is hydrogen, halogen, cyano, nitro, hydroxy, (C1-3)alkylC(O)O—, $(C_{1-4})$alkyl, or $(C_{1-4})$alkoxy, wherein $(C_{1-4})$alkyl and $(C_{1-4})$alkoxy are optionally substituted with one or more halogen;

$R^4$, $R^5$, $R^6$ and $R^7$ independently are H, halogen, amino, cyano, hydroxy, $(C_{1-3})$alkoxy, $(C_{1-4})$alkyl, $((C_{0-10})$alkyl)aminocarbonyl, $(di)(C_{1-6})$alkylaminocarbonyl or amino$(C_{1-4})$alkyl, wherein $(C_{1-3})$alkoxy, $(C_{1-4})$alkyl, $(C_{0-10})$alkyl)aminocarbonyl, $(di)(C_{1-6})$alkylaminocarbonyl and amino$(C_{1-4})$alkyl are optionally substituted with one or more halogen, hydroxyl or $(C_{1-3})$alkoxy; or a group having the formula

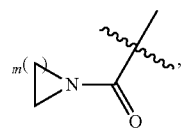

optionally substituted with one or more of the following: $(C_{1-10})$alkyl, halogen, amino, cyano, hydroxy, $(C_{1-3})$alkoxy, and wherein m is 1, 2, 3, or 4;

$R^8$ is halogen, cyano, amino, nitro, hydroxy, $H_2NC(O)$—, $(C_{1-3})$alkoxycarbonyl, $(di)(C_{1-6})$alkylaminocarbonyl, $(C_{1-4})$alkyl, $(C_{3-7})$cycloalkyl, $(C_{3-5})$heterocycloalkyl, $(C_{3-5})$ heteroaryl, or $(C_{1-3})$alkoxy, wherein $(C_{1-3})$alkoxycarbonyl, $(di)(C_{1-6})$alkylaminocarbonyl, $(C_{1-4})$alkyl, $(C_{3-7})$cycloalkyl, and $(C_{1-3})$alkoxy are optionally substituted with hydroxy or one, two or three halogens; and $R^9$ is hydrogen or $(C_{1-4})$alkyl.

In a first embodiment of the compound having Formula I is a compound having Formula Ia

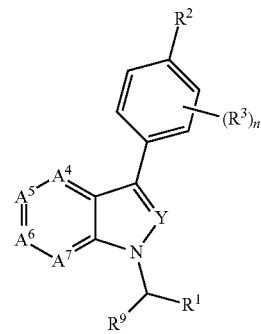

Ia and a pharmaceutically acceptable salt or solvate thereof.

In a second embodiment of the compound having Formula I is a compound having Formula Ib

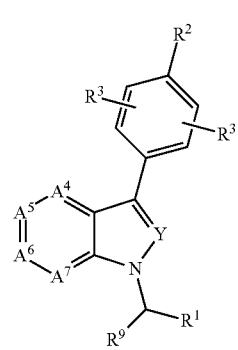

Ib and a pharmaceutically acceptable salt or solvate thereof.

In a first subset of the second embodiment is a compound wherein Y is N.

In a second subset of the second embodiment is a compound having Formula Ic

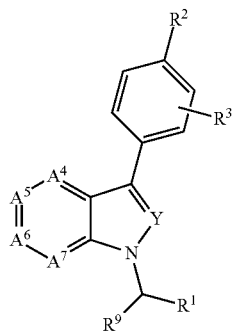

and a pharmaceutically acceptable salt or solvate thereof.

In a subset of the compound having Formula Ic, is a compound having Formula Id

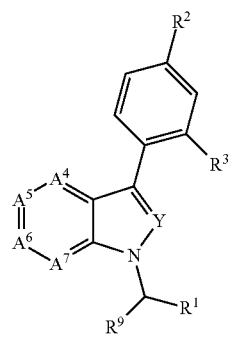

and a pharmaceutically acceptable salt or solvate thereof. In a further subset, Y is N.

In a first subset of the first embodiment is a compound having Formula Ie

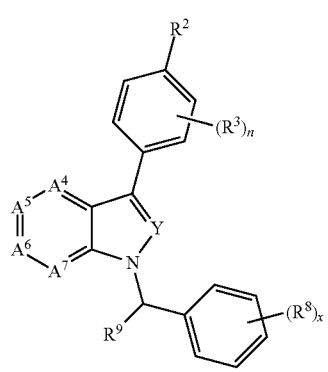

wherein x is 0, 1, 2, 3, 4 or 5;
and a pharmaceutically acceptable salt or solvate thereof.

In a subset of the compound having Formula Ie is a compound having Formula If

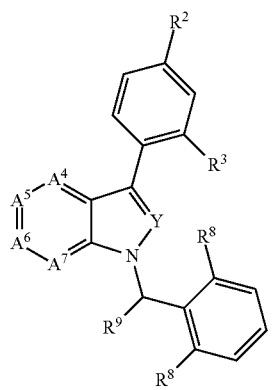

and a pharmaceutically acceptable salt or solvate thereof.

In a subset of the compound having Formula If is a compound having Formula Ig

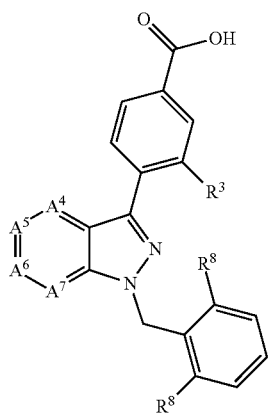

and a pharmaceutically acceptable salt or solvate thereof.

In a subset of the compound having Formula Ig is a compound having Formula Ih

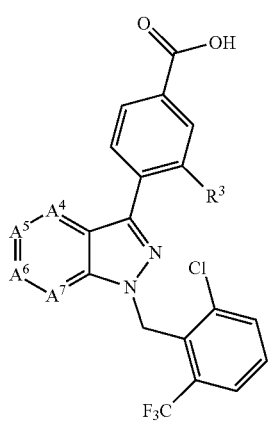

and a pharmaceutically acceptable salt or solvate thereof.

In a second subset of the first embodiment is a compound wherein $A^4$, $A^5$, $A^6$, $A^7$ are selected from the group consisting of: (i) $CR^4$, $CR^5$, $CR^6$, $CR^7$; (ii) N, $CR^5$, $CR^6$, $CR^7$; (iii)

$CR^4$, N, $CR^6$, $CR^7$; (iv) $CR^4$, $CR^5$, N, $CR^7$; (v) $CR^4$, $CR^5$, $CR^6$, N; (vi) N, N, $CR^6$, $CR^7$; (vii) $CR^4$, N, N, $CR^7$; (viii) $CR^4$, $CR^5$, N, N; (ix) N, $CR^5$, N, $CR^7$; (x) $CR^4$, N, $CR^6$, N; and (xi) N, $CR^5$, $CR^6$, N.

In a third subset of the first embodiment is a compound wherein $A^4$, $A^5$, $A^6$, $A^7$ are selected from the group consisting of: (i) $CR^4$, $CR^5$, $CR^6$, $CR^7$; (ii) N, $CR^5$, $CR^6$, $CR^7$; and (iii) $CR^4$, $CR^5$, N, $CR^7$.

In a fourth subset of the first embodiment is a compound wherein $A^4$, $A^5$, $A^6$, $A^7$ is (i) $CR^4$, $CR^5$, $CR^6$, $CR^7$, or (ii) N, $CR^5$, $CR^6$, $CR^7$; and Y is N.

In a fifth subset of the first embodiment is compound wherein $R^1$ is (i) $(C_{3-7})$cycloalkyl or $(C_{3-5})$heterocycloalkyl, both optionally substituted with one or more $R^8$, wherein $R^8$ is selected from halogen, amino, cyano, nitro, hydroxy, $H_2NC(O)$—, $(C_{1-3})$alkoxycarbonyl, $(di)(C_{1-6})$alkylaminocarbonyl, $(C_{1-4}$ alkyl or $(C_{1-3})$alkoxy, wherein $(C_{1-3})$alkoxycarbonyl, $(di)(C_{1-6})$alkylaminocarbonyl, $(C_{1-4}$ alkyl and $(C_{1-3})$alkoxy are optionally substituted with one or more halogens; (ii) $(C_{2-9})$heteroaryl, optionally substituted with one or more $R^8$, wherein $R^8$ is selected from halogen, amino, cyano, nitro, hydroxy, $H_2NC(O)$—, $(C_{1-3})$alkoxycarbonyl, $(di)(C_{1-6})$alkylaminocarbonyl, $(C_{1-4})$alkyl or $(C_{1-3})$alkoxy, wherein $(C_{1-3})$alkoxycarbonyl, $(di)(C_{1-6})$alkylaminocarbonyl, $(C_{1-4})$alkyl and $(C_{1-3})$alkoxy are optionally substituted with one or more halogens; or (iii) $(C_{6-14})$aryl, optionally substituted with one or more $R^8$, wherein $R^8$ is selected from halogen, amino, cyano, nitro, hydroxy, $H_2NC(O)$—, $(C_{1-3})$alkoxycarbonyl, $(di)(C_{1-6})$alkylaminocarbonyl, $(C_{1-4})$alkyl or $(C_{1-3})$alkoxy, wherein $(C_{1-3})$alkoxycarbonyl, $(di)(C_{1-6})$alkylaminocarbonyl, $(C_{1-4})$alkyl or $(C_{1-3})$alkoxy are optionally substituted with one or more halogens.

In a sixth subset of the first embodiment is compound wherein $R^1$ is $(C_{2-9})$heteroaryl, or (ii) $(C_{6-14})$aryl, optionally substituted with one, two, three, four or five $R^8$. In a further subset $R^8$ is selected from halogen, amino, cyano, nitro, hydroxy, $(C_{1-3})$alkoxycarbonyl, $(C_{1-4})$alkyl, $(C_{1-3})$alkoxy, wherein $(C_{1-3})$alkoxycarbonyl, $(C_{1-4})$alkyl and $(C_{1-3})$alkoxy are optionally substituted with one or more halogens.

In a seventh subset of the first embodiment, $R^1$ is $(C_{6-14})$aryl, optionally substituted with one, two, three, four or five $R^8$. In a further subset $R^8$ is selected from halogen, cyano, $(C_{1-3})$-alkoxycarbonyl, $(C_{1-4})$alkyl or $(C_{1-3})$alkoxy, wherein $(C_{1-3})$alkoxycarbonyl, $(C_{1-4})$alkyl and $(C_{1-3})$alkoxy are optionally substituted with one, two or three halogens.

In an eighth subset of the first embodiment, $R^1$ is phenyl, naphthyl, pyridinyl, quinolinyl, benzooxadiazolyl, thiophenyl, isoxazolyl, or benzothiophenyl, each optionally substituted with one or more $R^8$. In a further subset $R^8$ is selected from halogen, amino, cyano, nitro, hydroxy, $(C_{1-3})$alkoxycarbonyl, $(C_{1-4})$alkyl or $(C_{1-3})$alkoxy, wherein $(C_{1-3})$alkoxycarbonyl, $(C_{1-4})$alkyl and $(C_{1-3})$alkoxy are optionally substituted with one or more halogens.

In a ninth subset of the first embodiment, $R^1$ is phenyl, optionally substituted with one, two or three $R^8$. In a further subset $R^8$ is selected from halogen, amino, cyano, nitro, hydroxy, $(C_{1-3})$alkoxycarbonyl, $(C_{1-4})$alkyl or $(C_{1-3})$alkoxy, wherein $(C_{1-3})$alkoxycarbonyl, $(C_{1-4})$alkyl and $(C_{1-3})$alkoxy are optionally substituted with one or more halogens.

In a tenth subset of the first embodiment, $R^2$ is C(O)OH.

A still further embodiment of the compounds of Formula I, Ia, Ib, Ic, Id, Ie, If, Ig, and Ih are compounds wherein one of $R^4$, $R^5$, $R^6$, and $R^7$ is other than hydrogen.

The invention also relates to those compounds wherein all specific definitions for $A^1$ through $A^4$, $R^1$ through $R^9$, $R^a$, Y, m, n and x and all substituent groups in the various aspects of the inventions defined hereinabove occur in any combination within the definition of the compound of Formula I.

Non-limiting examples of the compound of the present invention include:

4-{1-[2-chloro-6-(trifluoromethyl)benzyl]-1H-pyrazolo[3,4-c]pyridin-3-yl}-3-fluorobenzoic acid;

4-[1-(2-bromo-6-fluorobenzyl)-1H-pyrazolo[4,3-b]pyridin-3-yl]-3-fluorobenzoic acid;

4-{1-[2-chloro-6-(trifluoromethyl)benzyl]-4-fluoro-1H-indazol-3-yl}-3-fluorobenzoic acid;

4-{1-[2-chloro-6-(trifluoromethyl)benzyl]-4-fluoro-1H-indazol-3-yl}benzoic acid;

4-{1-[2-chloro-6-(trifluoromethyl)benzyl]-4-fluoro-1H-indazol-3-yl}-2,5-difluorobenzoic acid;

4-(1-{1-[2-chloro-6-(trifluoromethyl)phenyl]ethyl}-4-fluoro-1H-indazol-3-yl)-3-fluorobenzoic acid;

4-(1-{(1R or 1S)-1-[2-chloro-6-(trifluoromethyl)phenyl]ethyl}-4-fluoro-1H-indazol-3-yl)-3-fluorobenzoic acid;

4-(1-{(1S or 1R)-1-[2-chloro-6-(trifluoromethyl)phenyl]ethyl}-4-fluoro-1H-indazol-3-yl)-3-fluorobenzoic acid;

4-[1-(2-bromo-3-fluorobenzyl)-1H-pyrazolo[4,3-b]pyridin-3-yl]-3-fluorobenzoic acid;

4-[1-(5-chloro-2-cyanobenzyl)-1H-pyrazolo[4,3-b]pyridin-3-yl]-3-fluorobenzoic acid;

3-fluoro-4-(1-{1-[2-(trifluoromethyl)phenyl]ethyl}-1H-pyrazolo[4,3-b]pyridin-3-yl)benzoic acid;

4-[1-(6-chloro-2-fluoro-3-methylbenzyl)-1H-pyrazolo[4,3-b]pyridin-3-yl]-3-fluorobenzoic acid;

4-[1-(2-chloro-3,6-difluorobenzyl)-1H-pyrazolo[4,3-b]pyridin-3-yl]-3-fluorobenzoic acid;

3-fluoro-4-[1-(2,3,6-trifluorobenzyl)-1H-pyrazolo[4,3-b]pyridin-3-yl]benzoic acid;

3-fluoro-4-{1-[2-fluoro-6-(trifluoromethyl)benzyl]-1H-pyrazolo[4,3-b]pyridin-3-yl}benzoic acid;

4-[1-(2,6-difluorobenzyl)-1H-pyrazolo[4,3-b]pyridin-3-yl]-3-fluorobenzoic acid;

4-[1-(2-chloro-6-fluorobenzyl)-1H-pyrazolo[4,3-b]pyridin-3-yl]-3-fluorobenzoic acid;

4-[1-(6-chloro-2-fluoro-3-methoxybenzyl)-1H-pyrazolo[4,3-b]pyridin-3-yl]-3-fluorobenzoic acid;

4-[1-(2-chloro-6-fluoro-3-methoxybenzyl)-1H-pyrazolo[4,3-b]pyridin-3-yl]-3-fluorobenzoic acid;

4-[1-(2,3-dichloro-6-fluorobenzyl)-1H-pyrazolo[4,3-b]pyridin-3-yl]-3-fluorobenzoic acid;

4-[1-(1-benzothiophen-7-ylmethyl)-1H-pyrazolo[4,3-b]pyridin-3-yl]-3-fluorobenzoic acid;

4-{1-[2,6-dichloro-3-(trifluoromethyl)benzyl]-1H-pyrazolo[4,3-b]pyridin-3-yl}-3-fluorobenzoic acid;

4-[1-(3,6-dichloro-2-fluorobenzyl)-1H-pyrazolo[4,3-b]pyridin-3-yl]-3-fluorobenzoic acid;

4-{1-[2-chloro-6-(methoxycarbonyl)benzyl]-1H-pyrazolo[4,3-b]pyridin-3-yl}-3-fluorobenzoic acid;

4-[1-(2-bromo-6-chlorobenzyl)-1H-pyrazolo[4,3-b]pyridin-3-yl]-3-fluorobenzoic acid;

4-{1-[2-chloro-6-(trifluoromethyl)benzyl]-1H-pyrazolo[4,3-b]pyridin-3-yl}-3-fluorobenzoic acid;

4-{1-[2-chloro-6-(trifluoromethyl)benzyl]-1H-pyrrolo[3,2-b]pyridin-3-yl}-3-fluorobenzoic acid;

4-{1-[2-chloro-6-(trifluoromethyl)benzyl]-1H-pyrrolo[2,3-c]pyridin-3-yl}-3-fluorobenzoic acid;

4-(1-(2-chloro-6-(trifluoromethyl)benzyl)-1H-indazol-3-yl)-2-hydroxybenzoic acid;

3-Fluoro-4-[4-fluoro-1-(2-fluoro-6-methoxybenzyl)-1H-indazol-3-yl]benzoic acid;

3-fluoro-4-(4-fluoro-1-(3-(trifluoromethoxy)benzyl)-1H-indazol-3-yl)benzoic acid;

3-fluoro-4-[4-fluoro-1-(2-methoxybenzyl)-1H-indazol-3-yl]
benzoic acid;
3-fluoro-4-{4-fluoro-1-[2-(1H-pyrazol-1-yl)benzyl]-1H-indazol-3-yl}benzoic acid;
4-[1-(2-cyanobenzyl)-4-fluoro-1H-indazol-3-yl]-3-fluorobenzoic acid;
3-fluoro-4-{4-fluoro-1-[2-fluoro-5-(trifluoromethoxy)benzyl]-1H-indazol-3-yl}benzoic acid;
4-[1-(2,6-dichlorobenzyl)-4-fluoro-1H-indazol-3-yl]-3-fluorobenzoic acid;
4-(1-(2,6-dichlorobenzyl)-1H-pyrazolo[4,3-b]pyridin-3-yl)-3-fluorobenzoic acid;
4-(1-(2-bromo-6-(trifluoromethyl)benzyl)-4-fluoro-1H-indazol-3-yl)-5-fluoro-2-hydroxybenzoic acid;
4-(1-(2-chloro-6-fluorobenzyl)-4-fluoro-1H-indazol-3-yl)-5-fluoro-2-hydroxybenzoic acid;
4-(1-benzyl-4-fluoro-1H-indazol-3-yl)-5-fluoro-2-hydroxybenzoic acid;
4-(1-(2-chloro-5-fluorobenzyl)-4-fluoro-1H-indazol-3-yl)-5-fluoro-2-hydroxybenzoic acid;
4-(1-(2-chloro-4-fluorobenzyl)-4-fluoro-1H-indazol-3-yl)-5-fluoro-2-hydroxybenzoic acid;
4-(1-(2-bromo-5-fluorobenzyl)-4-fluoro-1H-indazol-3-yl)-5-fluoro-2-hydroxybenzoic acid;
4-(1-(3-chloro-5-fluorobenzyl)-4-fluoro-1H-indazol-3-yl)-5-fluoro-2-hydroxybenzoic acid;
4-(1-(3,5-dichlorobenzyl)-4-fluoro-1H-indazol-3-yl)-5-fluoro-2-hydroxybenzoic acid;
4-(1-(4-bromo-2-fluorobenzyl)-4-fluoro-1H-indazol-3-yl)-5-fluoro-2-hydroxybenzoic acid;
4-(1-(2,5-dichlorobenzyl)-4-fluoro-1H-indazol-3-yl)-5-fluoro-2-hydroxybenzoic acid;
5-fluoro-4-(4-fluoro-1-(3-fluoro-5-(trifluoromethyl)benzyl)-1H-indazol-3-yl)-2-hydroxybenzoic acid;
5-fluoro-4-(4-fluoro-1-(2-fluoro-6-(trifluoromethyl)benzyl)-1H-indazol-3-yl)-2-hydroxybenzoic acid;
4-(1-(2-chloro-6-cyclopropylbenzyl)-4-fluoro-1H-indazol-3-yl)-5-fluoro-2-hydroxybenzoic acid;
4-(1-(2-chloro-6-methylbenzyl)-4-fluoro-1H-indazol-3-yl)-5-fluoro-2-hydroxybenzoic acid;
4-(1-(2-chloro-6-(1-hydroxycyclobutyl)benzyl)-4-fluoro-1H-indazol-3-yl)-3-fluorobenzoic acid;
5-fluoro-4-(4-fluoro-1-(2-methyl-6-(trifluoromethyl)benzyl)-1H-indazol-3-yl)-2-hydroxybenzoic acid;
5-fluoro-4-(4-fluoro-1-(2-(trifluoromethyl)benzyl)-1H-indazol-3-yl)-2-hydroxybenzoic acid;
4-(1-(2-ethyl-6-(trifluoromethyl)benzyl)-4-fluoro-1H-indazol-3-yl)-5-fluoro-2-hydroxybenzoic acid;
4-(1-(2-chloro-6-fluorobenzyl)-4-fluoro-1H-indazol-3-yl)-5-fluoro-2-hydroxybenzoic acid;
sodium 4-(1-(2-chloro-6-(trifluoromethyl)benzyl)-4-fluoro-6-(3-methoxyazetidine-1-carbonyl)-1H-indazol-3-yl)-5-fluoro-2-hydroxybenzoate;
4-(6-(azetidine-1-carbonyl)-1-(2-chloro-6-(trifluoromethyl)benzyl)-4-fluoro-1H-indazol-3-yl)-5-fluoro-2-hydroxybenzoic acid; and
4-(6-(azetidine-1-carbonyl)-1-(2-chloro-6-(trifluoromethyl)benzyl)-4-fluoro-1H-indazol-3-yl)-3-fluorobenzoic acid.

The terms used herein have their ordinary meaning and the meaning of such terms is independent at each occurrence thereof. That notwithstanding, and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "alkoxy", etc.

As used herein, and throughout this disclosure, the following terms, unless otherwise indicated, shall be understood to have the following meanings:

The term "alkyl," as used herein, refers to an aliphatic hydrocarbon group having one of its hydrogen atoms replaced with a bond having the specified number of carbon atoms. In different embodiments, an alkyl group contains, for example, from 1 to 6 carbon atoms ($C_1$-$C_6$ alkyl) or from 1 to 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

Unless specified otherwise, "alkyl" includes both branched- and straight-chain saturated aliphatic hydrocarbon groups, including all isomers, having the specified number of carbon atoms; for example, "$C_{1-6}$ alkyl" (or "$C_1$-$C_6$ alkyl") includes all of the hexyl alkyl and pentyl alkyl isomers as well as n-, iso-, sec- and t-butyl, n- and isopropyl, ethyl and methyl. "Alkylene" refers to both branched- and straight-chain saturated aliphatic hydrocarbon groups, including all isomers, having the specified number of carbons, and having two terminal end chain attachments; for example, the term "A-$C_4$alkylene-B" represents, for example, A-$CH_2$—$CH_2$—$CH_2$—$CH_2$—B, A-$CH_2$—$CH_2$—$CH(CH_3)$—$CH_2$—B, A-$CH_2$—$CH$($CH_2CH_3$)—B, A-$CH_2$—$C(CH_3)(CH_3)$—B, and the like. "Alkoxy" represents a linear or branched alkyl group of indicated number of carbon atoms attached through an oxygen bridge; for example "$C_1$-$C_6$ alkoxy" includes —$OCH_3$, —$OCH_2CH_3$, —$OCH(CH_3)_2$, —$O(CH_2)_5CH_3$, and the like.

Unless otherwise specifically noted as only "unsubstituted" or only "substituted", alkyl groups are unsubstituted or substituted with 1 to 3 substituents on each carbon atom, with halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, ($C_{3-7}$)cycloalkyl, ($C_{3-5}$)heterocycloalkyl, $C_2$-$C_6$ alkenyl, $C_2$-$C_6$ alkynyl, ($C_0$-$C_6$ alkyl) S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2N$—C(NH)—, $H_2N$—C(O)(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, —NH($C_1$-$C_6$ alkyl)NHC(O)NH($C_1$-$C_6$ alkyl), NHC(O)O$C_1$-$C_6$ alkyl, —NH($C_1$-$C_6$ alkyl)NHSO$_2$($C_1$-$C_6$ alkyl), —($C_0$-$C_6$ alkyl)NHSO$_2$($C_1$-$C_6$ alkyl), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "alkenyl" means a straight or branched carbon chain having the specified number of carbon atoms with at least one carbon-carbon double bond. Examples of alkenyl include, but are not limited to, vinyl, allyl, isopropenyl, pentenyl, hexenyl, heptenyl, 1-propenyl, 2-butenyl, 2-methyl-2-butenyl, 2,4-hexadienyl, and the like.

The term "alkynyl" means a straight or branched carbon chain having the specified number of carbon atoms with at least one carbon-carbon triple bond. Examples of alkynyl include, but are not limited to ethynyl, propargyl, 1-propynyl, 2-butynyl, and the like.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either attached via a bond to, or fused (including spirofused) to, the other ring, and each ring is saturated or unsaturated. The carbocycle may be attached to the rest of the molecule at any carbon atom that results in a stable compound.

Saturated carbocyclics form a subset of carbocycles in which the entire ring system (mono- or polycyclic) is saturated. Saturated monocyclic carbocyclic rings are also referred to as cycloalkyl rings, e.g., cyclopropyl, cyclobutyl, etc. The fused bicyclic carbocycles are a further subset of the carbocycles in which a $C_7$ to $C_{10}$ bicyclic ring system in which each ring is saturated or unsaturated and two adjacent carbon atoms (or in the case of spirofused, one carbon atom) are shared by each of the rings in the ring system. A saturated bicyclic carbocycle is one in which both rings are saturated. An unsaturated bicyclic carbocycle is one in which one ring is unsaturated and the other is unsaturated or saturated. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

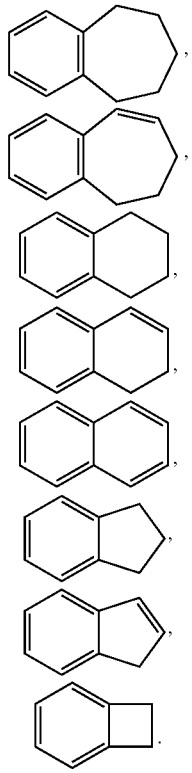

Aromatic carbocycles form another subset of the carbocycles. The term "aryl" refers to aromatic mono- and polycarbocyclic ring systems in which the individual carbocyclic rings in the polyring systems are fused or attached to each other via a single bond. Suitable aryl groups include phenyl, naphthyl, and biphenyl.

The term "cycloalkyl" means a cyclic ring of an alkane having the specified total ring carbon atoms; for example cyclopropyl, cyclobutyl, cyclopentyl, cyclohexyl.

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is either attached via a bond to, or fused (including spirofused) to, the other ring, and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system that consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, 1,4-dioxanyl, 1,4-thioxanyl, tetrahydropyranyl, tetrahydrofuryl (or tetrahydrofuranyl), tetrahydrothienyl, and tetrahydrothiopyranyl.

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic aromatic ring, and that consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of monocyclic heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isoxazolyl, oxadiazolyl, thiazolyl, isothiazolyl, and thiadiazolyl. Examples of bicyclic heteroaromatic rings include benzotriazolyl, indolyl, benzoxazolyl, benzofuranyl, benzothienyl, benzothiazolyl, benzimidazolyl, isoindolyl, indazolyl, quinoxalinyl, quinazolinyl, cinnolinyl, quinolinyl, isoquinolinyl, naphthyridinyl, pyrazolo[3,4-b]pyridine, imidazo[2,1-b](1,3)thiazole, (i.e.,

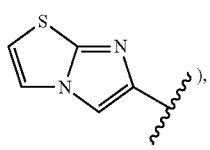 [SMILES: *c1cn2ccsc2n1]

6-(1-pyrrolyl)-3-pyridyl, 4-(1-pyrrolyl)phenyl, 4-(pyrid-3-yl)phenyl, 4-(pyrid-4-yl)phenyl, and benzothiophenyl (i.e.

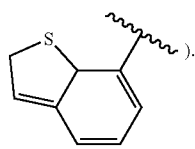 [SMILES: *C1=CC=CC2=CCSC12]

Another subset of heterocycles is unsaturated heterocycles in which one or both rings are unsaturated (provided the entire ring system is not aromatic). Representative examples of unsaturated heterocycles include dihydrofuranyl, dihydrothienyl, dihydropyranyl, dihydroimidazolyl, indolinyl, isoindolinyl, chromanyl, isochromanyl, tetrahydroquinolinyl, tetrahydroisoquinolinyl, tetrahydronaphthyridinyl, 2,3-dihydrobenzofuranyl, 1,4-benzoxazinyl, 1,3-benzoxazolinyl, 2,3-dihydrobenzo-1,4-dioxinyl (i.e.,

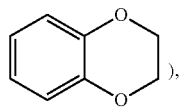

and benzo-1,3-dioxolyl (i.e.,

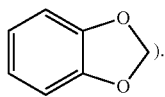

In certain contexts herein,

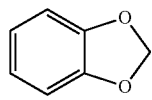

is alternatively referred to as phenyl having as a substituent methylenedioxy attached to two adjacent carbon atoms. Also included are groups such as chromone and coumarin.

Unless otherwise specifically noted as only unsubstituted or only substituted, cycloalkyl, cycloalkenyl, heterocycloalkyl, aryl (including phenyl) and heteroaryl groups are unsubstituted or substituted (also referred to as "optionally substituted"). Unless the substituents are specifically provided, substituents for substituted or optionally substituted cycloalkyl, heterocycloalkyl, cycloalkenyl, aryl (including phenyl, and as an isolated substituent or as part of a substituent such as in aryloxy and aralkyl), heteroaryl (as an isolated substituent or as part of a substituent such as in heteroaryloxy and heteroaralkyl) are one to three groups independently selected from halogen (or halo), $C_1$-$C_6$ alkyl optionally substituted with one to five fluorine, $NH_2$, $N(C_1$-$C_6$ alkyl)$_2$, $NO_2$, oxo, CN, $N_3$, —OH, —O($C_1$-$C_6$ alkyl) optionally substituted with one to five fluorine, $C_3$-$C_{10}$ cycloalkyl, ($C_{3-7}$)cycloalkyl, ($C_{3-5}$)heterocycloalkyl, $C_2$-$C_6$ alkenyl, $C_2$-$C_6$ alkynyl, ($C_0$-$C_6$ alkyl)S(O)$_{0-2}$—, aryl-S(O)$_{0-2}$—, ($C_0$-$C_6$ alkyl)S(O)$_{0-2}$($C_0$-$C_6$ alkylene)-, ($C_0$-$C_6$ alkyl)C(O)NH—, $H_2$N—C(NH)—, ($C_0$-$C_6$ alkyl)C(O)—, ($C_0$-$C_6$ alkyl)OC(O)—, ($C_0$-$C_6$alkyl)O($C_1$-$C_6$ alkylene)-, ($C_0$-$C_6$ alkyl)C(O)$_{1-2}$($C_0$-$C_6$ alkylene)-, ($C_0$-$C_6$ alkyl)$_2$NC(O)—, ($C_0$-$C_6$ alkyl)OC(O)NH—, aryl, aralkyl, heteroaryl, heteroaralkyl, halo-aryl, halo-aralkyl, halo-heteroaryl, halo-heteroaralkyl, cyano-aryl, cyano-aralkyl, cyano-heteroaryl and cyano-heteroaralkyl.

The term "halogen" (or "halo") refers to fluorine, chlorine, bromine and iodine (alternatively referred to as fluoro (F), chloro (Cl), bromo (Br), and iodo (I)).

The term "haloalkyl" means alkyl having the specified number of carbon atoms in which from one to all of the hydrogen atoms have been replaced by a halogen atom.

The terms "aralkyl" and "heteroaralkyl" refer to an aryl/heteroaryl linked to the rest of the molecule via a $C_1$ to $C_4$ alkylene.

The term "$C_0$" as employed in expressions such as "$C_{0-6}$ alkylene" means a direct covalent bond; or when employed in expressions such as "$C_{0-6}$ alkyl" means hydrogen. Similarly, when an integer defining the presence of a certain number of atoms in a group is equal to zero, it means that the atoms adjacent thereto are connected directly by a bond; for example, in the structure

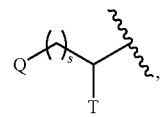

wherein s is an integer equal to zero, 1 or 2, the structure is

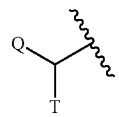

when s is zero; or it means that the indicated atom is absent; for example —S(O)$_0$— means —S—.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds. For variable definitions containing terms having repeated terms, e.g., (CRiRj)$_r$, where r is the integer 2, Ri is a defined variable, and Rj is a defined variable, the value of Ri may differ in each instance in which it occurs, and the value of Rj may differ in each instance in which it occurs. For example, if Ri and Rj are independently selected from the group consisting of methyl, ethyl, propyl and butyl, then (CRiRj)₂ can be

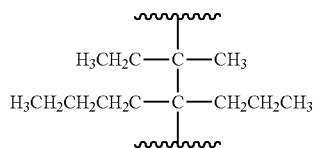

The term $(C_{1-6})$alkyl as used hereinabove means a branched or unbranched alkyl group having 1-6 carbon atoms, for example methyl, ethyl, propyl, isopropyl, butyl, tert-butyl, n-pentyl and n-hexyl. Preferred is $(C_{1-4})$alkyl.

The term $(C_{1-5})$alkyl means a branched or unbranched alkyl group having 1-5 carbon atoms, for example methyl, ethyl, propyl, isopropyl, butyl, tert-butyl and n-pentyl.

The term $(C_{1-4})$alkyl as used herein means a branched or unbranched alkyl group having 1-4 carbon atoms, being methyl, ethyl, n-propyl, isopropyl, n-butyl, isobutyl, sec-butyl and tert-butyl.

The term $(C_{1-3})$alkoxy means an alkoxy group having 1-3 carbon atoms, the alkyl moiety being branched or unbranched.

The term $(C_{1-3})$alkoxycarbonyl means an alkoxycarbonyl group having 1-3 carbon atoms in the alkoxy moiety, the alkoxy moiety having the same meaning as previously defined.

The term (di)$(C_{1-6})$alkylaminocarbonyl means an alkylaminocarbonyl group, the amino group of which is mono-substituted or disubstituted independently with an alkyl group which contains 1-6 carbon atoms and which has the same meaning as previously defined. Preferred alkyl group is $(C_{1-4})$alkyl.

The term $(C_{3-7})$cycloalkyl means a cycloalkyl group having 3-7 carbon atoms, such as cyclopropyl, cyclobutyl, cyclopentyl, cyclohexyl and cycloheptyl. 5-6 Carbon atoms are preferred.

The term $(C_{3-5})$heterocycloalkyl means a heterocycloalkyl group having 3-5 carbon atoms, including 1-3 heteroatoms selected from N, O and/or S, which may be attached via a nitrogen if feasible, or a carbon atom. Preferred number of heteroatoms is one or two. Most preferred number is one. Preferred heteroatoms are N or O. Most preferred are piperazinyl, tetrahydropyranyl, morpholinyl and pyrrolidinyl.

A group having the formula

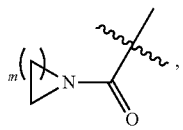

means a heterocyclocarbonyl group such as

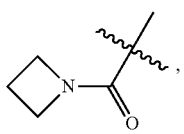

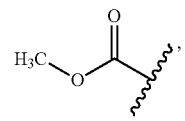

each optionally substituted with one or more $(C_{1-10})$alkyl, halogen, amino, cyano, hydroxy, and $(C_{1-3})$alkoxy.

The term $(C_{2-9})$heteroaryl means an aromatic group having 2-9 carbon atoms and 1-3 heteroatoms selected from N, O and S, like imidazolyl, thiadiazolyl, pyridinyl, pyrimidinyl, thiophenyl or furyl, pyrazolyl, isoxazolyl or quinolyl. Preferred number of heteroatoms is one or two. Preferred heteroaryl groups are pyrazolyl, thiophenyl, isoxazolyl, pyridyl and quinolyl. The $(C_{2-5})$heteroaryl group may be attached via a carbon atom or a nitrogen, if feasible.

The term $(C_{6-14})$aryl means an aromatic hydrocarbon group having 6-14 carbon atoms, such as phenyl, naphthyl, tetrahydronaphthyl, indenyl, anthracyl, More preferred are $(C_{6-10})$ aryl groups. The most preferred aromatic hydrocarbon group is phenyl.

As used herein, the term "$X_a$-$X_b$", shall have the same meaning as the term "$X_{a-b}$", wherein X is any atom and a and b are any integers. For example, "$C_1$-$C_4$" shall have the same meaning as "$C_{1-4}$". Additionally, when referring to a functional group generically, "$A^x$" shall have the same meaning, and be interchangeable with, "AX", wherein "A" is any atom and "x" or "X" are any integer. For example, "$R^1$" shall have the same meaning, and be interchangeable with, "R1".

In the above definitions with multifunctional groups, the attachment point is at the last group. For example, the term $(C_{1-3})$alkoxycarbonyl refers to, e.g.

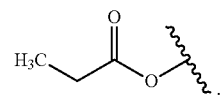

and the term (C1-4)alkylcarbonyloxy refers to, e.g.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into an efficacious therapeutic agent. Accordingly, the term "one or more" when referring to a substituent and/or variable means that one or more hydrogens on the designated atom/atoms is/are replaced with a selection from the indicated group, provided that the designated atom's normal valency under the existing circumstances is not exceeded, and that the substitution results in a stable compound.

The term "optionally substituted" means that a substitution with the specified groups, radicals, or moieties may or may not be made on the specified group.

When, in the definition of a substituent, it is indicated that "all of the alkyl groups" of said substituent are optionally substituted, this also includes the alkyl moiety of an alkoxy group.

The use of the terms "salt", "solvate", "ester", "prodrug", and the like is intended to equally apply to the salt, solvate, ester, and prodrug of enantiomers, stereoisomers, rotamers, tautomers, positional isomers, racemates, or prodrugs of the inventive compounds.

The term "effective amount" as used herein refers to an amount of the compound of Formula (I) and/or an additional therapeutic agent, or a composition thereof, that is effective in producing the desired therapeutic, ameliorative, inhibitory or preventative effect when administered to a subject suffering from an RORgammaT-mediated disease or disorder. In the combination therapies of the present invention, as effective amount can refer to each individual agent or to the combination as a whole, wherein the amounts of all agents administered are together effective, but wherein the component agent of the combination may not be present individually in an effective amount.

A "subject" is a human or non-human mammal. In one embodiment, a subject is a human. In another embodiment, a subject is a chimpanzee.

It should be noted that any carbon as well as heteroatom with unsatisfied valences in the text, schemes, examples and tables herein is assumed to have the sufficient number of hydrogen atom(s) to satisfy the valences.

The compounds of this invention include the prodrugs, hydrates or solvates of the compounds.

Optical Isomers-Diastereomers-Geometric Isomers-Tautomers

The compounds of Formula I may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen. Such compounds are referred to as tautomers. For example, compounds including carbonyl —CH$_2$C(O)— groups (keto forms) may undergo tautomerism to form hydroxyl —CH=C(OH)— groups (enol forms). Both keto and enol forms, individually as well as mixtures thereof, are included within the scope of the present invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula (I) may be atropisomers (e.g. substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters, and prodrugs of the compounds as well as the salts, solvates, and esters of the prodrugs), such as those that may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzyl-ethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

The compounds of Formula I can form salts which are also within the scope of this invention. Reference to a compound of Formula I herein is understood to include reference to salts thereof, unless otherwise indicated.

The term pharmaceutically acceptable salt represents those salts that are, within the scope of medical judgment, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide, calcium hydroxide, calcium carbonate, ammonium (e.g. diethylamine) or lithium hydroxide.

Solvates

The present invention includes within its scope solvates of compounds of Formula I. As used herein, the term "solvate" refers to a complex of variable stoichiometry formed by a solute (i.e., a compound of Formula I) or a pharmaceutically acceptable salt thereof and a solvent that does not interfere with the biological activity of the solute. Examples of solvents include but are not limited to water, ethanol, and acetic acid. When the solvent is water, the solvate is known as hydrate; hydrate includes, but is not limited to, hemi-, mono, sesqui-, di- and trihydrates.

The compounds of the invention may form hydrates or solvates. It is known to those of skill in the art that charged compounds form hydrated species when lyophilized with water, or form solvated species when concentrated in a solution with an appropriate organic solvent. One or more compounds of the invention may exist in unsolvated as well as solvated forms with pharmaceutically acceptable solvents such as water, ethanol, and the like, and it is intended that the invention embrace both solvated and unsolvated forms. "Solvate" may also mean a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Prodrugs

The present invention includes within its scope the use prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of formula I or with a compound that may not be a compound of formula I, but that converts to a compound of formula I in vivo after administration to the patient. Conventional procedures for the selection and preparation of suitable prodrug derivatives are described, for example, in "Design of Prodrugs," ed. H. Bundgaard, Elsevier, 1985.

The term "prodrug" means a compound (e.g., a drug precursor) that is transformed in vivo to yield a compound of Formula I or a pharmaceutically acceptable salt, hydrate or solvate of the compound. The transformation may occur by various mechanisms (e.g., by metabolic or chemical processes), such as, for example, through hydrolysis in blood. A discussion of drugs and the use of prodrugs is provided by T. Higuchi and W. Stella, "Prodrugs as Novel Delivery Systems," Vol. 14 of the A.C.S. Symposium Series, 1987; and in Bioreversible Carriers in Drug Design, ed. Edward B. Roche, American Pharmaceutical Association and Pergamon Press, 1987.

Isotopes

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. In light of the present disclosure, isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

Compounds of the present invention alter the interaction of coregulator proteins with Retinoic Acid Receptor-related Orphan Receptor gamma t (RORgammaT) and thereby antagonize RORgammaT-mediated transcriptional activity, and as such are useful in the treatment of diseases and conditions in which inhibition of RORgammaT is desirable, such as autoimmune and inflammatory diseases and disorders.

Accordingly, another embodiment of the present invention provides a method for treating a disease or condition mediated by RORgammaT in a subject comprising administering to the subject an amount of a compound having Formula I, Ia, Ib, Ic, Id, Ie, If, Ig or Ih, or a pharmaceutically acceptable salt or solvate thereof, that is effective for treating the disease or condition mediated by RORgammaT in the subject.

The compounds according to the invention can be used in therapy.

A further aspect of the invention resides in the use of compounds according to the invention or a pharmaceutically acceptable salt thereof for the treatment of RORgammaT-mediated diseases or RORgammaT mediated conditions.

Another aspect of the invention resides in the use of compounds or a pharmaceutically acceptable salt thereof having the general formula I for the treatment of autoimmune diseases, in particular those diseases in which Th17 cells and non-Th17 cells, which express Th17 hallmark cytokines, play a prominent role. These include, but are not limited to, the treatment of rheumatoid arthritis, psoriasis, inflammatory bowel disease, Crohn's disease and multiple sclerosis.

In another aspect, compounds or a pharmaceutically acceptable salt thereof having the general formula I can be used for treatment of inflammatory diseases in which Th17 cells and/or non-Th17 cells, which express Th17 hallmark cytokines, play a prominent role, such as but not limited to respiratory diseases, osteoarthritis and asthma. Also, compounds or a pharmaceutically acceptable salt thereof having the general formula I can be used for treatment of infectious diseases in which Th17 cells and/or non-Th17 cells, which express Th17 hallmark cytokines, play a prominent role, such as but not limited to mucosal leishmaniasis.

Compounds or a pharmaceutically acceptable salt thereof having the general formula I can also be used for treatment of other diseases in which Th17 cells and/or non-Th17 cells, which express Th17 hallmark cytokines, play a prominent role, such as but not limited to Kawasaki disease and Hashimoto's thyroiditis.

In one aspect the disease or condition is an autoimmune disease or inflammatory disease. The disease or condition includes, but is not limited to, multiple sclerosis, inflammatory bowel disease, Crohn's disease, ankylosing spondylitis, psoriasis, rheumatoid arthritis, asthma, osteoarthritis, Kawasaki disease, Hashimoto's thyroiditis or mucosal leishmaniasis.

In another aspect, the compounds according to the invention can be used in therapies to treat or prevent multiple sclerosis, inflammatory bowel disease, Crohn's disease, psoriasis, rheumatoid arthritis, asthma, osteoarthritis, Kawasaki disease, Hashimoto's thyroiditis and mucosal leishmaniasis.

In another aspect the compounds according to the invention can be used to treat or prevent psoriasis.

In yet another aspect the compounds according to the invention can be used to treat inflammatory bowel disease.

This aspect of the present invention further includes the use of a compound of Formula I, Ia, Ib, Ic, Id, Ie, If, Ig or Ih, or a pharmaceutically acceptable salt or solvate thereof, in the manufacture of a medicament for the treatment of a disease or condition mediated by RORgammaT.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration that include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1.0-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., autoimmune and inflammatory diseases and disorders.

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition, Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive that does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

Pharmaceutical Compositions

Another aspect of the present invention provides pharmaceutical compositions comprising a compound of Formula I or a pharmaceutically acceptable salt or solvate thereof and one or more pharmaceutically acceptable excipients. The term "excipient" and "carrier" may be used interchangeably. The term "composition", as in pharmaceutical composition, is intended to encompass a product comprising the active ingredient(s), and the inert ingredient(s) (pharmaceutically acceptable excipients) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

The present invention also relates to a pharmaceutical composition comprising compounds or pharmaceutically acceptable salts thereof having the general formula I in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-100 mg per kg body weight. The desired dose may be presented as one dose or as multiple subdoses administered at appropriate intervals throughout the day. The dosage as well as the regimen of administration may differ between a female and a male recipient.

Combination Therapy

Compounds of the present invention, and their salts and solvates, and physiologically functional derivatives thereof, may be employed alone or in combination with other therapeutic agents for the treatment of diseases and conditions associated with inappropriate IL-17 pathway activity. Combination therapies according to the present invention thus comprise the administration of at least one compound of formula (I) or a pharmaceutically acceptable salt or solvate thereof, or a physiologically functional derivative thereof, and the use of at least one other pharmaceutically active agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect. For the treatment of the inflammatory and autoimmune diseases, rheumatoid arthritis, psoriasis, inflammatory bowel disease, ankylosing spondylitis, SLE, uveitis, atopic dermatitis, COPD, asthma and allergic rhinitis a compound of formula (I) may be combined with one or more other active agents such as: (1) TNF-a inhibitors; (2) non-selective COX-I/COX-2 inhibitors; (3) COX-2 inhibitors; (4) other agents for treatment of inflammatory and autoimmune diseases including glucocorticoids, methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist; (6) LTD4 receptor antagonist; (7) PDE4 inhibitor; (8) antihistamine HI receptor antagonists; (9) a1- and a2-adrenoceptor agonist; (10) anticholinergic agents; (11) β-adrenoceptor agonists; (12) insulin-like growth factor type I (IGF-1) mimetic; (13) glucocorticosteroids; (14) kinase inhibitors such as inhibitors of the Janus Kinases (JAK 1 and/or JAK2 and/or JAK 3 and/or TYK2), p38 MAPK and IKK2; (15) B-cell targeting biologies such as rituximab; (16) selective costimulation modulators such as abatacept; (17) interleukin inhibitors, such as IL-1 inhibitor anakinra, IL-6 inhibitor tocilizumab, and IL12/IL-23 inhibitor ustekinumab. It could also be combined with anti-IL17 antibodies to obtain additive/synergistic responses for the treatment of inflammatory and autoimmune diseases.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Accordingly, the pharmaceutical compositions of the present invention include those that also comprise at least one additional therapeutically active agent, in addition to the compound of Formula I, Ia, Ib, Ic, Id, Ie, If, Ig or Ih.

The invention further includes a compound of Formula I in combination with one or more other drug(s).

Methods of Synthesis

Methods for preparing the compounds of this invention are illustrated in the following schemes and examples. Other synthetic protocols will be readily apparent to those skilled in the art in light of the present disclosure. The examples illustrate the preparation of the compounds of formula I and as such are not to be considered as limiting the invention set forth in the claims appended hereto. Unless otherwise indicated, all variables are as previously defined.

All the end products of the formula I were analyzed by NMR and/or LCMS. Intermediates were analyzed by NMR and/or TLC and/or LCMS. Most compounds were purified by reverse phase HPLC, MPLC on silica gel, recrystallization and/or swish (suspension in a solvent followed by filtration of the solid). The course of the reactions was followed by thin layer chromatography (TLC) and/or LCMS and/or NMR and reaction times are given for illustration only.

Abbreviations used herein are as follows: EtOAc: Ethyl acetate; PE: Petroleum ether; EA: Ethyl acetate; DCM: Dichloromethane; DMF: N,N-dimethylformamide; THF: tetrahydrofuran; DMSO: Dimethyl sulfoxide; TBAI: Tetrabutylammonium iodide; MeOH: methanol TsCl: 4-toluenesulfonyl chloride; DMAP: N,N-dimethylpyridin-4-amine; $Et_3N$: triethylamine; ACN: acetonitrile; MsCl: methanesulfonyl chloride; $(COCl)_2$: oxalylchloride; $LiBH_4$: lithium tetrahydroborate; t-BuOK: Potassium tert-butoxide; BPO: dibenzoyl peroxide.

Scheme 1 illustrates a general method toward the preparation of the compounds of formula I. Starting from halide A, N-alkylation with substituted benzyl halide or tosylate in the presence of appropriate base led to the formation of compound B. Subsequent Suzuki coupling with pinacol boronic ester or acid followed by ester hydrolysis afforded the final compound I. In certain cases, ester hydrolysis took place under the Suzuki coupling condition and led to the formation of the final product I.

Scheme 1.

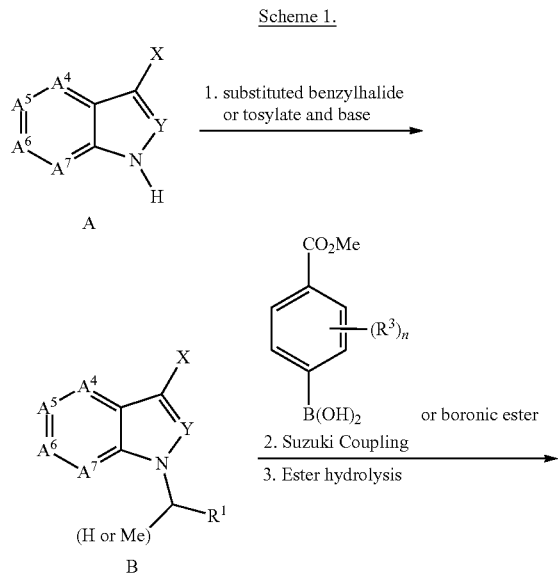

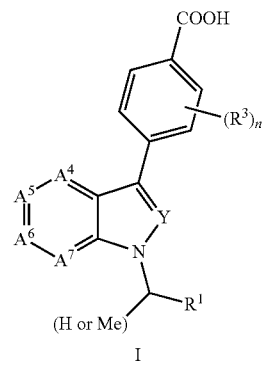

Alternatively the final compound I could also be prepared by switching the order of reaction sequence between N-alkylation and Suzuki coupling (see Scheme 2). Suzuki coupling first by reacting halide A with boronic ester or acid gave intermediate B. Subsequent N-alkylation followed by hydrolysis furnished final product. However, the more efficient way to prepare B from A was through a 3-step protected/Suzuki/deprotected sequence. Boc or THP protection of A gave intermediate C. Subsequent Suzuki coupling followed by deprotection under acidic conditions provided desired intermediate B.

Scheme 2.

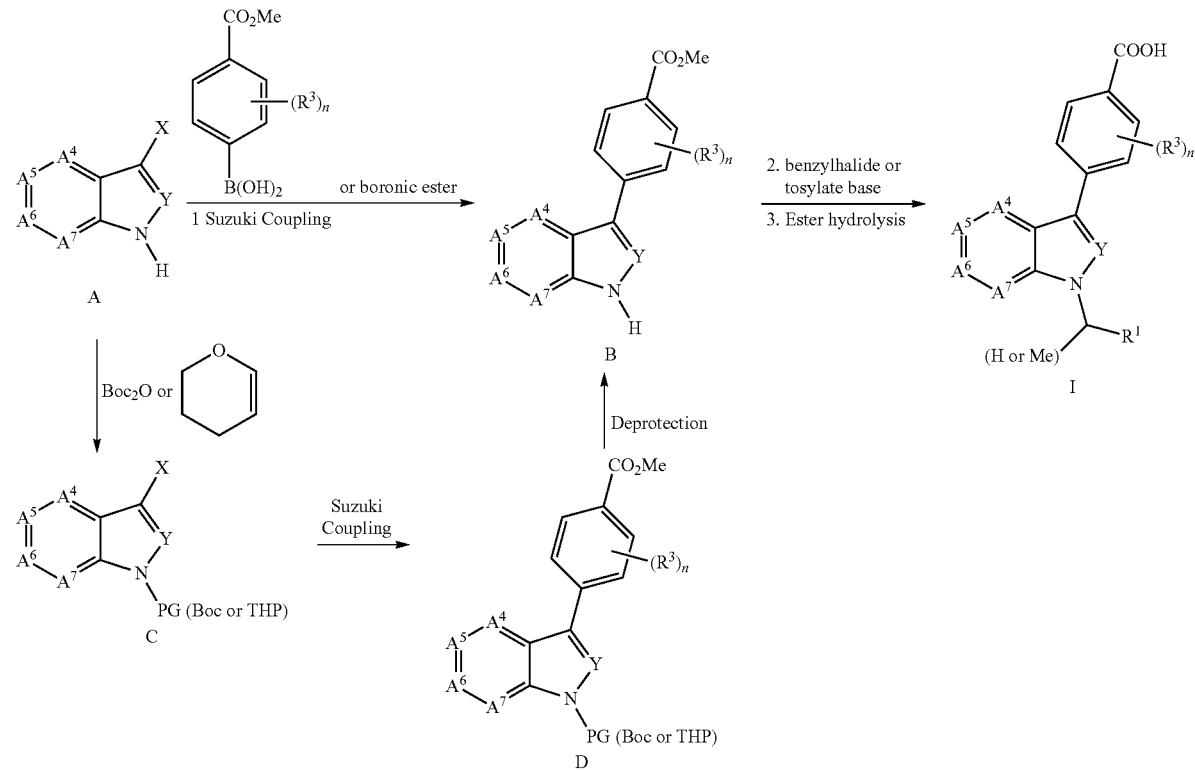

Scheme 3 illustrates a general method toward the preparation of compounds of formula I that contain amide moiety at indazole 6-position. Starting from halide A, N-alkylation with substituted benzyl halide or tosylate in the presence of appropriate base led to the formation of compound B. Subsequent ester hydrolysis and amide coupling afforded intermediate C, which could be easily converted into intermediate D via Suzuki coupling. Depending on the nature of $R^3$ substituents, either hydrolysis or deprotection followed by ester hydrolysis led to the formation of the final product I.

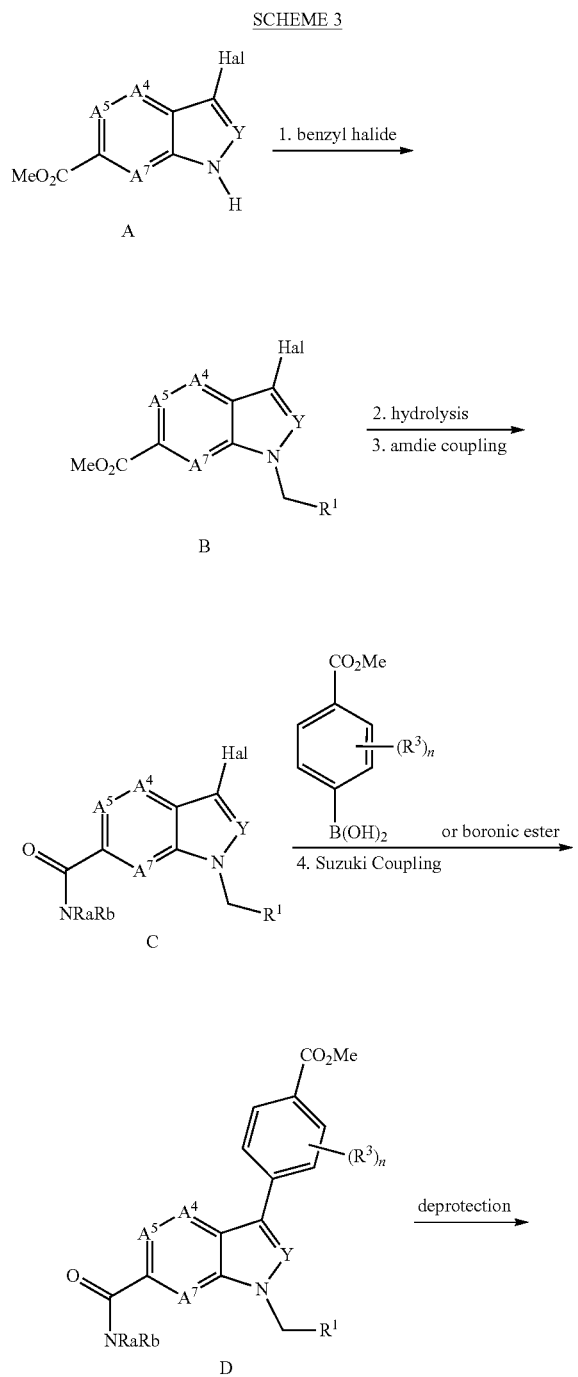

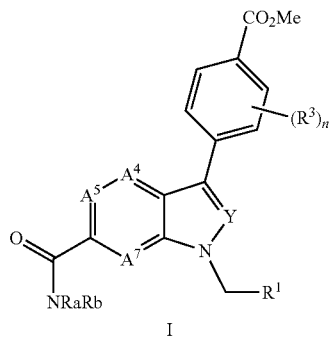

COMMERCIALLY AVAILABLE/PREVIOUSLY DESCRIBED MATERIALS

The following table lists commercial sources, and previously disclosed synthetic routes for chemical materials employed in the synthesis of intermediates and that can be used in the synthesis of examples of the instant invention. The list is not intended to be exhaustive, exclusive, or limiting in any way.

| Structure | Source |
|---|---|
| 3-bromo-6-azaindole | Bellen |
| 3-bromo-pyrazolo[3,4-b]pyridine | APOLLO |
| 2-bromo-6-fluorobenzyl bromide | ACC |
| 4-fluoro-1H-indazole | Oakwood |
| methyl 5-fluoro-2-methoxy-4-(4,4,5,5-tetramethyl-1,3,2-dioxaborolan-2-yl)benzoate | WO2008138889 |

| Structure | Source |
|---|---|
| 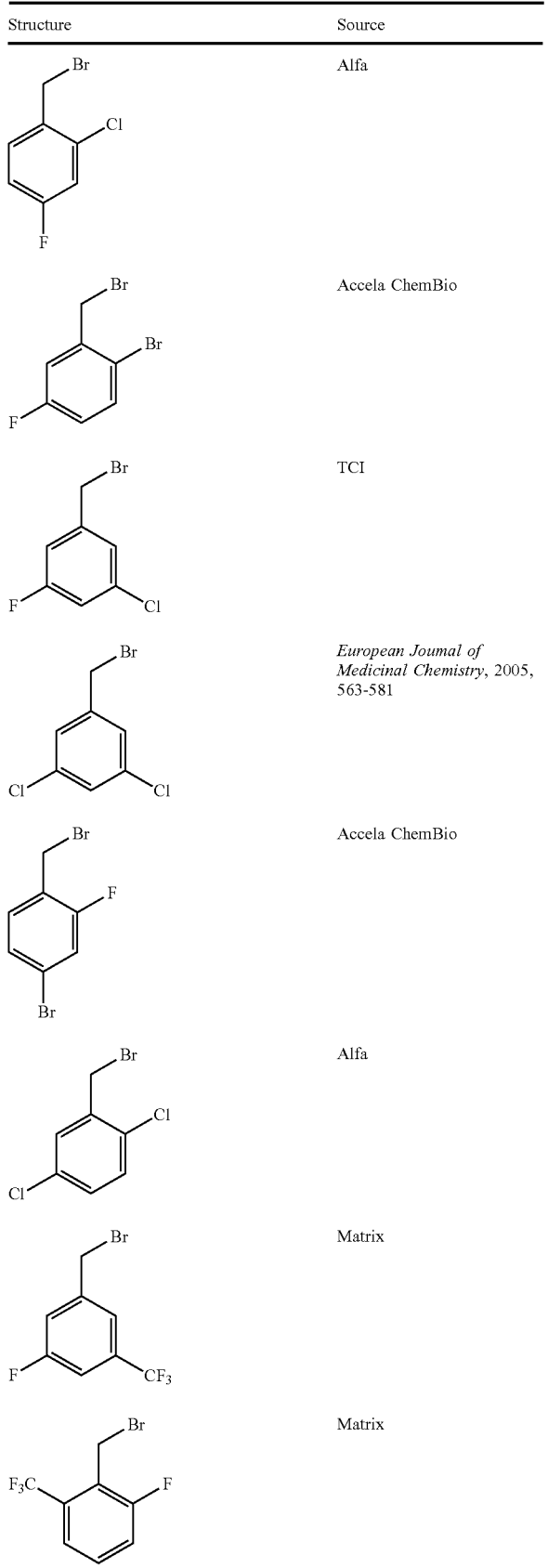 | Alfa |
| | Accela ChemBio |
| 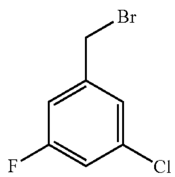 | TCI |
| 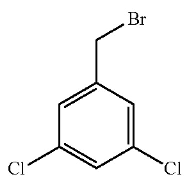 | European Journal of Medicinal Chemistry, 2005, 563-581 |
| | Accela ChemBio |
| | Alfa |
| | Matrix |
| | Matrix |

| Structure | Source |
|---|---|
| 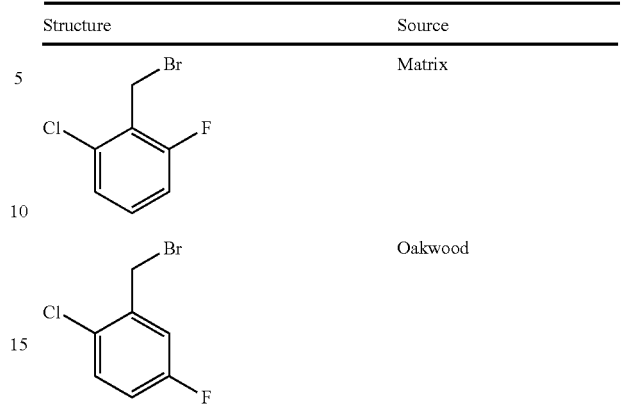 | Matrix |
| 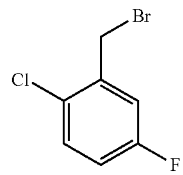 | Oakwood |

INTERMEDIATES

Example i-1

Preparation of (2-chloro-6-(trifluoromethyl)phenyl)methanol (i-1)

Scheme i-1

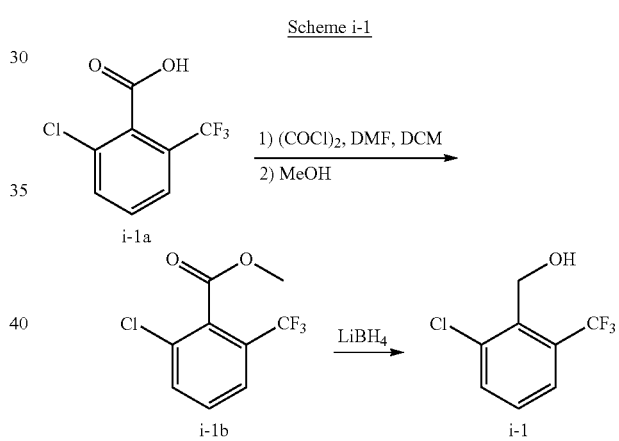

i). Preparation of methyl 2-chloro-6-(trifluoromethyl)benzoate (i-1b)

A mixture of 2-chloro-6-(trifluoromethyl)benzoic acid (i-1a) (1.5 g, 6.70 mmol) and (COCl)$_2$ (1.1 ml, 12.8 mmol) in DCM (20 ml) and DMF (5 drops) were stirred at room temperature for 2 h. MeOH (0.41 ml, 13.4 mmol) was added dropwise and the reaction mixture was stirred at room temperature for another 30 min. The resultant solution was diluted with H$_2$O (50 ml) and the aqueous layer was extracted with DCM (50 ml×2). The combined organic layers were washed with brine (50 ml×1), dried over anhydrous Na$_2$SO$_4$ and concentrated to obtain the title compound i-1b as a pale yellow oil. LCMS (ESI) calc'd for C$_9$H$_6$ClF$_3$O$_2$ [M+H]$^+$: 239. found: 239.

ii) Preparation of (2-chloro-6-(trifluoromethyl)phenyl)methanol (i-1)

A mixture of methyl 2-chloro-6-(trifluoromethyl)benzoate (i-1b) (1.0 g, 4.20 mmol) and LiBH$_4$ (0.18 g, 8.40 mmol)

in THF (10 ml) was stirred at room temperature for 14 h. 2M HCl (10 ml) was added to quench the reaction and the aqueous layer was extracted with EtOAc (20 ml×3). The combined organic layers were washed with brine (20 ml), dried over anhydrous Na$_2$SO$_4$ and concentrated to give the title compound i-1. LCMS (ESI) calc'd for C$_8$H$_6$ClF$_3$O [M+H]$^+$: 211. found: 211.

Example i-2

Preparation of 1-(2-chloro-6-(trifluoromethyl)phenyl)ethanol (i-2)

Scheme i-2

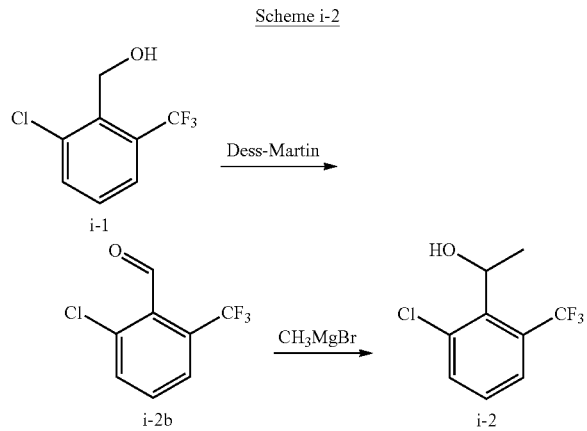

i) Preparation of 2-chloro-6-(trifluoromethyl)benzaldehyde (i-2b)

A mixture of (2-chloro-6-(trifluoromethyl)phenyl)methanol (i-1) (0.7 g, 3.33 mmol) and Dess-Martin periodinane (2.8 g, 6.66 mmol) in DCM (15 ml) was stirred at room temperature for 14 h. The resultant solution was diluted with H$_2$O (30 mL) and the aqueous layer extracted with DCM (30 ml×3). The combined organic layers were washed with brine (30 ml), dried over anhydrous Na$_2$SO$_4$ and concentrated. The residue was purified by flash chromatography (PE/EtOAc=10:1) to give the title compound i-2b as a pale yellow solid. LCMS (ESI) calc'd for C$_8$H$_4$ClF$_3$O [M+H]$^+$: 209. found: 209.

ii) Preparation of 1-(2-chloro-6-(trifluoromethyl)phenyl)ethanol (i-2)

A mixture of 2-chloro-6-(trifluoromethyl)benzaldehyde (i-2b) (0.25 g, 1.20 mmol) in anhydrous THF (10 ml) was cooled to 0° C. in an ice-water bath and CH$_3$MgBr (3.0M solution in ether, 2.0 ml, 6.0 mmol) was added dropwise. The reaction mixture was warmed to room temperature and stirred for 2 h. Saturated NH$_4$Cl solution (20 ml) was added to quench the reaction and the aqueous layer was extracted with ethyl acetate (20 ml×3). The combined organic layers were washed with brine (20 ml), dried over anhydrous Na$_2$SO$_4$ and concentrated to obtain the desired product i-2 as pale yellow oil. LCMS (ESI): calc'd for C$_9$H$_8$ClF$_3$O [M+H]$^+$: 225. found: 225.

Example i-3

Preparation of methyl 5-fluoro-4-(4-fluoro-1H-indazol-3-yl)-2-methoxybenzoate (i-31)

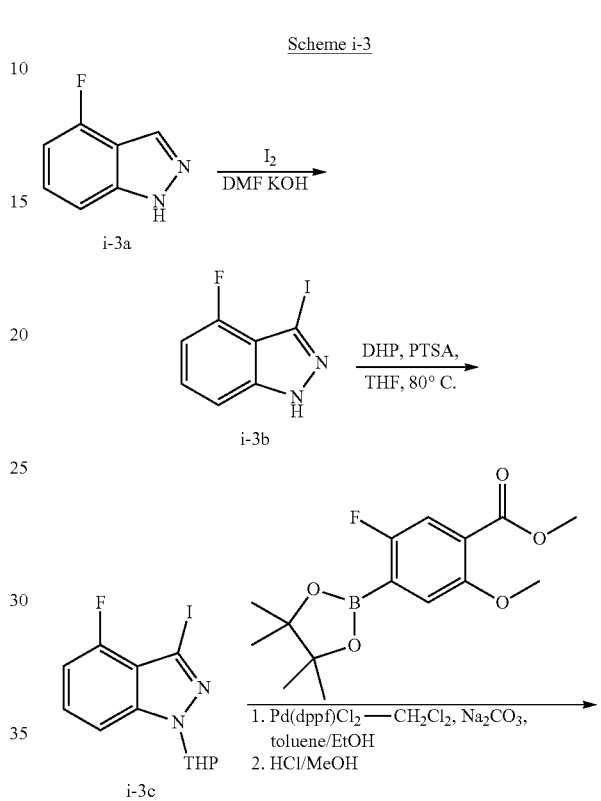

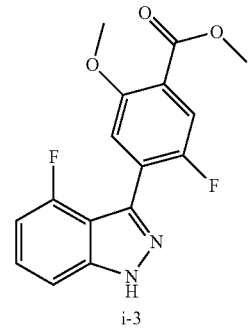

i). Preparation of 4-fluoro-3-iodo-1H-indazole (i-3b)

To a solution of 4-fluoro-1H-indazole (i-3a) (24 g, 180 mmol) in DMF (300 ml) was added iodine (56 g, 216 mmol) and KOH (40 g, 720 mmol) at 0° C. The resultant mixture was allowed to warm to room temperature and stirred for 5 h. The reaction mixture was slowly quenched with saturated sodium thiosulfate (200 mL) and extracted with EtOAc (500 mL×3). The combined organic layers were washed, dried and concentrated, and the residue was purified by re-crystallization to afford the title compound (30 g, yield: 65%). LCMS (ESI) calc'd for C$_7$H$_4$FIN$_2$ [M+H]$^+$: 263. found: 263.

ii). Preparation of 4-fluoro-3-iodo-1-(tetrahydro-2H-pyran-2-yl)-1H-indazole (i-3c)

To a solution of 4-fluoro-3-iodo-1H-indazole (i-3b) (10 g, 38.1 mmol) in 150 mL of THF was added DHP (11.5 g, 122.4 mmol) and PTSA (776 mg, 4 mmol). The reaction mixture was heated to reflux for 6 h. The reaction mixture was poured into water. The mixture was extracted with EtOAc (300 mL×3) and the combined organic extracts were washed with brine, dried over $Na_2SO_4$ and concentrated. The crude residue was purified by silica gel chromatography (PE:EtOAc=50:1 to 5:1) to afford the title compound (7 g, yield: 54%) as a yellow solid. LCMS (ESI) calc'd for $C_{12}H_{12}FIN_2O$ [M+H]$^+$: 347. found: 347.

iii). Preparation of methyl 5-fluoro-4-(4-fluoro-1H-indazol-3-yl)-2-methoxybenzoate (i-3)

To a mixture of 4-fluoro-3-iodo-1-(tetrahydro-2H-pyran-2-yl)-1H-indazole (i-3c) (1.0 g, 2.89 mmol) and methyl 5-fluoro-2-methoxy-4-(4,4,5,5-tetramethyl-1,3,2-dioxaborolan-2-yl)benzoate (1.3 g, 4.3 mmol) in a 1:1 mixture of toluene/EtOH (30 ml) were added 2 mL of saturated $Na_2CO_3$ solution and Pd(dppf)Cl$_2$—CH$_2$Cl$_2$ (86 mg, 0.03 mmol) under N$_2$, and the reaction mixture was heated to 120° C. for 6 h. The mixture was filtered through celite and the organic layer was concentrated in vacuo. To the crude was added 4N HCl in MeOH (20 mL) and the reaction mixture was heated to reflux for 14 h, then cooled, and neutralized with 2N NaOH solution to pH=7, and a white solid precipitated out which was collected through filtration and washed with PE (100 mL). The solid was dried in vacuo to afford the title compound (600 mg, 65%) as a light yellow solid. LCMS (ESI) calc'd for $C_{16}F_{12}F_2N_2O_3$ [M+H]$^+$: 319. found: 319.

Example i-4

Preparation of 1-bromo-2-(bromomethyl)-3-(trifluoromethyl)benzene (i-4)

Scheme i-4

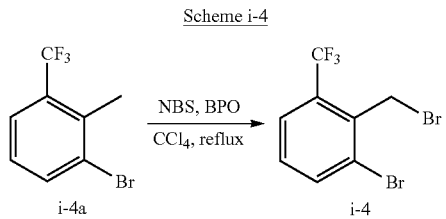

i). Preparation of 1-bromo-2-(bromomethyl)-3-(trifluoromethyl)benzene (i-4)

To a solution of 1-bromo-2-methyl-3-(trifluoromethyl) benzene (i-4a) (2 g, 8.36 mmol) in CCl$_4$ (20 mL) was added NBS (1.49 g, 8.36 mmol), dibenzoyl peroxide (20 mg, 0.08 mmol). The mixture was stirred under nitrogen at 100° C. for 16 h. The solvent was removed in vacuo, and the residue was partitioned between water (15 mL) and DCM (15 mL). The water layer was extracted with DCM (15 mL×3). The combined organic layers were dried over anhydrous Na$_2$SO$_4$ and evaporated under reduced pressure. The residue was purified by column chromatography on silica gel (PE/EtOAc=50/1) to afford the title compound (1.16 g, purity 80%, yield: 43%). LCMS (ESI) calc'd for $C_8H_5Br_2F_3$ [M+H]$^+$: 317. found: 317.

Example i-5

Preparation of 2-(bromomethyl)-1-chloro-3-cyclopropylbenzene (i-5)

Scheme i-5

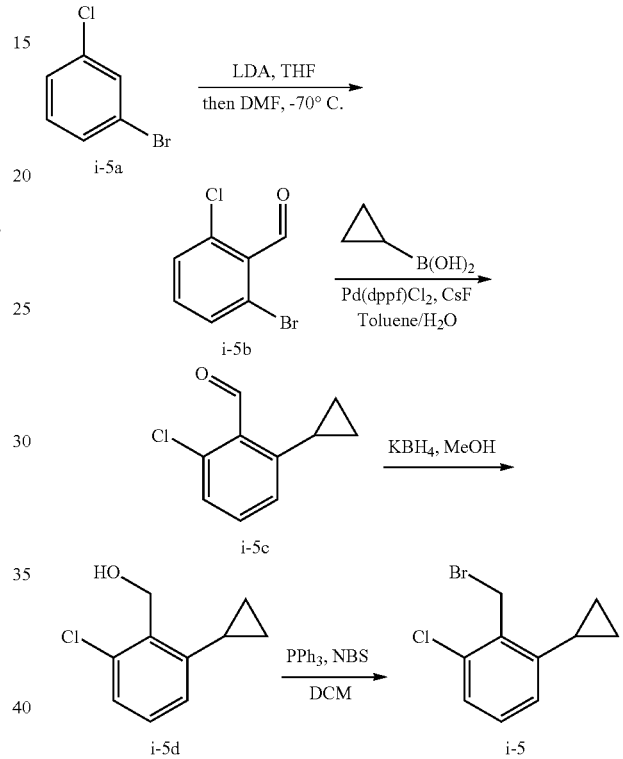

i). Preparation of 2-bromo-6-chlorobenzaldehyde (i-5b)

To a solution of 1-bromo-3-chlorobenzene (i-5a) (5 g, 26. mmol) in THF (50 mL) was added LDA (1 M, 31.3 mL, 8.7 mmol) dropwise via an addition funnel at −70° C. The mixture was stirred at −70° C. for 1 h. DMF (2.87 mL, 39.1 mmol, 227 mmol) in THF (20 mL) was added dropwise maintaining the internal temperature below −70° C. The reaction was stirred vigorously at −70° C. for 1 h. Warmed to −30° C., the reaction was poured into 1 M HCl (100 mL) partitioned between water (10 mL) and DCM (30 mL). The aqueous layer was extracted with DCM (20 mL×3). The combined organic layers were dried over anhydrous Na$_2$SO$_4$ and concentrated in vacuo to afford the title compound (3.6 g, yield: 59%). LCMS (ESI) calc'd for $C_7H_4BrClO$ [M+H]$^+$: 219. found: 219.

ii). Preparation of 2-chloro-6-cyclopropylbenzaldehyde (i-5c)

To a mixture of 2-bromo-6-chlorobenzaldehyde (i-5b) (15 g, 68.3 mol), cyclopropyl boronic acid (11.7 g, 136.6 mmol), Cs₂CO₃ (20.8 g, 136.6 mmol) in toluene (200 mL) and H₂O (40 mL) was added Pd(dppf)Cl₂ (0.75 mg, 0.9 mmol). The mixture was stirred under N₂ at 100° C. for 16 h. The solvent was evaporated and the residue was diluted with DCM (50 mL) and H₂O (20 ml). The organic layer was separated, washed with H₂O, dried over Na₂SO₄ and evaporated in vacuo. The residue was purified by column chromatography on silica gel (PE/EtOAc=5/1) to give the title compound (6 g, yield: 48%) as a white solid. LCMS (ESI) calc'd for $C_{10}H_9ClO$ [M+H]⁺: 181. found: 181.

iii). Preparation of (2-chloro-6-cyclopropylphenyl)methanol (i-5d)

To a mixture of 2-chloro-6-cyclopropylbenzaldehyde (i-5c) (6 g, 33.3 mol) in MeOH (50 mL) was added KBH₄ (902 mg, 16.7 mmol) in portions at 0° C. The mixture was stirred at 0° C. for 2 h. The solvent was evaporated and the residue was diluted with DCM (20 mL), followed by washing with water (2×20 mL). The organic phase was dried over Na₂SO₄ and evaporated in vacuo. The residue was purified by column chromatography on silica gel (PE/EA=2/1) to give the title compound (2 g, yield: 33%) as a white solid. LCMS (ESI) calc'd for $C_{10}H_{11}ClO$ [M+H]⁺: 183. found: 183.

iv). Preparation of 2-(bromomethyl)-1-chloro-3-cyclopropylbenzene (i-5)

To a solution of (2-chloro-6-cyclopropylphenyl)methanol (i-5d) (400 mg, 2.2 mmol) in DCM (6 mL) was added PPh₃ (865 mg, 3.3 mmol), NBS (587 mg, 3.3 mmol) at 10° C. The mixture was stirred at 10° C. for 4 h. The resulting mixture was concentrated in vacuo, and the residue was purified by column chromatography on silica gel (PE/EtOAc=50/1) to afford the title compound (350 mg, yield: 65%) as a colorless oil. LCMS (ESI) calc'd for $C_{10}H_{10}BrCl$ [M+H]⁺: 245. found: 245.

Example i-6

Preparation of 2-(bromomethyl)-1-chloro-3-methylbenzene (i-6)

i). Preparation of (2-chloro-6-methylphenyl)methanol (i-6b)

To a solution of 2-chloro-6-methylbenzoic acid (i-6a) (1 g, 5.9 mmol) in 10 mL of dry THF was added dropwise a solution of 1M BH₃ (17.6 mL, 17.6 mmol) in THF at 0° C. After addition, the mixture was heated to reflux for 8 h. The resulting mixture was cooled to 0° C., and quenched with 10 mL of MeOH, followed by the addition of 1 M HCl (4 ml). The mixture was extracted with DCM (30 mL×3), and the combined extracts were washed with brine (50 mL), dried over anhydrous sodium sulfate, and concentrated in vacuo. The residue was purified by column chromatography on silica gel (PE/EtOAc=20/1) to afford the title compound (800 mg, yield: 90%). LCMS (ESI) calc'd for $C_8H_9ClO$ [M+H]⁺: 157. found: 157.

ii). Preparation of 2-(bromomethyl)-1-chloro-3-methylbenzene (i-6)

To a solution of (2-chloro-6-methylphenyl)methanol (i-6b) (800 mg, 6 mmol) in DCM (10 ml) was added PPh₃ (2.2 g, 8.4 mmol), and NBS (1.3 g, 8.4 mmol) at 0° C. The mixture was stirred at room temperature for 8 h. The resulting mixture was diluted with water (20 mL) and extracted with EtOAc (20 mL×3). The combined organic layers were washed with brine (20 mL), dried over anhydrous Na₂SO₄ and concentrated in vacuo. The crude residue was purified by column chromatography on silica gel (PE/EtOAc=100/1) to give the title compound (800 mg, yield: 80%). LCMS (ESI) calc'd for $C_8H_8BrCl$ [M+H]⁺: 219. found: 219.

Example i-7

Preparation of methyl 3-fluoro-4-(4-fluoro-1H-indazol-3-yl)benzoate (i-7)

Scheme i-6

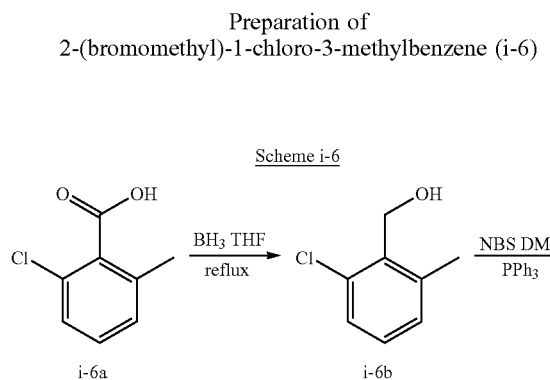

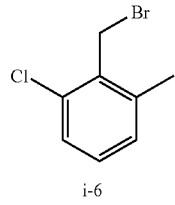

Scheme i-7

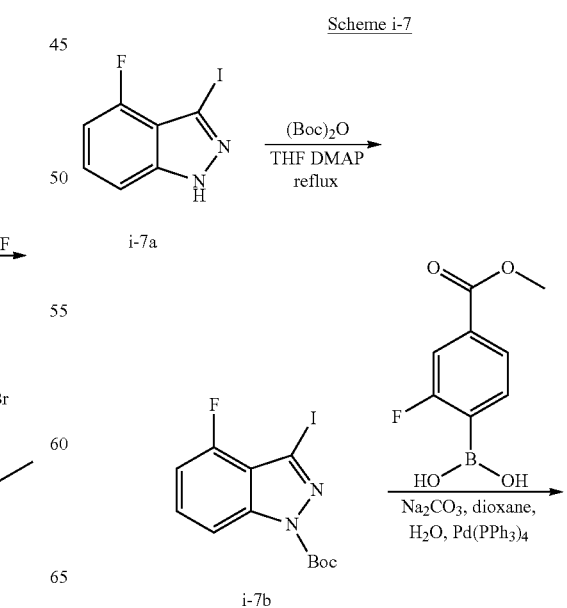

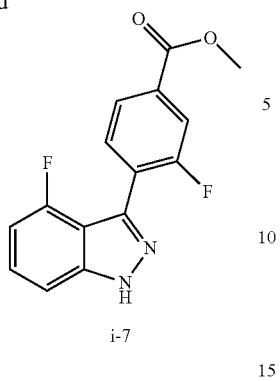

i-7 i). Preparation of tert-butyl 4-fluoro-3-iodo-1H-indazole-1-carboxylate (i-7b)

A solution of 4-fluoro-3-iodo-1H-indazole (i-7a) (2 g, 7.6 mmol), di-tert-butyl dicarbonate (1.9 g, 9.1 mmol) and DMAP (45 mg, 0.37 mmol) in THF (20 ml) was refluxed for 4 h, cooled to room temperature, and concentrated. The crude residue was purified by column (PE/EA=10/1) to afford the title compound (2.4 g, yield: 89%). LCMS (ESI) calc'd for $C_{12}H_{12}FIN_2O_2$ [M+H]$^+$: 363. found: 363.

ii). Preparation of methyl 3-fluoro-4-(4-fluoro-1H-indazol-3-yl)benzoate (i-7)

To a solution of tert-butyl 4-fluoro-3-iodo-1H-indazole-1-carboxylate (i-7b) (400 mg, 1.1 mmol) in a mixture of dioxane (5 ml) and H$_2$O (4/ml) was added (2-fluoro-4-(methoxy carbonyl)phenyl)boronic acid (300 mg, 1.5 mmol), sodium carbonate (600 mg, 5.5 mmol). The mixture was degassed with N$_2$, and then Pd(PPh$_3$)$_4$ (70 mg, 0.06 mmol) was added in one portion. The reaction mixture was heated at 90° C. for 5 h. The reaction mixture was diluted with water (10 mL), and extracted with EtOAc (25 mL×2). The combined organic layers were concentrated and the residue was purified by flash chromatography (PE: EtOAc=10:1) to afford the title compound (150 mg, yield: 35%). LCMS (ESI) calc'd for $C_{15}H_{10}F_2N_2O_2$ [M+H]$^+$: 289. found: 289.

Example i-8

Preparation of 1-(2-(bromomethyl)-3-chlorophenyl)cyclobutanol (i-8)

Scheme i-8

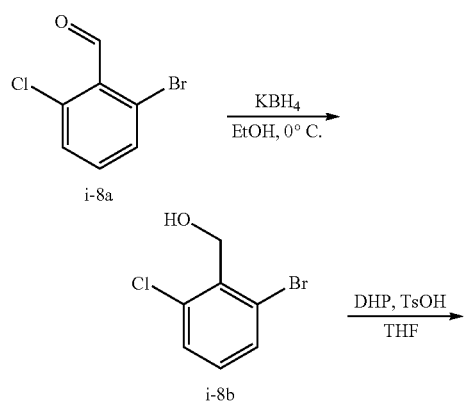

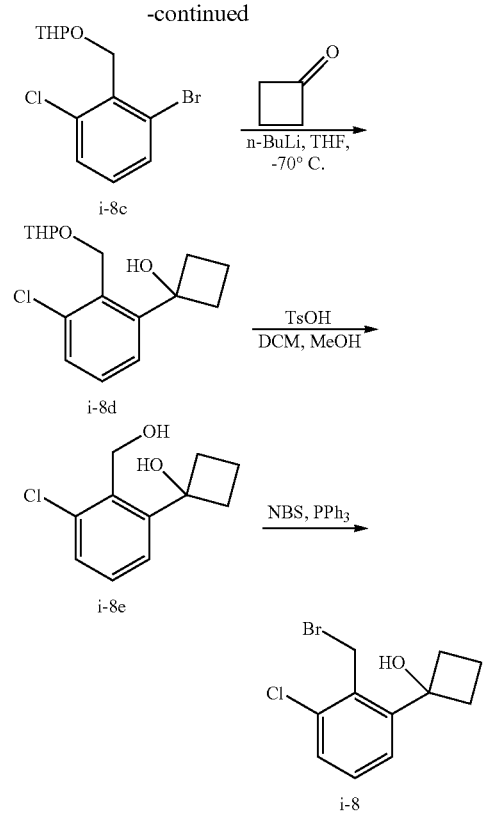

i). Preparation of (2-bromo-6-chlorophenyl)methanol (i-8b)

To a solution of 2-bromo-6-chlorobenzaldehyde (i-8a) (1.5 g, 6.8 mmol) in EtOH (20 mL) was added KBH$_4$ (1.49 g, 3.4 mmol) in portions at 0° C. The mixture was stirred at 0° C. for 2 h. The solvent was removed in vacuo, and the residue was partitioned between water (10 mL) and DCM (5 mL). The aqueous layer was extracted with DCM (5 mL×3). The combined organic layers were dried over anhydrous Na$_2$SO$_4$ and evaporated under reduced pressure. The residue was purified by flash chromatography on silica gel (PE/EtOAc=3/1) to afford the title compound (0.9 g, yield: 59.6%) as colorless oil. LCMS (ESI) calc'd for $C_7H_6BrClO$ [M+H]$^+$: 221. found: 221.

ii). Preparation of 2-((2-bromo-6-chlorobenzyl)oxy)tetrahydro-2H-pyran (i-8c)

To a solution of (2-bromo-6-chlorophenyl)methanol (i-8b) (0.9 g, 4 mmol) in THF (10 mL) was added DHP (1 g, 12 mmol) and TsOH (100 mg, 0.58 mmol). The mixture was stirred at 5° C. for 4 h. The solvent was removed in vacuo. The residue was purified by flash chromatography on silica gel (PE/EtOAc=20/1) to afford the title compound (1.09 g, yield: 88%) as colorless oil. LCMS (ESI) calc'd for $C_{12}H_{14}BrClO_2$ [M+H]$^+$: 305. found: 305.

iii). Preparation of 1-(3-chloro-2-(((tetrahydro-2H-pyran-2-yl)oxy)methyl)phenyl)cyclo butanol (i-8d)

To a solution of 2-((2-bromo-6-chlorobenzyl)oxy)tetrahydro-2H-pyran (i-8c) (1.1 g, 3.5 mmol) in THF (15 mL)

was added dropwise n-BuLi (2.2 mL, 5.3 mmol) at −70° C. The mixture was stirred at −70° C. for 0.5 h. Cyclobutanone (300 mg, 4.3 mmol) in THF (5 mL) was added via syringe at −70° C. The mixture was stirred at −70° C. for 1 h. Water (10 mL) was added at −30° C. The mixture was concentrated in vacuo, and the residue was partitioned between water (10 mL) and DCM (10 mL). The organic layer was dried over Na$_2$SO$_4$ and evaporated under reduced pressure. The residue was purified by flash chromatography on silica gel (PE/EtOAc=20/1) to afford the title compound (750 mg, yield: 71%) as colorless oil. LCMS (ESI) calc'd for C$_{16}$H$_{21}$ClO$_3$ [M+H]$^+$: 297. found: 297.

iv). Preparation of 1-(3-chloro-2-(hydroxymethyl)phenyl)cyclobutanol (i-8e)

To a solution of 1-(3-chloro-2-(((tetrahydro-2H-pyran-2-yl)oxy)methyl)phenyl)cyclobutanol (i-8d) (350 mg, 1.1 mmol) in MeOH (2 mL) and DCM (3 mL) was added TsOH (219 mg, 1.1 mmol). The mixture was stirred at 5° C. for 2 h. The resulting mixture was partitioned between aq. Na$_2$CO$_3$ (aq. sat. 10 mL) and DCM (10 mL). The organic layer was concentrated in vacuo to afford crude product of the title compound (200 mg, yield: 80%) as colorless oil. LCMS (ESI) calc'd for C$_{11}$H$_{13}$ClO$_2$ [M+H]$^+$: 213. found: 213.

v). Preparation of 1-(2-(bromomethyl)-3-chlorophenyl)cyclobutanol (i-8)

To a solution of 1-(3-chloro-2-(hydroxymethyl)phenyl)cyclobutanol (i-8e) (200 mg, 0.94 mmol) in DCM (10 mL) was added NBS (498 mL, 2.8 mmol), PPh$_3$ (756 mg, 2.8 mmol). The mixture was stirred at 5° C. for 2 h. The resulting mixture was concentrated in vacuo. The residue was purified by flash chromatography on silica gel (PE/EtOAc=20/1) to afford the title compound (250 mg, yield: 96%) as colorless oil. LCMS (ESI) calc'd for C$_{11}$H$_{12}$BrClO [M+H]$^+$: 275. found: 275.

Example i-9

Preparation of 1-(2-chloro-6-(trifluoromethyl)benzyl)-4-fluoro-3-iodo-1H-indazole-6-carboxylic acid (i-9)

Scheme i-9

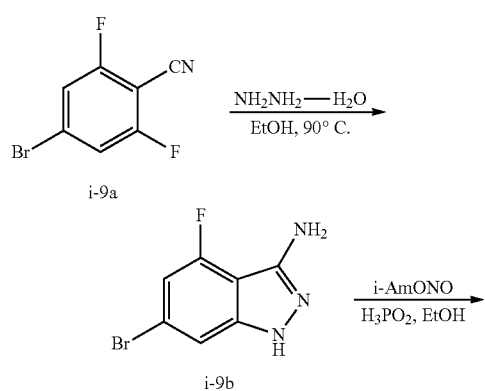

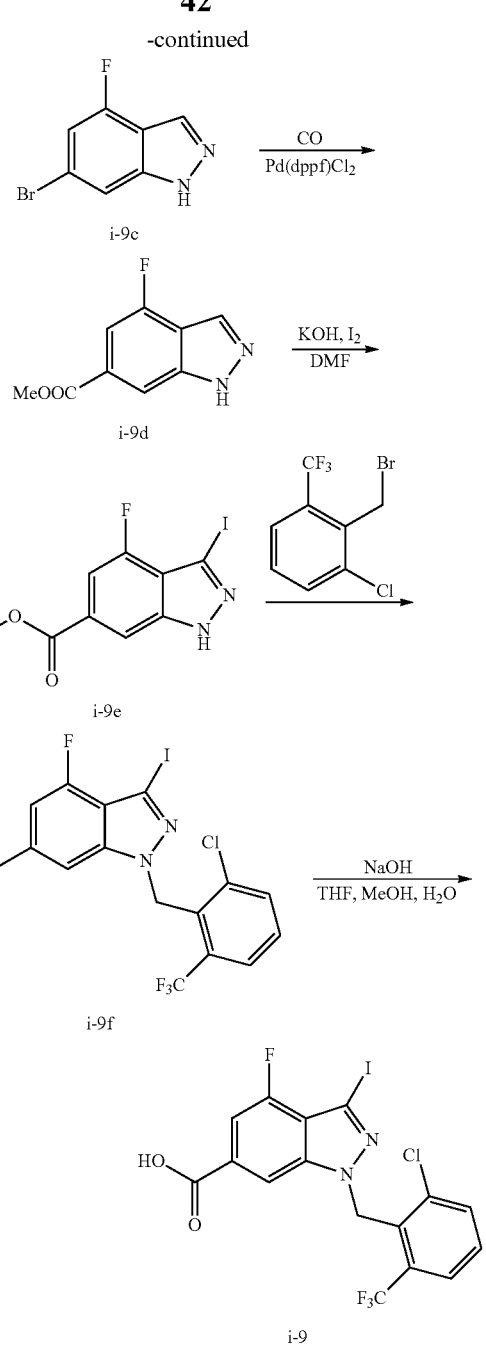

i). Preparation of 6-bromo-4-fluoro-1H-indazol-3-amine (i-9b)

To a solution of 4-bromo-2,6-difluorobenzonitrile (i-9a) (30 g, 138 mmol) in anhydrous ethanol (300 mL) was added dropwise NH$_2$NH$_2$—H$_2$O (27.6 g, 552 mmol) with stirring at room temperature. The reaction mixture was de-gassed under nitrogen and stirred at 90° C. for 2 h. The reaction mixture was cooled to room temperature, diluted with acetone (180 mL) and left to stand overnight. The solid was filtered and washed with DCM to obtain the title compound (30 g, yield: 94%) as a white solid. LCMS (ESI) calc'd for C$_7$H$_5$BrFN$_3$ [M+H]$^+$: 230. found: 230.

ii). Preparation of 6-bromo-4-fluoro-1H-indazole (i-9c)

To a suspension of 6-bromo-4-fluoro-1H-indazol-3-amine (i-9b) (25 g, 108.7 mmol) in anhydrous ethanol (400 mL) was added $H_3PO_2$ (74.4 g, 563.6 mmol) and cooled to 0° C. To the reaction mixture was added isoamyl nitrite (15.24 g, 130.3 mmol), and the mixture was warmed to room temperature and stirred for 2 h. To the resulting brown suspension was added an additional amount of isoamyl nitrite (8 g, 68.3 mmol) and the mixture was stirred at room temperature for 1 h. The reaction mixture was quenched with brine (500 mL) and filtered. The filtrate was extracted with ethyl acetate (500 mL×3). The combined organic layers were dried over anhydrous $MgSO_4$, filtered and concentrated in vacuum. The crude product was purified by column chromatography on silica gel (PE/EtOAc=15/1 to 5/1) to obtain the title compound (9.7 g, yield: 41%) as a yellow solid. LCMS (ESI) calc'd for $C_7H_4BrFN_2$ [M+H]$^+$: 215. found: 215.

iii). Preparation of methyl 4-fluoro-1H-indazole-6-carboxylate (i-9d)

To a solution of 6-bromo-4-fluoro-1H-indazole (i-9c) (6.5 g, 0.03 mol) in 130 mL of methanol were added Pd(dppf)Cl$_2$ (0.37 g, 0.005 mol) and triethylamine (6.15 g, 0.06 mol). Then the mixture was stirred at 70° C. under 50 psi of CO for 16 h. The mixture was filtered and the filtrate was concentrated. The crude residue was purified by column chromatography on silica gel eluted with (PE/EtOAc=5:1) to afford the title compound (2.8 g, yield: 48.3%) as a pale yellow solid. LCMS (ESI) calc'd for $C_9H_7FN_2O_2$ [M+H]$^+$: 195. found: 195.

iv). Preparation of methyl 4-fluoro-3-iodo-1H-indazole-6-carboxylate (i-9e)

To a mixture of methyl 4-fluoro-1H-indazole-6-carboxylate (i-9d) (2.31 g, 11.9 mmol) and KOH (1.33 g, 23.8 mmol) in DMF (40 ml) was added I$_2$ (6 g, 23.8 mmol) portionwise. The mixture was stirred at room temperature for 4 h. The reaction mixture was quenched with saturated Na$_2$SO$_3$ and diluted with water (100 mL), extracted with ethyl acetate (50 mL×3). The combined organic layers were washed with water (50 mL×3), brine (50 mL), dried and concentrated to afford the title compound (3.8 g, 100%) as a yellow solid. LCMS (ESI) calc'd for $C_9H_6FIN_2O_2$ [M+H]$^+$: 321. found: 321.

v). Preparation of methyl 1-(2-chloro-6-(trifluoromethyl)benzyl)-4-fluoro-3-iodo-1H-indazole-6-carboxylate (i-9f)

To a mixture of methyl 4-fluoro-3-iodo-1H-indazole-6-carboxylate (i-9e) (1.5 g, 4.7 mmol) and Cs$_2$CO$_3$ (3.06 g, 9.38 mmol) in 20 mL of anhydrous DMF was added dropwise a solution of 2-chloro-6-(trifluoromethyl)benzyl bromide (1.53 g, 5.63 mmol) in DMF (5 ml) at 0° C. The solution was stirred at room temperature for 1 h. The solution was diluted with H$_2$O until no more solid precipitated out. The solid was collected by filtration and the cake was washed with H$_2$O (5×). The solid was dried in vacuum to afford the title compound (2.8 g, crude) as a yellow solid. LCMS (ESI) calc'd for $C_{17}H_{10}ClF_4IN_2O_2$ [M+H]$^+$: 513. found: 513.

vi). Preparation of 1-(2-chloro-6-(trifluoromethyl)benzyl)-4-fluoro-3-iodo-1H-indazole-6-carboxylic acid (i-9)

To a solution of methyl 1-(2-chloro-6-(trifluoromethyl)benzyl)-4-fluoro-3-iodo-1H-indazole-6-carboxylate (i-9f) (2.8 g, 5.47 mmol) in THF (30 mL) and methanol (10 mL) was added a solution of NaOH (656 mg, 16.4 mmol) in H$_2$O (10 ml). The mixture was stirred at room temperature for 16 h. The solvent was removed under reduced pressure, diluted with H$_2$O (30 mL) and extracted with t-butyl methyl ether (50 mL×2), and the aqueous layers were acidified to pH=4 with aqueous 1M HCl. Solid precipitated out, which was collected by filtration, washed with H$_2$O (5×), and dried in vacuum to afford the title compound (2.7 g, crude) as a yellow solid. LCMS (ESI) calc'd for $C_{16}H_8ClF_4IN_2O_2$ [M+H]$^+$: 499. found: 499.

Example 1A

Preparation of 4-(1-(2-chloro-6-(trifluoromethyl)benzyl)-1H-pyrazolo[3,4-c]pyridin-3-yl)-3-fluorobenzoic acid

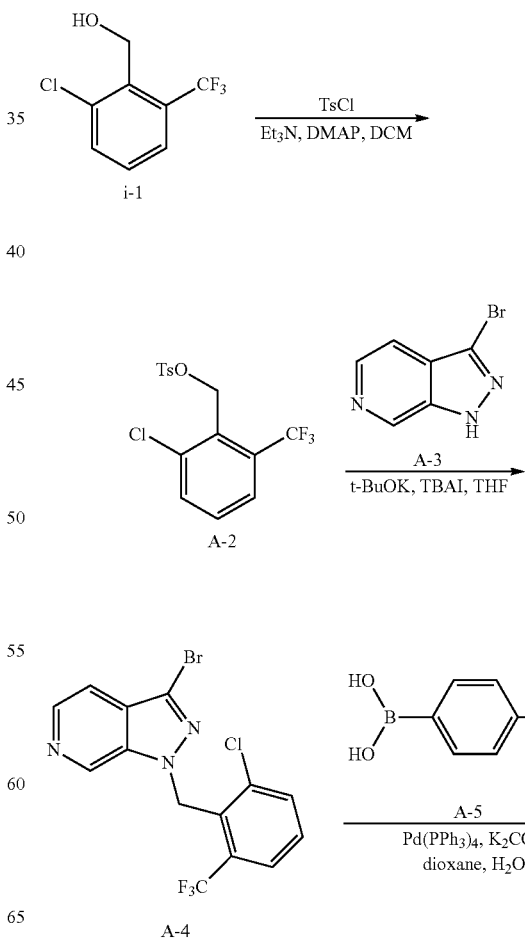

Scheme A

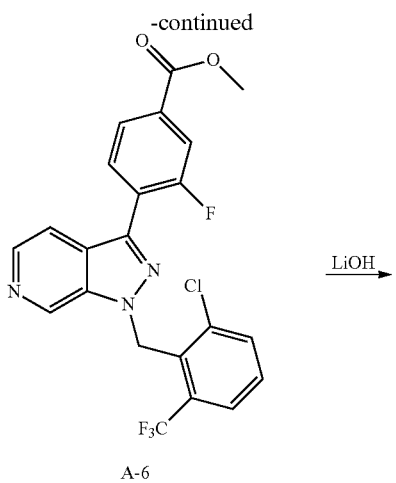

A-6

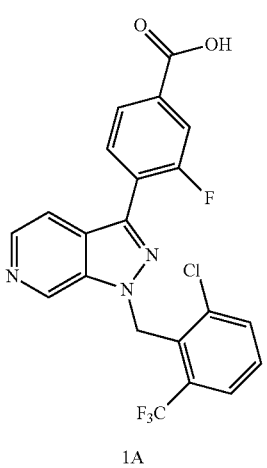

1A i) Preparation of 2-chloro-6-(trifluoromethyl)benzyl 4-methylbenzenesulfonate (A-2)

A mixture of (2-chloro-6-(trifluoromethyl)phenyl)methanol (i-1) (0.35 g, 1.67 mmol), TsCl (0.64 g, 3.34 mmol), DMAP (0.20 g, 1.67 mmol) and Et₃N (0.48 ml, 3.34 mmol) in DCM (10 ml) was stirred at room temperature for 24 h. The resultant mixture was diluted with H₂O (30 ml) and extracted with DCM (20 ml×3). The combined organic layers were washed with 1M HCl solution (10 ml×2), brine (20 ml×1), dried over anhydrous Na₂SO₄ and concentrated to obtain the desired product A-2 as a yellow oil. LCMS (ESI) calc'd for $C_{15}H_{12}ClF_3O_3S$ [M+NH₄]⁺: 382. found: 382.

ii) Preparation of 3-bromo-1-(2-chloro-6-(trifluoromethyl)benzyl)-1H-pyrazolo[4,3-b]pyridine (A-4)

A mixture of 2-chloro-6-(trifluoromethyl)benzyl 4-methylbenzenesulfonate (A-2) (0.19 g, 0.51 mmol), 3-bromo-1H-pyrazolo[3,4-c]pyridine (A-3) (0.1 g, 0.51 mmol), t-BuOK (0.11 g, 1.02 mmol) and TBAI (75 mg, 0.20 mmol) in THF (5 ml) was heated at 60° C. for 14 h. The reaction mixture was cooled down, diluted with saturated NH₄Cl solution (20 ml) and extracted with ethyl acetate (30 ml×2). The combined organic layers were washed with brine (20 ml), dried over anhydrous Na₂SO₄ and concentrated to give the title compound A-4 as a brown oil. LCMS (ESI) calc'd for $C_{14}H_8BrClF_3N_3$ [M+H]⁺: 390. found: 390.

iii) Preparation of methyl 4-(1-(2-chloro-6-(trifluoromethyl)benzyl)-1H-pyrazolo[4,3-b]pyridin-3-yl)-3-fluorobenzoate (A-6)

A mixture of 3-bromo-1-(2-chloro-6-(trifluoromethyl)benzyl)-1H-pyrazolo[4,3-b]pyridine (A-4) (120 mg, 0.31 mmol), 4-(methoxycarbonyl)phenylboronic acid (A-5) (73 mg, 0.37 mmol), Pd(PPh₃)₄ (36 mg, 0.031 mmol) and K₂CO₃ (128 mg, 0.93 mmol) in 1,4-dioxane (5 ml) and H₂O (1 ml) was heated at 110° C. in a microwave reactor for 2 h. The resultant mixture was diluted with H₂O (30 ml) and extracted with ethyl acetate (30 ml×2). The combined organic layers were washed with brine (30 ml), dried over anhydrous Na₂SO₄ and concentrated to give the title compound A-6 as a brown oil. LCMS (ESI) calc'd for $C_{22}H_{14}ClF_4N_3O_2$ [M+H]⁺: 464. found: 464.

iv) Preparation of 4-(1-(2-chloro-6-(trifluoromethyl)benzyl)-1H-pyrazolo[3,4-c]pyridin-3-yl)-3-fluorobenzoic acid (1A)

The mixture of 4-(1-(2-chloro-6-(trifluoromethyl)benzyl)-1H-pyrazolo[4,3-b]pyridine-3-yl)-3-fluoro benzoate (A-6) (100 mg, 0.22 mmol) and LiOH (28 mg, 0.66 mmol) in THF (4 ml) and H₂O (2 ml) was stirred at room temperature for 14 h. The reaction mixture was diluted with H₂O (30 ml) and acidified with 2M HCl to pH=-3. The aqueous layer was extracted with ethyl acetate (20 ml×3). The combined organic layers were washed with brine (20 ml), dried over anhydrous Na₂SO₄ and concentrated. The residue was purified with Prep-HPLC (ACN/H₂O) to give the desired product 1A as a white solid. LCMS (ESI) calc'd for $C_{21}H_{12}ClF_4N_3O_2$ [M+H]⁺: 450. found: 450; ¹HNMR (400 MHz, MeOD) δ 8.63 (1H, d, J=4.4 Hz), 8.20 (1H, d, J=8.8 Hz), 8.05-8.09 (1H, m), 7.94 (1H, d, J=7.6 Hz), 7.79-7.87 (3H, m), 7.62-7.66 (1H, m), 7.52-7.55 (1H, m), 5.97 (2H, s).

Example 1B

Preparation of 4-(1-(2-bromo-6-fluorobenzyl)-1H-pyrazolo[4,3-b]pyridin-3-yl)-3-fluorobenzoic acid (1B)

Scheme B

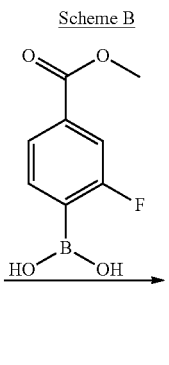

B-1

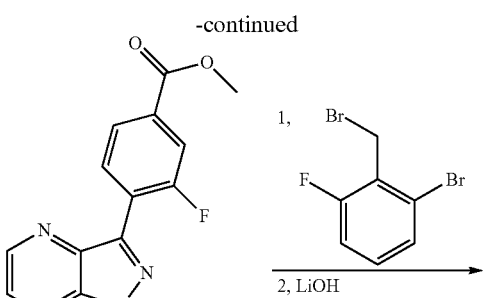

B-2

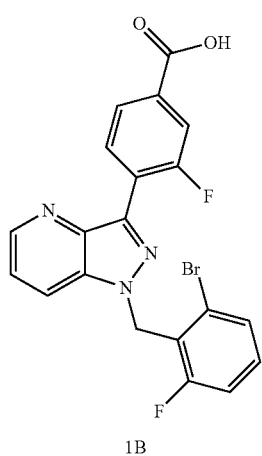

1B i) Preparation of methyl 3-fluoro-4-(1H-pyrazolo[4,3-b]pyridin-3-yl)benzoate (B-2)

A mixture of 3-bromo-1H-pyrazolo[4,3-b]pyridine (B-1) (197 mg, 1.0 mmol), 4-(methoxycarbonyl)phenylboronic acid (198 mg, 1 mmol), Pd(PPh$_3$)$_4$ (115 mg, 0.1 mmol) and K$_2$CO$_3$ (420 mg, 3 mmol) was suspended in 1,4-dioxane (5 ml) and H$_2$O (1 ml). The reaction mixture was heated at 110° C. in a microwave reactor for 2 h. The resultant mixture was diluted with H$_2$O (30 ml) and extracted with ethyl acetate (30 ml×2). The combined organic layers were washed with brine (30 ml), dried over anhydrous Na$_2$SO$_4$ and concentrated to give the title compound B-2 as a brown oil. LCMS (ESI) calc'd for C$_{14}$H$_{10}$FN$_3$O$_2$ [M+H]$^+$: 272.08. found: 272.

ii) Preparation of 4-(1-(2-bromo-6-fluorobenzyl)-1H-pyrazolo[4,3-b]pyridin-3-yl)-3-fluoro benzoic acid (1B)

To a reaction vial was added methyl 3-fluoro-4-(1H-pyrazolo[4,3-b]pyridin-3-yl)benzoate (B-2) (30 mg, 0.11 mmol), 1-bromo-2-(bromomethyl)-3-fluorobenzene (29.4 mg, 0.111 mmol), cesium carbonate (72 mg, 0.22 mmol), and DMF (1 ml). The reaction mixture was stirred at room temperature for 14 h. The mixture was concentrated under reduced pressure. THF (0.5 ml), methanol (0.25 ml), and LiOH (1M, 0.332 mmol) were added and the reaction mixture stirred at room temperature for 14 h. The mixture was evaporated under reduced pressure. The residue was diluted with DMSO (2 ml), filtered, and purified by purified with Prep-HPLC (ACN/H$_2$O) to give the title compound. LCMS (ESI) calc'd for C$_{21}$H$_{12}$ClF$_4$N$_3$O$_2$ [M+H]$^+$: 444. found: 444.

The following examples shown in TABLE 1 were prepared following similar procedures described for Examples #1A, 1B in Schemes A, B. which can be achieved by those of ordinary skill in the art of organic synthesis in light of the present disclosure.

TABLE 1

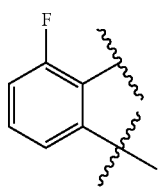

| | Chemical Name | A ring | P | Q | LCMS [M + H]$^+$ Found |
|---|---|---|---|---|---|
| 1C | 4-(1-(2-chloro-6-(trifluoromethyl)benzyl)-4-fluoro-1H-indazol-3-yl)-3-fluorobenzoic acid | 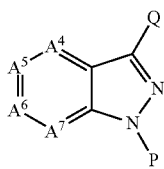 | 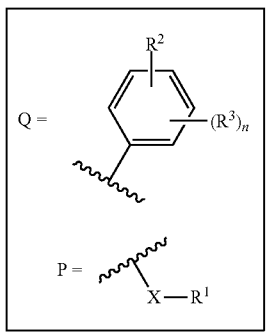 | 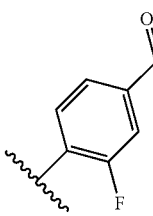 | 467 |

TABLE 1-continued

| | Chemical Name | A ring | P | Q | LCMS [M + H]+ Found |
|---|---|---|---|---|---|
| 1D | 4-(1-(2-chloro-6-(trifluoromethyl)benzyl)-4-fluoro-1H-indazol-3-yl)benzoic acid | 2-fluorophenyl | 2-chloro-6-(trifluoromethyl)benzyl | benzoic acid | 449 |
| 1E | 4-(1-(2-chloro-6-(trifluoromethyl)benzyl)-4-fluoro-1H-indazol-3-yl)-2,5-difluorobenzoic acid | 2-fluorophenyl | 2-chloro-6-(trifluoromethyl)benzyl | 2,5-difluorobenzoic acid | 485 |
| 1F | 4-(1-(1-(2-chloro-6-(trifluoromethyl)phenyl)ethyl)-4-fluoro-1H-indazol-3-yl)-3-fluorobenzoic acid | 2-fluorophenyl | 1-(2-chloro-6-(trifluoromethyl)phenyl)ethyl | 3-fluorobenzoic acid | 481 |
| 1G | (R)-4-(1-(1-(2-chloro-6-(trifluoromethyl)phenyl)ethyl)-4-fluoro-1H-indazol-3-yl)-3-fluorobenzoic acid | 2-fluorophenyl | (R)-1-(2-chloro-6-(trifluoromethyl)phenyl)ethyl | 3-fluorobenzoic acid | 481 |
| 1H | (S)-4-(1-(1-(2-chloro-6-(trifluoromethyl)phenyl)ethyl)-4-fluoro-1H-indazol-3-yl)-3-fluorobenzoic acid | 2-fluorophenyl | (S)-1-(2-chloro-6-(trifluoromethyl)phenyl)ethyl | 3-fluorobenzoic acid | 481 |

TABLE 1-continued

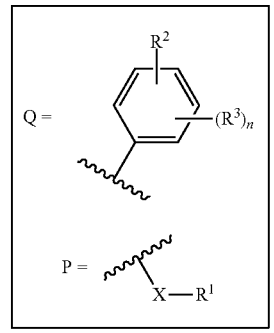

| | Chemical Name | A ring | P | Q | LCMS [M + H]+ Found |
|---|---|---|---|---|---|
| 1I | 4-[1-(2-bromo-3-fluorobenzyl)-1-H-pyrazolo[4,3-b]pyridin-3-yl]-3-fluorobenzoic acid | pyridine | 2-bromo-3-fluorobenzyl | 3-fluoro-4-benzoic acid | 444 |
| 1J | 4-[1-(5-chloro-2-cyanobenzyl)-1H-pyrazolo[4,3-b]pyridin-3-yl]-3-fluorobenzoic acid | pyridine | 5-chloro-2-cyanobenzyl | 3-fluoro-4-benzoic acid | 407 |
| 1K | 3-fluoro-4-(1-{1-[2-(trifluoromethyl)phenyl]ethyl}-1H-pyrazolo[4,3-b]pyridin-3-yl)benzoic acid | pyridine | 1-[2-(trifluoromethyl)phenyl]ethyl | 3-fluoro-4-benzoic acid | 430 |
| 1L | 4-[1-(6-chloro-2-fluoro-3-methylbenzyl)-1H-pyrazolo[4,3-b]pyridin-3-yl]-3-fluorobenzoic acid | pyridine | 6-chloro-2-fluoro-3-methylbenzyl | 3-fluoro-4-benzoic acid | 414 |
| 1M | 4-[1-(2-chloro-3,6-difluorobenzyl)-1H-pyrazolo[4,3-b]pyridin-3-yl]-3-fluorobenzoic acid | pyridine | 2-chloro-3,6-difluorobenzyl | 3-fluoro-4-benzoic acid | 418 |

TABLE 1-continued

| | Chemical Name | A ring | P | Q | LCMS [M + H]+ Found |
|---|---|---|---|---|---|
| 1N | 3-fluoro-4-[1-(2,3,6-trifluorobenzyl)-1H-pyrazolo[4,3-b]pyridin-3-yl]benzoic acid | | | | 402 |
| 1O | 3-fluoro-4-{1-[2-fluoro-6-(trifluoromethyl)benzyl]-1H-pyrazolo[4,3-b]pyridin-3-yl}benzoic acid | | | | 434 |
| 1P | 4-[1-(2,6-difluorobenzyl)-1H-pyrazolo[4,3-b]pyridin-3-yl]-3-fluorobenzoic acid | | | | 384 |
| 1Q | 4-[1-(2-chloro-6-fluorobenzyl)-1H-pyrazolo[4,3-b]pyridin-3-yl]-3-fluorobenzoic acid | | | | 400 |
| 1R | 4-[1-(6-chloro-2-fluoro-3-methoxybenzyl)-1H-pyrazolo[4,3-b]pyridin-3-yl]-3-fluorobenzoic acid | | | | 430 |

TABLE 1-continued

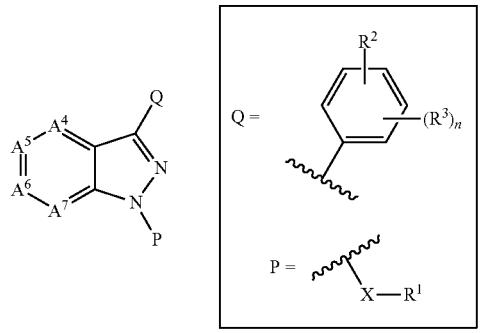

| | Chemical Name | A ring | P | Q | LCMS [M + H]+ Found |
|---|---|---|---|---|---|
| 1S | 4-[1-(2-chloro-6-fluoro-3-methoxybenzyl)-1H-pyrazolo[4,3-b]pyridin-3-yl]-3-fluorobenzoic acid | pyridine | 2-Cl, 3-OMe, 6-F benzyl | 3-F-4-carboxyphenyl | 430 |
| 1T | 4-[1-(2,3-dichloro-6-fluorobenzyl)-1H-pyrazolo[4,3-b]pyridin-3-yl]-3-fluorobenzoic acid | pyridine | 2,3-diCl, 6-F benzyl | 3-F-4-carboxyphenyl | 434 |
| 1U | 4-[1-(1-benzothiophen-7-ylmethyl)-1H-pyrazolo[4,3-b]pyridin-3-yl]-3-fluorobenzoic acid | pyridine | benzothiophen-7-ylmethyl | 3-F-4-carboxyphenyl | 440 |
| 1V | 4-{1-[2,6-dichloro-3-(trifluoromethyl)benzyl]-1H-pyrazolo[4,3-b]pyridin-3-yl}-3-fluorobenzoic acid | pyridine | 2,6-diCl-3-CF3 benzyl | 3-F-4-carboxyphenyl | 484 |
| 1W | 4-[1-(3,6-dichloro-2-fluorobenzyl)-1H-pyrazolo[4,3-b]pyridin-3-yl]-3-fluorobenzoic acid | pyridine | 3,6-diCl-2-F benzyl | 3-F-4-carboxyphenyl | 434 |

TABLE 1-continued
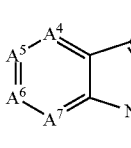
| | Chemical Name | A ring | P | Q | LCMS [M + H]+ Found |
|---|---|---|---|---|---|
| 1X | 4-{1-[2-chloro-6-(methoxycarbonyl)benzyl]-1H-pyrazolo[4,3-b]pyridin-3-yl}-3-fluorobenzoic acid | 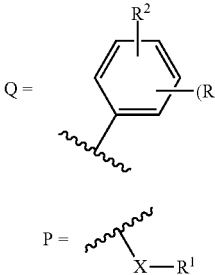 |  | 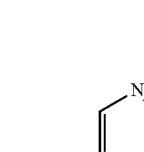 | 440 |
| 1Y | 4-[1-(2-bromo-6-chlorobenzyl)-1H-pyrazolo[4,3-b]pyridin-3-yl]-3-fluorobenzoic acid | 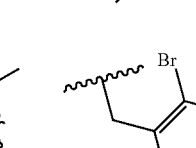 |  | 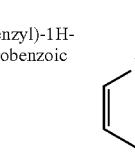 | 460 |
| 1Z | 4-(1-(2-chloro-6-(trifluoromethyl)benzyl)-1H-pyrazolo[4,3-b]pyridin-3-yl)-3-fluorobenzoic acid | 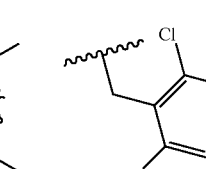 |  | 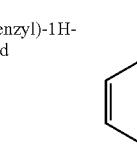 | 450 |
| 1AA | 4-(1-(2-chloro-6-(trifluoromethyl)benzyl)-1H-indazol-3-yl)-2-hydroxybenzoic acid | 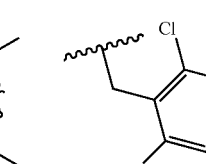 |  | | 447 |

Example 2A

Preparation of 4-(1-(2-chloro-6-(trifluoromethyl)benzyl)-1H-pyrrolo[3,2-b]pyridin-3-yl)-3-fluorobenzoic acid

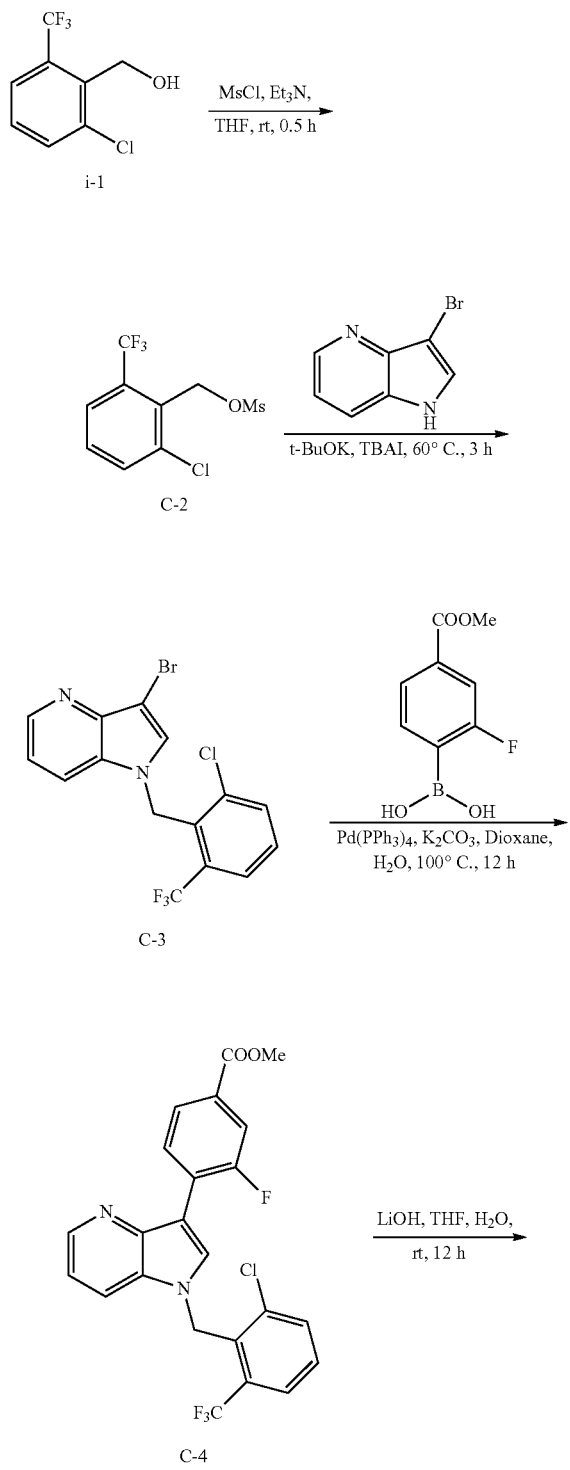

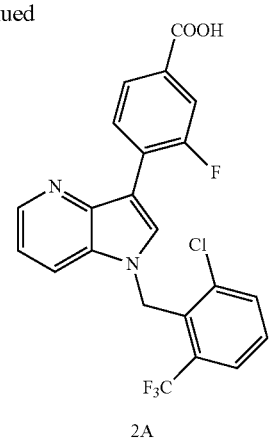

i) Preparation of 2-chloro-6-(trifluoromethyl)benzyl methanesulfonate (C-2)

To a solution of (2-chloro-6-(trifluoromethyl)phenyl)methanol (i-1) (210 mg, 1 mmol) and Et$_3$N (3 ml) in anhydrous THF (10 ml) was added MsCl (228 mg, 2.0 mmol) dropwise. The mixture was stirred at room temperature for 0.5 h. The reaction mixture was filtered and concentrated to afford the title compound C-2 (267 mg, yield: 93%). LCMS (ESI) calc'd [M+H]+: 288.67. found: 288.9.

ii) Preparation of 3-bromo-1-(2-chloro-6-(trifluoromethyl)benzyl)-1H-pyrrolo[3,2-b]pyridine (C-3)

A mixture of 2-chloro-6-(trifluoromethyl)benzyl methanesulfonate (C-2) (288 mg, 1 mmol), 3-bromo-1H-pyrrolo[3,2-b]pyridine (196 mg, 1.0 mmol), t-BuOK (336 mg, 3.0 mmol), TBAI (106 mg, 0.4 mmol), THF (15 ml) was stirred at 60° C. for 3 h. The reaction mixture was filtered, concentrated and purified by column chromatography (EtOAc/PE=1:4) to afford the title compound C-3 (289 mg, yield: 74.5%). LCMS (ESI) calc'd [M+H]$^+$: 389.60. found: 389.8.

iii). Preparation of methyl 4-(1-(2-chloro-6-(trifluoromethyl)benzyl)-1H-pyrrolo[3,2-b]pyridine-3-yl)-3-fluorobenzoate (C-4)

A mixture of 3-bromo-1-(2-chloro-6-(trifluoromethyl)benzyl)-1H-pyrrolo[3,2-b]pyridine (C-3) (216 mg, 1 mmol), 2-fluoro-4-(methoxycarbonyl)phenylboronic acid (298 mg, 1.5 mmol), Pd(PPh$_3$)$_4$ (5 mg), K$_2$CO$_3$ (414 mg, 3.0 mmol) in dioxane (15 ml) and H$_2$O (5 ml) was stirred at 100° C. for 16 h. The reaction mixture was filtered over celite, concentrated and purified by column chromatography (EtOAc/PE=1:4) to afford the title compound C-4 (364 mg, yield: 78.8%). LCMS (ESI) calc'd [M+H]$^+$: 462.86. found: 463.0.

iv). Preparation of 4-(1-(2-chloro-6-(trifluoromethyl)benzyl)-1H-pyrrolo[3,2-b]pyridin-3-yl)-3-fluorobenzoic acid (2A)

To a solution of methyl 4-(1-(2-chloro-6-(trifluoromethyl)benzyl)-1H-pyrrolo[3,2-b]pyridin-3-yl)-3-fluorobenzoate (C-4) (100 mg, 0.21 mmol) in THF (20 ml) and H$_2$O (5 ml) was added LiOH (48 mg, 3.0 mmol). The mixture solution was stirred at room temperature for 16 h, diluted with water (30 ml), and acidified with 2M HC. The mixture was extracted with EA (20 ml×3), dried and concentrated. The residue was purified by prep-HPLC (ACN/H$_2$O) to afford the title compound 2A (79.4 mg, yield: 82.3%). $^1$HNMR (400 MHz, CDCl$_3$) δ: 8.61 (1H, d), 8.52 (1H, d), 8.32 (1H, t), 7.91 (3H, t), 7.82 (1H, 2), 7.70 (2H, m), 7.53 (1H, m), 5.81 (2H, s).

The following example shown in TABLE 2 was prepared following similar procedures described for Example #2A in Scheme C. which can be achieved by those of ordinary skill in the art of organic synthesis in light of the present disclosure.

TABLE 2

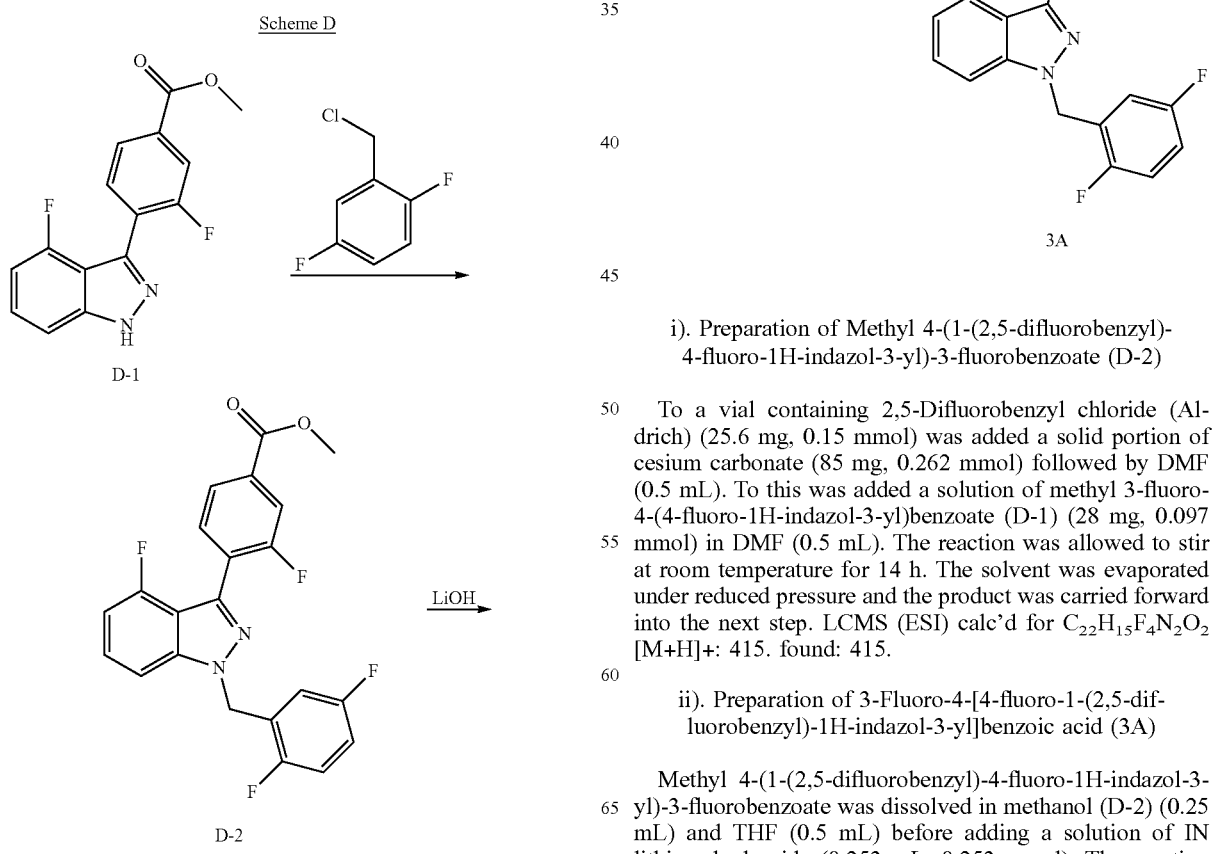

| Chemical Name | A ring | P | Q | LCMS [M + H]+ Found |
|---|---|---|---|---|
| 2B 4-(1-(2-chloro-6-(trifluoromethyl)-benzyl)-1H-pyrrolo[2,3-c]pyridin-3-yl)-3-fluorobenzoic acid | pyridine | 2-chloro-6-(trifluoromethyl)benzyl | 3-fluoro-4-carboxyphenyl | 449 |

Example 3A

Preparation of 3-Fluoro-4-[4-fluoro-1-(2,5-difluorobenzyl)-1H-indazol-3-yl]benzoic acid (3A)

Scheme D i). Preparation of Methyl 4-(1-(2,5-difluorobenzyl)-4-fluoro-1H-indazol-3-yl)-3-fluorobenzoate (D-2)

To a vial containing 2,5-Difluorobenzyl chloride (Aldrich) (25.6 mg, 0.15 mmol) was added a solid portion of cesium carbonate (85 mg, 0.262 mmol) followed by DMF (0.5 mL). To this was added a solution of methyl 3-fluoro-4-(4-fluoro-1H-indazol-3-yl)benzoate (D-1) (28 mg, 0.097 mmol) in DMF (0.5 mL). The reaction was allowed to stir at room temperature for 14 h. The solvent was evaporated under reduced pressure and the product was carried forward into the next step. LCMS (ESI) calc'd for $C_{22}H_{15}F_4N_2O_2$ [M+H]+: 415. found: 415.

ii). Preparation of 3-Fluoro-4-[4-fluoro-1-(2,5-difluorobenzyl)-1H-indazol-3-yl]benzoic acid (3A)

Methyl 4-(1-(2,5-difluorobenzyl)-4-fluoro-1H-indazol-3-yl)-3-fluorobenzoate was dissolved in methanol (D-2) (0.25 mL) and THF (0.5 mL) before adding a solution of 1N lithium hydroxide (0.253 mL, 0.253 mmol). The reaction was allowed to stir at room temperature for 14 h. The solvent was evaporated under reduced pressure. DMSO (1.2 mL) was added to dissolve the crude sample and the material was purified by mass triggered prep-HPLC (CH$_3$CN/H$_2$O) to obtain 15.6 mg (26%) of the title compound. LCMS (ESI) calc'd for C$_{21}$H$_{12}$F$_4$N$_2$O$_2$ [M+H]+: 400. found: 401. 1H NMR (600 MHz, DMSO) δ 7.85 (d, J=7.9, 1H), 7.77 (d, J=10.3, 1H), 7.72 (t, J=7.5, 1H), 7.65 (d, J=8.5, 1H), 7.46 (m, J=8.1, 13.0, 1H), 7.27 (m, J=4.5, 9.2, 1H), 7.19 (m, J=6.4, 10.6, 1H), 7.08 (m, 1H), 6.98 (dd, J=7.8, 10.8, 1H), 5.78 (s, 2H), 2.47 (s, 1H).

The following examples shown in TABLE 3 were prepared following similar procedures described for Example 3A in Scheme D, which can be achieved by those of ordinary skill in the art of organic synthesis in light of the present disclosure.

TABLE 3

| | Chemical Name | Structure | LCMS [M + H]+ Found |
|---|---|---|---|
| 3B | 3-fluoro-4-(4-fluoro-1-(3-(trifluoromethoxy)-benzyl)-1H-indazol-3-yl)benzoic acid | 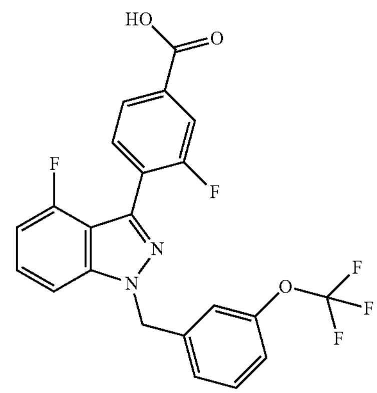 [SMILES: O=C(O)c1ccc(-c2nn(Cc3cccc(OC(F)(F)F)c3)c3cccc(F)c23)c(F)c1] | 449 |
| 3C | 3-fluoro-4-[4-fluoro-1-(2-methoxybenzyl)-1H-indazol-3-yl]benzoic acid | 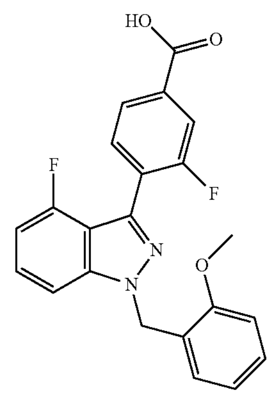 [SMILES: COc1ccccc1Cn1nc(-c2ccc(C(=O)O)cc2F)c2c(F)cccc21] | 395 |
| 3D | 3-fluoro-4-{4-fluoro-1-[2-(1H-pyrazol-1-yl)benzyl]-1H-indazol-3-yl}benzoic acid | 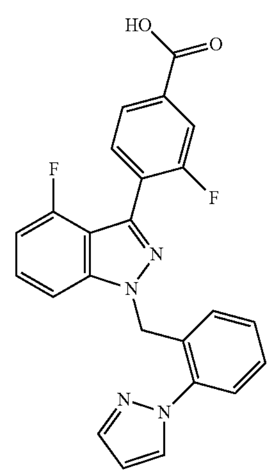 [SMILES: O=C(O)c1ccc(-c2nn(Cc3ccccc3-n3cccn3)c3cccc(F)c23)c(F)c1] | 431 |

TABLE 3-continued

| Chemical Name | Structure | LCMS [M + H]+ Found |
|---|---|---|
| 3E 4-[1-(2-cyanobenzyl)-4-fluoro-1H-indazol-3-yl]-3-fluorobenzoic acid | | 390 |
| 3F 3-fluoro-4-{4-fluoro-1-[2-fluoro-5-(trifluoromethoxy)-benzyl]-1H-indazol-3-yl}benzoic acid | | 467 |
| 3G 4-[1-(2,6-dichlorobenzyl)-4-fluoro-1H-indazol-3-yl]-3-fluorobenzoic acid | | 433 |

TABLE 3-continued

| Chemical Name | Structure | LCMS [M + H]+ Found |
|---|---|---|
| 3H 4-(1-(2,6-dichlorobenzyl)-1H-pyrazolo[4,3-b]pyridin-3-yl)-3-fluorobenzoic acid | 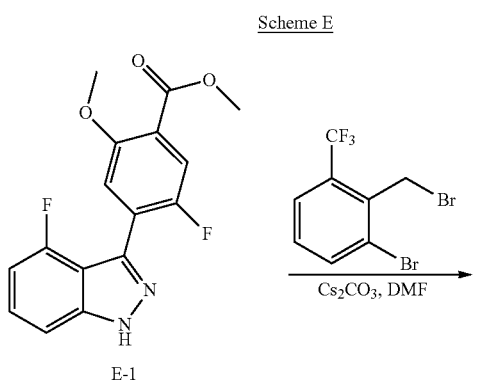 | 416 |

Example 4A

Preparation of 4-(1-(2-bromo-6-(trifluoromethyl)benzyl)-4-fluoro-1H-indazol-3-yl)-5-fluoro-2-hydroxybenzoic acid (4A)

Scheme E i). Preparation of methyl 4-(1-(2-bromo-6-(trifluoromethyl)benzyl)-4-fluoro-1H-indazol-3-yl)-5-fluoro-2-methoxybenzoate (E-2)

To a solution of methyl 5-fluoro-4-(4-fluoro-1H-indazol-3-yl)-2-methoxybenzoate (E-1) (954 mg, 3 mmol) in DMF (10 mL) was added 1-bromo-2-(bromomethyl)-3-(trifluoromethyl)benzene (1 g, 3.14 mmol) and $Cs_2CO_3$ (1.96 g, 6 mmol). The mixture was stirred at 10° C. for 3 h. The solvent was removed in vacuo, and the residue was partitioned between water (15 mL) and DCM (15 mL). The aqueous phase was extracted with DCM (15 mL×3). The combined organic phase was dried over anhydrous $Na_2SO_4$ and evaporated under reduced pressure. The residue was purified by column chromatography on silica gel (PE/EtOAc=50/1) to afford the title compound (800 mg, yield: 48%). LCMS (ESI) calc'd for $C_{24}H_{16}BrF_5N_2O_3$ [M+H]+: 555. found: 555.

ii). Preparation of 4-(1-(2-bromo-6-(trifluoromethyl)benzyl)-4-fluoro-1H-indazol-3-yl)-5-fluoro-2-hydroxybenzoic acid (4A)

To a solution of methyl 4-(1-(2-bromo-6-(trifluoromethyl)benzyl)-4-fluoro-1H-indazol-3-yl)-5-fluoro-2- methoxybenzoate (E-2) (80 mg, 0.14 mmol) in DCM (2 mL) was added BBr$_3$ (0.14 mL, 1.4 mmol) at −30° C. The mixture was stirred at 10° C. for 16 h. The resulting mixture was concentrated in vacuo. The residue was purified by prep-HPLC (acetonitrile+0.75%0 trifluoroacetic acid in water) to afford the title compound (30 mg, yield: 39.5%) as a white solid. LCMS (ESI): calc'd for C$_{22}$H$_{12}$BrF$_5$N$_2$O$_3$ [M+H]$^+$: 527. found: 527; $^1$H NMR (400 MHz, CDCl$_3$) δ 7.98 (1H, d, J=8.0 Hz), 7.88 (1H, d, J=8.0 Hz), 7.62 (1H, d, J=10.0 Hz), 7.44-7.56 (3H, m), 6.99 (1H, d, J=6.0 Hz), 6.92 (1H, dd, J=10.6, 7.6 Hz), 5.88 (2H, s), 3.37 (1H, s).

The following examples shown in TABLE 4 were prepared following similar procedures described for Example 4A in Scheme E which can be achieved by those of ordinary skill in the art of organic synthesis in light of the present disclosure.

TABLE 4

| Chemical Name | Structure | LCMS [M + H]$^+$ Found |
|---|---|---|
| 4B 4-(1-(2-chloro-6-fluorobenzyl)-4-fluoro-1H-indazol-3-yl)-5-fluoro-2-hydroxybenzoic acid | | 433 |
| 4C 4-(1-benzyl-4-fluoro-1H-indazol-3-yl)-5-fluoro-2-hydroxybenzoic acid | | 381 |
| 4D 4-(1-(2-chloro-5-fluorobenzyl)-4-fluoro-1H-indazol-3-yl)-5-fluoro-2-hydroxybenzoic acid | 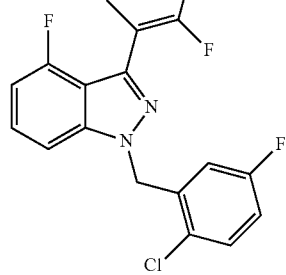 | 433 |
| 4E 4-(1-(2-chloro-4-fluorobenzyl)-4-fluoro-1H-indazol-3-yl)-5-fluoro-2-hydroxybenzoic acid | 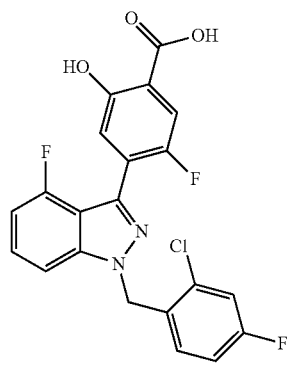 [SMILES: O=C(O)c1cc(F)c(-c2nn(Cc3ccc(F)cc3Cl)c3cccc(F)c23)cc1O] | 433 |
| 4F 4-(1-(2-bromo-5-fluorobenzyl)-4-fluoro-1H-indazol-3-yl)-5-fluoro-2-hydroxybenzoic acid | 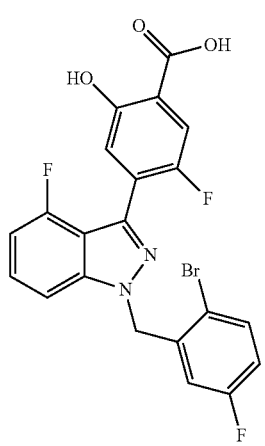 [SMILES: O=C(O)c1cc(F)c(-c2nn(Cc3cc(F)ccc3Br)c3cccc(F)c23)cc1O] | 477 |

TABLE 4-continued

| Chemical Name | Structure | LCMS [M + H]+ Found |
|---|---|---|
| 4G 4-(1-(3-chloro-5-fluorobenzyl)-4-fluoro-1H-indazol-3-yl)-5-fluoro-2-hydroxybenzoic acid | | 433 |
| 4H 4-(1-(3,5-dichlorobenzyl)-4-fluoro-1H-indazol-3-yl)-5-fluoro-2-hydroxybenzoic acid | | 449 |
| 4I 4-(1-(4-bromo-2-fluorobenzyl)-4-fluoro-1H-indazol-3-yl)-5-fluoro-2-hydroxybenzoic acid | | 477 |
| 4J 4-(1-(2,5-dichlorobenzyl)-4-fluoro-1H-indazol-3-yl)-5-fluoro-2-hydroxybenzoic acid | | 449 |
| 4K 5-fluoro-4-(4-fluoro-1-(3-fluoro-5-(trifluoromethyl)benzyl)-1H-indazol-3-yl)-2-hydroxybenzoic acid | | 467 |
| 4L 5-fluoro-4-(4-fluoro-1-(2-fluoro-6-(trifluoromethyl)benzyl)-1H-indazol-3-yl)-2-hydroxybenzoic acid | | 467 |

TABLE 4-continued

| Chemical Name | Structure | LCMS [M + H]+ Found |
|---|---|---|
| 4M 4-(1-(2-chloro-6-(trifluoromethyl)-benzyl)-4-fluoro-1H-indazol-3-yl)-5-fluoro-2-hydroxybenzoic acid | | 483 |

Example 5A

Preparation of 4-(1-(2-chloro-6-cyclopropylbenzyl)-4-fluoro-1H-indazol-3-yl)-5-fluoro-2-hydroxybenzoic acid (5A)

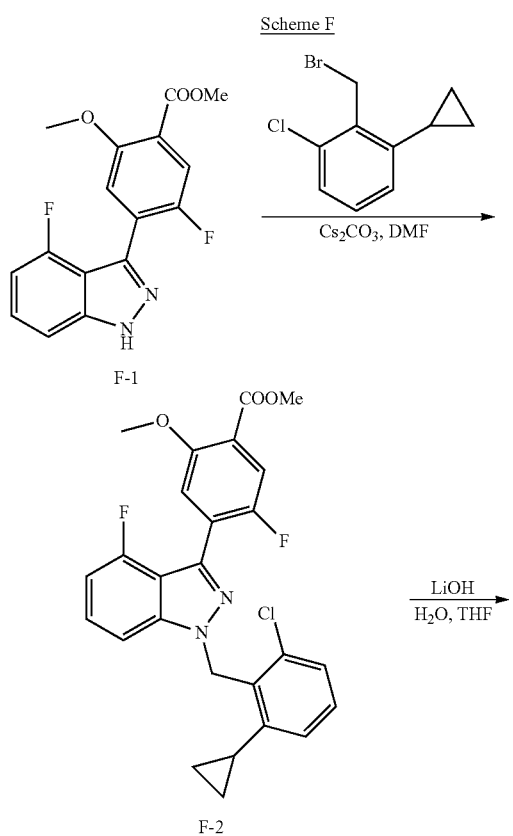

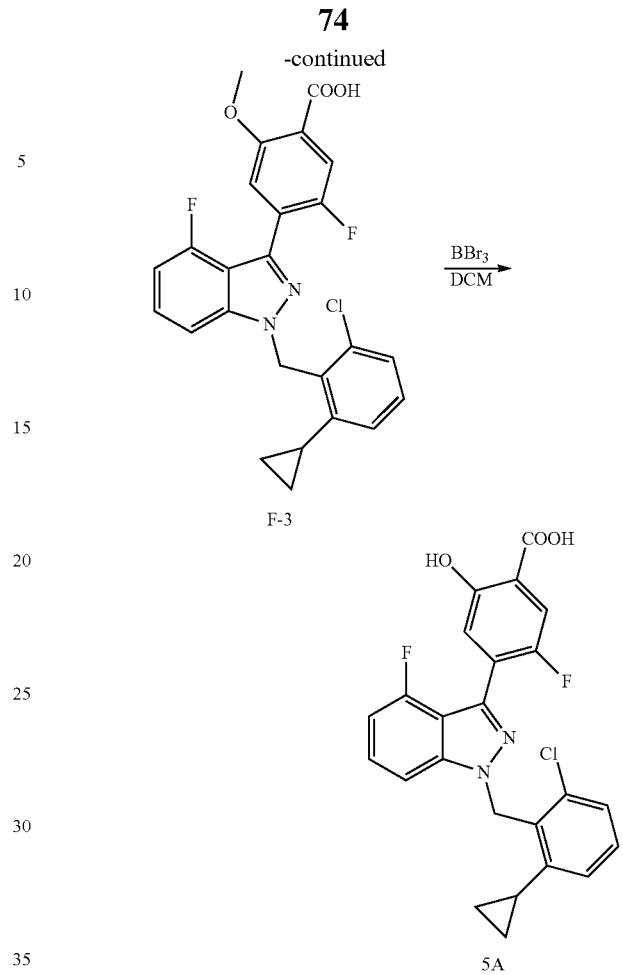

i). Preparation of methyl 4-(1-(2-chloro-6-cyclopropylbenzyl)-4-fluoro-1H-indazol-3-yl)-5-fluoro-2-methoxybenzoate (F-2)

To a solution of methyl 5-fluoro-4-(4-fluoro-1H-indazol-3-yl)-2-methoxybenzoate (F-1) (130 mg, 0.41 mmol) in DMF (2 mL) was added 2-(bromomethyl)-1-chloro-3-cyclopropylbenzene (120 mg, 0.49 mmol) and $Cs_2CO_3$ (267 mg, 0.82 mmol). The mixture was stirred at 10° C. for 2 h. The solvent was removed in vacuo, and the residue was partitioned between water (5 mL) and DCM (5 mL). The aqueous layer was extracted with DCM (5 mL×3). The combined organic layers were dried over anhydrous $Na_2SO_4$ and evaporated in vacuo. The residue was purified by prep-TLC (PE/EtOAc=5/1) to afford the title compound (80 mg, yield: 41%). LCMS (ESI) calc'd for $C_{10}H_{10}BrCl$ [M+H]+: 483. found: 483.

ii). Preparation of 4-(1-(2-chloro-6-cyclopropylbenzyl)-4-fluoro-1H-indazol-3-yl)-5-fluoro-2-methoxybenzoic acid (F-3)

To a solution of 4-(1-(2-chloro-6-cyclopropylbenzyl)-4-fluoro-1H-indazol-3-yl)-5-fluoro-2-methoxybenzoic acid (F-2) (80 mg, 0.17 mmol) in THF (2 mL) was added LiOH (38 mg, 1.6 mmol) and water (1 mL). The mixture was stirred at 10° C. for 16 h. The solvent was removed in vacuo, and the residue was partitioned between water (10 mL) and DCM (10 mL). The organic layer was dried over anhydrous Na$_2$SO$_4$ and concentrated in vacuo. The residue was purified by Prep-TLC (PE/EtOAc=5/1) to afford the title compound (60 mg, yield: 77%). LCMS (ESI) calc'd for C$_{25}$H$_{19}$ClF$_2$N$_2$O$_3$ [M+H]$^+$: 469. found: 469.

iii). Preparation of 4-(1-(2-chloro-6-cyclopropylbenzyl)-4-fluoro-1H-indazol-3-yl)-5-fluoro-2-hydroxybenzoic acid (5A)

To a solution of 4-(1-(2-chloro-6-cyclopropylbenzyl)-4-fluoro-1H-indazol-3-yl)-5-fluoro-2-methoxybenzoic acid (F-3) (60 mg, 0.13 mmol) in DCM (2 mL) was added BBr$_3$ (0.12 mL, 1.2 mmol) at –70° C. The mixture was stirred at –70° C. for 2 h, warmed to –30° C. and adjusted to pH=8 with saturated aq. NaHCO$_3$. The resulting mixture was partitioned between water (10 mL) and DCM (10 mL). The organic layer was dried over anhydrous Na$_2$SO$_4$ and concentrated in vacuo. The residue was purified by prep-HPLC (acetonitrile+0.75%0 trifluoroacetic acid in water) to afford the title compound (10 mg, yield: 17.2%) as a brown solid. LCMS (ESI) calc'd for C$_{25}$H$_{19}$ClF$_2$N$_2$O$_3$ [M+H]$^+$: 455. found: 455; $^1$H NMR (400 MHz, CD$_3$OD) δ 7.64 (1H, d, J=9.6 Hz), 7.33-7.41 (3H, m), 7.27-7.32 (1H, m), 7.10 (1H, d, J=7.53 Hz), 6.99 (1H, d, J=5.52 Hz), 6.83-6.88 (1H, m), 6.05 (2H, s), 2.09-2.14 (1H, m), 0.82-0.87 (2H, m), 0.60-0.67 (2H, m).

Example 6A

Preparation of 4-(1-(2-chloro-6-methylbenzyl)-4-fluoro-1H-indazol-3-yl)-5-fluoro-2-hydroxybenzoic acid (6A)

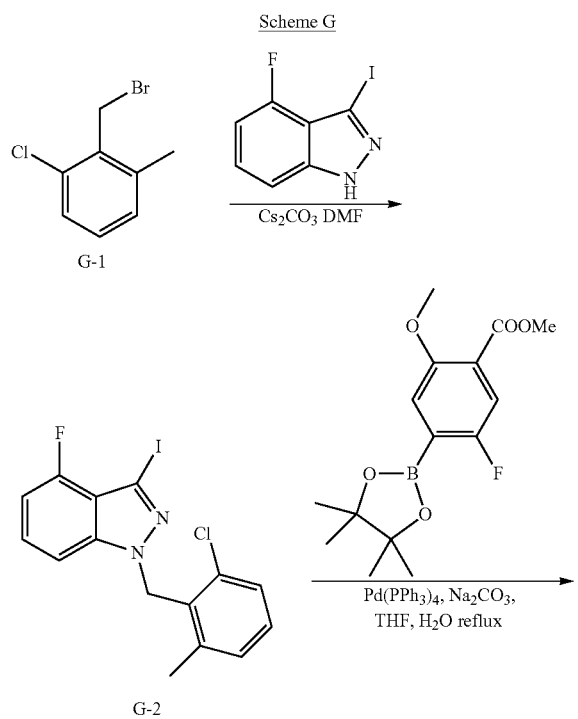

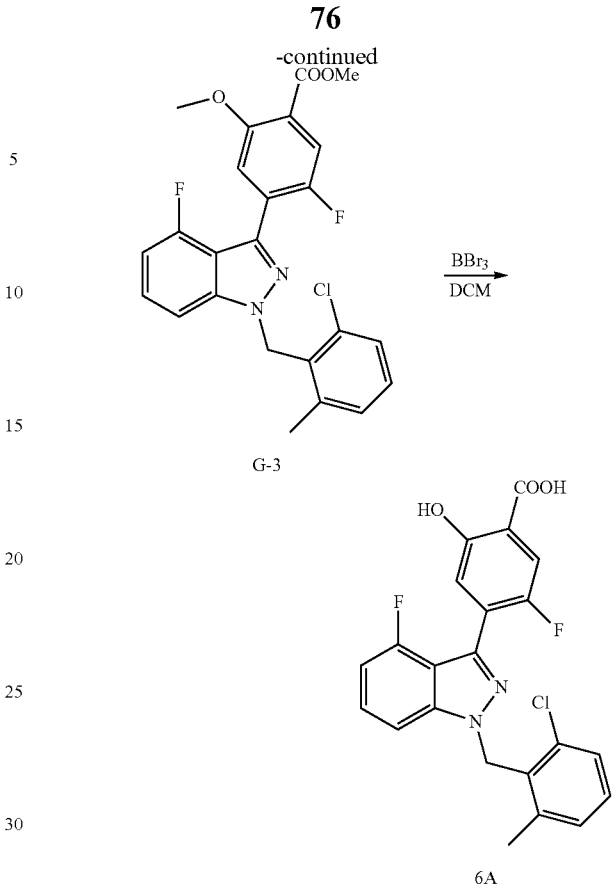

i). Preparation of 1-(2-chloro-6-methylbenzyl)-4-fluoro-3-iodo-1H-indazole (G-2)

To a solution of 2-(bromomethyl)-1-chloro-3-methylbenzene (G-1) (400 mg, 1.5 mmol) in 5 mL of DMF was added Cs$_2$CO$_3$ (960 mg, 3 mmol). The mixture was stirred at 0° C. for 10 min, and then 4-fluoro-3-iodo-1H-indazole (436 mg, 2 mmol) was added. The mixture was stirred at room temperature for 1 hour. The resulting mixture was diluted with water (25 mL) and extracted with EtOAc (15 mL×3). The combined organic layers were washed with brine (20 mL), dried over anhydrous Na$_2$SO$_4$ and concentrated in vacuo. The crude product was purified by column chromatography on silica gel (PE/EtOAc=20/1) to give the title compound (300 mg, yield: 45%). LCMS (ESI) calc'd for C$_{15}$H$_{11}$ClFIN$_2$ [M+H]$^+$: 400. found: 400.

ii). Preparation of methyl 4-(1-(2-chloro-6-methylbenzyl)-4-fluoro-1H-indazol-3-yl)-5-fluoro-2-methoxybenzoate (G-3)

To a solution of 1-(2-chloro-6-methylbenzyl)-4-fluoro-3-iodo-1H-indazole (G-2) (300 mg, 0.75 mmol) in 10 mL of THF/H$_2$O (4/1) was added methyl 5-fluoro-2-methoxy-4-(4,4,5,5-tetramethyl-1,3,2-dioxaborolan-2-yl)benzoate (310 mg, 1 mmol), sodium carbonate (530 mg, 5 mmol). The mixture was degassed with N$_2$, and Pd(PPh$_3$)$_4$ (100 mg, 0.1 mmol) was added in one portion. After this addition, the mixture was stirred at reflux under N$_2$ for 3 h. The resulting mixture was diluted with water (10 mL), and extracted with EtOAc (30 mL×3). The combined organic layers were concentrated in vacuo and the residue was purified by column chromatography on silica gel (PE/EtOAc=10/1) to afford the title compound (80 mg, yield: 23%). LCMS (ESI) calc'd for $C_{24}H_{19}ClF_2N_2O_3$ [M+H]$^+$: 457. found: 457.

iii). Preparation of 4-(1-(2-chloro-6-methylbenzyl)-4-fluoro-1H-indazol-3-yl)-5-fluoro-2-hydroxybenzoic acid (6A)

To a solution of methyl 4-(1-(2-chloro-6-methylbenzyl)-4-fluoro-1H-indazol-3-yl)-5-fluoro-2-methoxybenzoate (G-3) (80 mg, 0.02 mmol) in 5 mL of dry DCM was added dropwise BBr$_3$ (150 mg, 0.6 mmol) at −30° C., then the mixture was stirred at room temperature for 18 hours. The resulting mixture was quenched with MeOH (10 mL), and concentrated in vacuo. The residue was purified by prep-HPLC (acetonitrile+0.75%0 trifluoroacetic acid in water) to afford the title compound (25 mg, 33%). LCMS (ESI) calc'd for $C_{25}H_{19}ClF_2N_2O_3$ [M+H]$^+$: 429. found: 429; $^1$H NMR (400 MHz, CD$_3$OD) δ 7.64 (1H, d, J=10.04 Hz), 7.37-7.47 (2H, m), 7.34 (1H, d, J=7.53 Hz), 7.20-7.30 (2H, m), 7.09 (1H, d, J=5.52 Hz), 6.88 (1H, dd, J=10.29, 7.28 Hz), 5.84 (2H, s), 2.43 (3H, s).

Example 7A

Preparation of 4-(1-(2-chloro-6-(1-hydroxycyclobutyl)benzyl)-4-fluoro-1H-indazol-3-yl)-3-fluorobenzoic acid (7A)

Scheme H

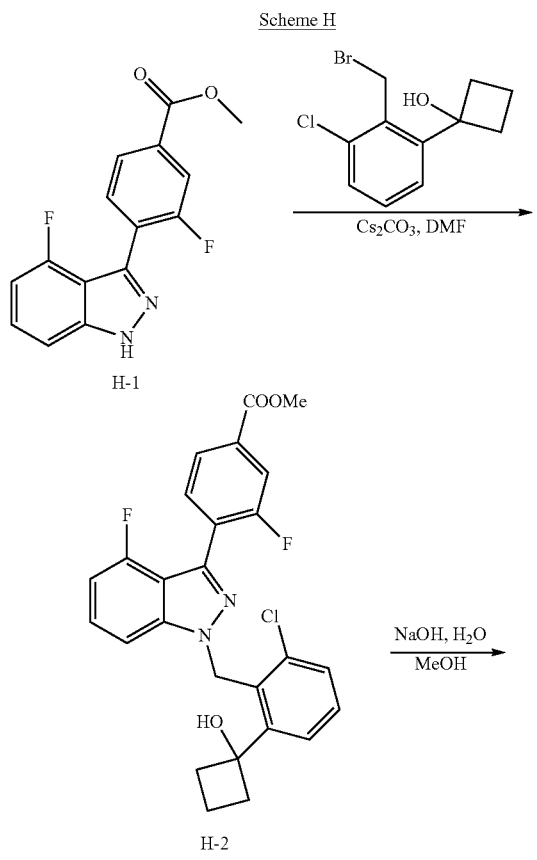

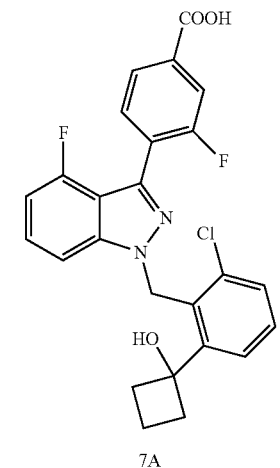

7A i). Preparation of methyl 4-(1-(2-chloro-6-(1-hydroxycyclobutyl)benzyl)-4-fluoro-1H-indazol-3-yl)-3-fluorobenzoate (H-2)

To a solution of c methyl 3-fluoro-4-(4-fluoro-1H-indazol-3-yl)benzoate (H-1) (30 mg, 0.1 mmol) and 1-(2-(bromomethyl)-3-chlorophenyl)cyclobutanol (33 mg, 0.12 mmol) in DMF (2 mL) was added Cs$_2$CO$_3$ (65 mg, 0.2 mmol). The mixture was stirred at 5° C. for 2 h. The solvent was removed in vacuo, and the residue was purified by prep-TLC (PE/EtOAc=5/1) to give the title compound (15 mg, yield: 30%) as a brown solid. LCMS (ESI) calc'd for $C_{26}H_{21}ClF_2N_2O_3$ [M+H]$^+$: 483. found: 483.

ii). Preparation of 4-(1-(2-chloro-6-(1-hydroxycyclobutyl)benzyl)-4-fluoro-1H-indazol-3-yl)-3-fluorobenzoic acid (7A)

To a solution of methyl 4-(1-(2-chloro-6-(1-hydroxycyclobutyl)benzyl)-4-fluoro-1H-indazol-3-yl)-3-fluorobenzoate (H-2) (15 mg, 0.03 mmol) in MeOH (2 mL) was added a solution of NaOH (24 mg, 0.6 mmol) in water (0.5 mL) at 5° C. The mixture was stirred at 40° C. for 16 h. The resulting mixture was concentrated in vacuo, and the residue was purified by prep-HPLC (acetonitrile+0.75%0 trifluoroacetic acid in water) to afford the title compound (2 mg, yield: 13.6%) as a brown solid. LCMS (ESI) calc'd for $C_{25}H_{19}ClF_2N_2O_3$ [M+H]$^+$: 469. found: 469; $^1$H NMR (400 MHz, CD$_3$OD) δ 7.90 (1H, d, J=8.0 Hz), 7.81 (1H, d, J=10.5 Hz), 7.63 (1H, t, J=7.3 Hz), 7.56-7.34 (5H, m), 6.90 (1H, dd, J=7.8, 10.8 Hz), 5.90 (2H, s), 3.37 (1H, br s), 2.87-2.77 (2H, m), 2.48-2.37 (2H, m), 2.22-2.12 (1H, m), 1.80-1.69 (1H, m).

Example 8A & 8B

Preparation of 5-fluoro-4-(4-fluoro-1-(2-methyl-6-(trifluoromethyl)benzyl)-1H-indazol-3-yl)-2-hydroxybenzoic acid (8A) and 5-fluoro-4-(4-fluoro-1-(2-(trifluoromethyl)benzyl)-1H-indazol-3-yl)-2-hydroxybenzoic acid (8B)

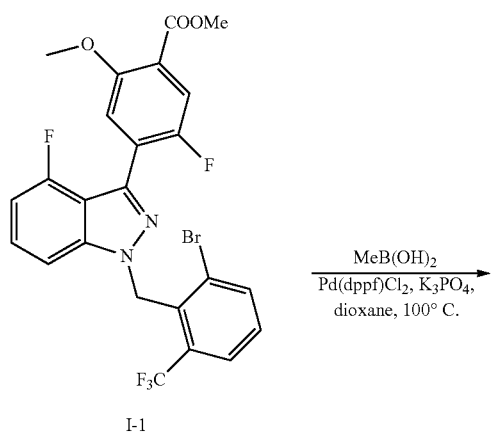

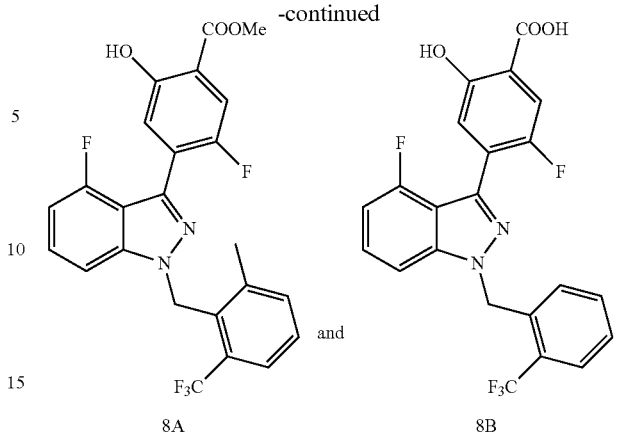

i). Preparation of methyl 5-fluoro-4-(4-fluoro-1-(2-methyl-6-(trifluoromethyl)benzyl)-1H-indazol-3-yl)-2-methoxybenzoate (I-2) and methyl 5-fluoro-4-(4-fluoro-1-(2-(trifluoromethyl)benzyl)-1H-indazol-3-yl)-2-methoxybenzoate (I-3)

To a solution of methyl 4-(1-(2-bromo-6-(trifluoromethyl)benzyl)-4-fluoro-1H-indazol-3-yl)-5-fluoro-2-methoxybenzoate (I-1) (100 mg, 0.18 mmol) in 1,4-dioxane (3 mL) and $H_2O$ (0.5 mL) was added $MeB(OH)_2$ (41 mg, 0.9 mmol), $K_3PO_4$ (153 mg, 0.72 mmol), $Pd(dppf)Cl_2$ (5 mg). The mixture was stirred at 100° C. for 16 h. The solvent was removed in vacuo, and the residue was purified by prep-TLC (PE/EtOAc=5/1) to give methyl 5-fluoro-4-(4-fluoro-1-(2-methyl-6-(trifluoromethyl)benzyl)-1H-indazol-3-yl)-2-methoxybenzoate (I-2) (40 mg, yield: 45%) and methyl 5-fluoro-4-(4-fluoro-1-(2-(trifluoromethyl)benzyl)-1H-indazol-3-yl)-2-methoxybenzoate (I-3) (10 mg, yield: 12%) as white solids.

I-1: LCMS (ESI) calc'd for $C_{25}H_{19}F_5N_2O_3$ [M+H]$^+$: 491. found: 491.

I-2: LCMS (ESI) calc'd for $C_{24}H_{17}F_5N_2O_3$ [M+H]$^+$: 477. found: 477.

ii). Preparation of 5-fluoro-4-(4-fluoro-1-(2-methyl-6-(trifluoromethyl)benzyl)-1H-indazol-3-yl)-2-hydroxylbenzoic acid (8A)

To a solution of methyl 5-fluoro-4-(4-fluoro-1-(2-methyl-6-(trifluoromethyl)benzyl)-1H-indazol-3-yl)-2-methoxybenzoate (I-2) (40 mg, 0.08 mmol) in DCM (2 mL) was added $BBr_3$ (0.12 mL, 1.2 mmol) at −30° C. The mixture was stirred at 10° C. for 16 h. The resulting mixture was concentrated in vacuo. The residue was purified by prep-HPLC (acetonitrile+0.75%0 trifluoroacetic acid in water) to afford the title compound (7 mg, yield: 18.9%) as a white solid. LCMS (ESI) calc'd for $C_{23}H_{15}F_5N_2O_3$ [M+H]$^+$: 463. found: 463; $^1$H NMR (400 MHz, CDCl$_3$) δ 7.68 (1H, d, J=8.0 Hz), 7.62 (1H, d, J=8.0 Hz), 7.45-7.52 (2H, m), 7.36-7.41 (1H, m), 7.31 (1H, d, J=8.0 Hz), 7.01 (1H, d, J=5.6 Hz), 6.85-6.90 (1H, m), 5.79 (2H, s), 2.2 (3H, s). MS (ESI) m/z: 463 (M+H$^+$).

5-fluoro-4-(4-fluoro-1-(2-(trifluoromethyl)benzyl)-1H-indazol-3-yl)-2-hydroxybenzoic acid (8B) was prepared following a similar procedure to that described above, which can be achieved by those of ordinary skill in the art of organic synthesis in light of the present disclosure.

Example 9A

Preparation of 4-(1-(2-ethyl-6-(trifluoromethyl)benzyl)-4-fluoro-1H-indazol-3-yl)-5-fluoro-2-hydroxybenzoic acid (9A)

Scheme J

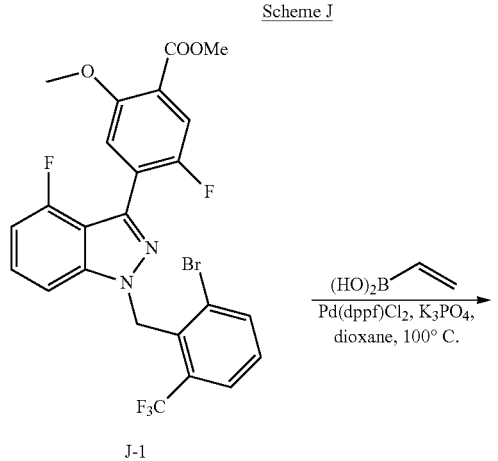

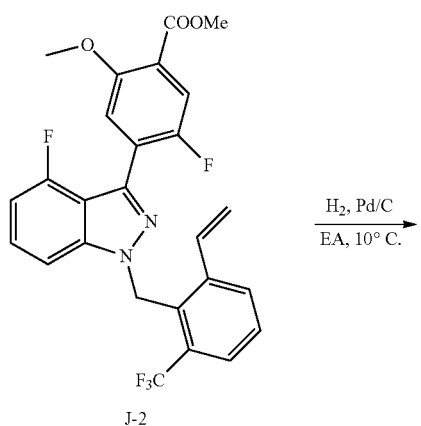

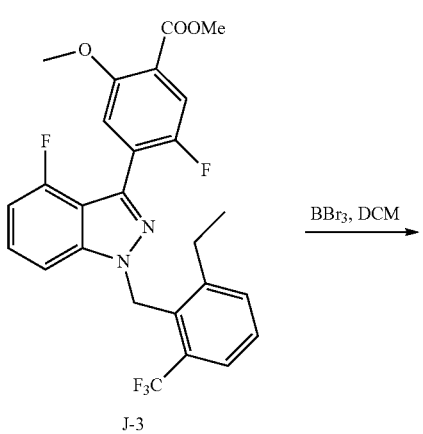

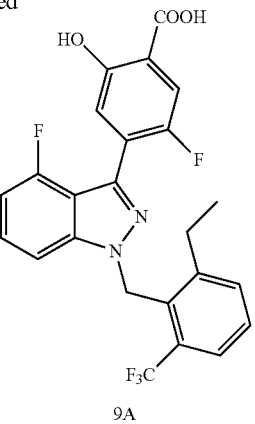

9A i). Preparation of methyl 5-fluoro-4-(4-fluoro-1-(2-(trifluoromethyl)-6-vinylbenzyl)-1H-indazol-3-yl)-2-methoxybenzoate (J-2)

To a solution of methyl 4-(1-(2-bromo-6-(trifluoromethyl)benzyl)-4-fluoro-1H-indazol-3-yl)-5-fluoro-2-methoxybenzoate (J-1) (100 mg, 0.18 mmol) in 1,4-dioxane (3 mL) and H$_2$O (0.5 mL) was added vinylboronic acid (41 mg, 0.9 mmol), K$_3$PO$_4$ (153 mg, 0.72 mmol) and Pd(dppf)Cl$_2$ (5 mg, cat.). The mixture was stirred at 100° C. for 16 h. The solvent was removed in vacuo, and the residue was purified by prep-TLC (PE/EtOAc=5/1) to give the title compound (40 mg, yield: 44%) as a white solid. LCMS (ESI) calc'd for C$_{26}$H$_{19}$F$_5$N$_2$O$_3$ [M+H]$^+$: 503. found: 503.

ii). Preparation of methyl 4-(1-(2-ethyl-6-(trifluoromethyl)benzyl)-4-fluoro-1H-indazol-3-yl)-5-fluoro-2-methoxybenzoate (J-3)

To a solution of methyl 5-fluoro-4-(4-fluoro-1-(2-(trifluoromethyl)-6-vinylbenzyl)-1H-indazol-3-yl)-2-methoxybenzoate (J-2) (40 mg, 0.08 mmol) in EtOAc (3 mL) was added Pd/C (100 mg, wet). The mixture was degassed in vacuo and purged with H$_2$ balloon. The mixture was stirred at 10° C. for 3 h and filtered on celite. The filtrate was concentrated in vacuo, and the residue was purified by prep-TLC (PE/EtOAc=5/1) to give the title compound (30 mg, yield: 75%) as a yellow solid. LCMS (ESI) calc'd for C$_{26}$H$_{21}$F$_5$N$_2$O$_3$ [M+H]$^+$: 505. found: 505.

iii). Preparation of 4-(1-(2-ethyl-6-(trifluoromethyl)benzyl)-4-fluoro-1H-indazol-3-yl)-5-fluoro-2-hydroxybenzoic acid (9A)

To a solution of methyl 4-(1-(2-ethyl-6-(trifluoromethyl)benzyl)-4-fluoro-1H-indazol-3-yl)-5-fluoro-2-methoxybenzoate (J-3) (30 mg, 0.06 mmol) in DCM (2 mL) was added BBr$_3$ (0.12 mL, 1.2 mmol) at −30° C. The mixture was stirred at 10° C. for 16 h. The resulting mixture was concentrated in vacuo. The residue was purified by prep. HPLC (acetonitrile+0.75% trifluoroacetic acid in water) to afford the title compound (5 mg, yield: 17.8%) as a white solid. LCMS (ESI) calc'd for C$_{24}$H$_{17}$F$_5$N$_2$O$_3$ [M+H]': 477. found: 477; $^1$H NMR (400 MHz, CDCl$_3$) δ 7.70 (2H, d, J=7.6 Hz), 7.54-7.62 (2H, m), 7.39 (1H, br s), 7.30 (1H, d, J=8.53 Hz), 6.89 (2H, d, J=15.6 Hz), 5.79-5.86 (2H, m), 2.68 (2H, s), 0.90-0.97 (3H, m).

The following example shown in TABLE 5 was prepared using prop-1-en-2-ylboronic acid instead of vinylboronic acid and following similar procedures described for Example 9A in Scheme J, which can be achieved by those of ordinary skill in the art of organic synthesis in light of the present disclosure.

TABLE 5
| Chemical Name | Structure | LCMS [M + H]+ Found |
|---|---|---|
| 9B 4-(1-(2-chloro-6-fluorobenzyl)-4-fluoro-1H-indazol-3-yl)-5-fluoro-2-hydroxybenzoic acid | 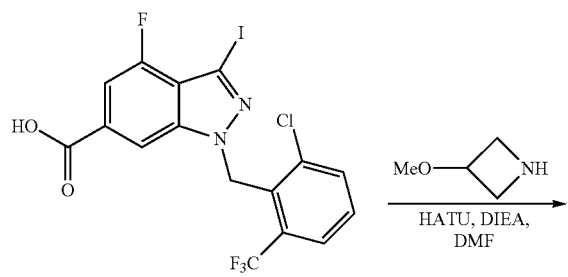 | 491 |
Example 10A
Preparation of sodium 4-(1-(2-chloro-6-(trifluoromethyl)benzyl)-4-fluoro-6-(3-methoxyazetidine-1-carbonyl)-1H-indazol-3-yl)-5-fluoro-2-hydroxybenzoate (10A)
Scheme K
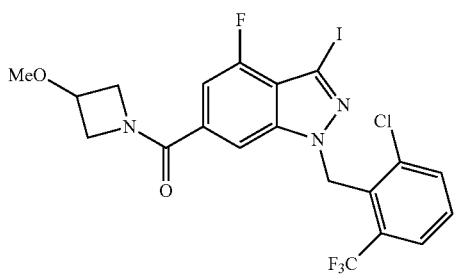
K-1
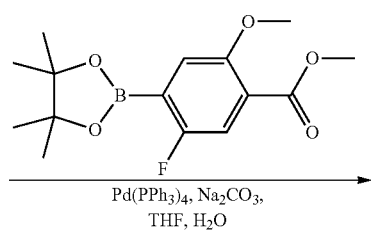
K-2

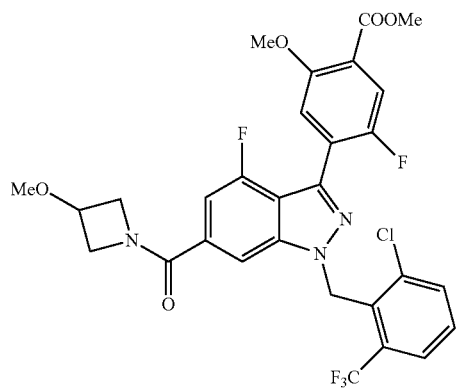

K-3

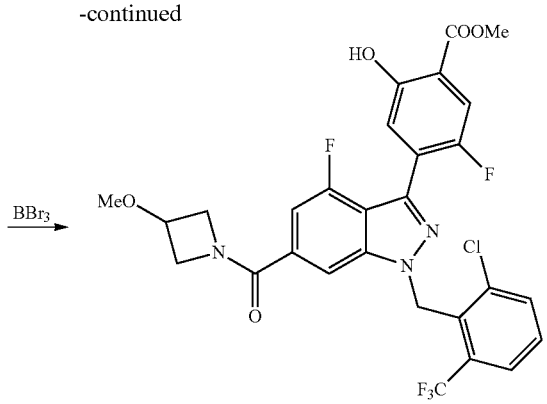

K-4

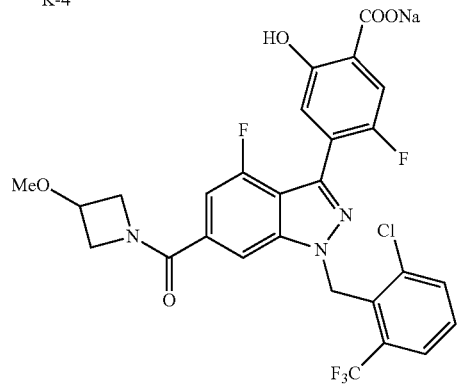

10A i). Preparation of (1-(2-chloro-6-(trifluoromethyl)benzyl)-4-fluoro-3-iodo-1H-indazol-6-yl)(3-methoxyazetidin-1-yl)methanone (K-2)

To a mixture of 1-(2-chloro-6-(trifluoromethyl)benzyl)-4-fluoro-3-iodo-1H-indazole-6-carboxylic acid (K-1) (500 mg, 1 mmol), HATU (456 mg, 1.2 mmol) and 3-methoxyazetidine hydrochloride (246 mg, 2 mmol) in DMF (10 mL) was added DIEA (387 mg, 3 mmol). The mixture was stirred at 40° C. for 3 h, and then poured into $H_2O$ (50 mL). The precipitated solid was collected by filtration, washed with water (20 mL×5) and dried in vacuo to afford the title compound (543 mg, 95.4%) as a yellow solid without further purification. LCMS (ESI) calc'd for $C_{20}H_{15}ClF_4IN_3O_2$ [M+H]$^+$: 568. found: 568.

ii). Preparation of methyl 4-(1-(2-chloro-6-(trifluoromethyl)benzyl)-4-fluoro-6-(3-methoxyazetidine-1-carbonyl)-1H-indazol-3-yl)-5-fluoro-2-methoxybenzoate (K-3)

A mixture of (1-(2-chloro-6-(trifluoromethyl)benzyl)-4-fluoro-3-iodo-1H-indazol-6-yl)(3-methoxyazetidin-1-yl)methanone (K-2) (540 mg, 0.952 mmol), Pd(PPh$_3$)$_4$ (115 mg, 0.1 mmol), Na$_2$CO$_3$ (254 mg, 2.4 mmol) and methyl 5-fluoro-2-methoxy-4-(4,4,5,5-tetramethyl-1,3,2-dioxaborolan-2-yl)benzoate (443 mg, 1.43 mmol) in THF (12 mL) and H$_2$O (3 mL) was stirred at 70° C. under N$_2$ for 16 h. The resulting mixture was diluted with water (30 mL) and extracted with EtOAc (30 mL×2). The combined extracts were washed successively with water (50 mL×2) and brine (80 mL), dried over anhydrous Na$_2$SO$_4$ and concentrated in vacuo. The residue was purified by column chromatography on silica gel (PE/EtOAc=1/1) to give the title compound (360 mg, yield: 60.7%) as a yellow solid. LCMS (ESI) calc'd for $C_{29}H_{23}ClF_5N_3O_5$ [M+H]$^+$: 624. found: 624.

iii). Preparation of methyl 4-(1-(2-chloro-6-(trifluoromethyl)benzyl)-4-fluoro-6-(3-methoxyazetidine-1-carbonyl)-1H-indazol-3-yl)-5-fluoro-2-hydroxybenzoate (K-4)

To a solution of methyl 4-(1-(2-chloro-6-(trifluoromethyl)benzyl)-4-fluoro-6-(3-methoxyazetidine-1-carbonyl)-1H-indazol-3-yl)-5-fluoro-2-methoxybenzoate (K-3) (180 mg, 0.29 mmol) in DCM (3 mL) was added a solution of BBr$_3$ (145 mg, 0.578 mmol) in DCM (2 mL) at 0° C. under N$_2$. The solution was stirred at 0° C. for 30 min, quenched with MeOH (2 mL) and concentrated in vacuo. The residue was diluted with water (20 mL) and extracted with EtOAc (20 mL×3). The combined extracts were washed successively with water (30 mL×3) and brine (50 mL), dried over anhydrous Na$_2$SO$_4$ and concentrated in vacuo to afford crude product of the title compound (180 mg) without further purification. LCMS (ESI) calc'd for $C_{28}H_{21}ClF_5N_3O_5$ [M+H]$^+$: 610. found: 610.

iv). Preparation of sodium 4-(1-(2-chloro-6-(trifluoromethyl)benzyl)-4-fluoro-6-(3-methoxyazetidine-1-carbonyl)-1H-indazol-3-yl)-5-fluoro-2-hydroxybenzoate (10A)

To a solution of methyl 4-(1-(2-chloro-6-(trifluoromethyl)benzyl)-4-fluoro-6-(3-methoxyazetidine-1-carbonyl)-1H- indazol-3-yl)-5-fluoro-2-hydroxybenzoate (K-4) (180 mg, 0.3 mmol) in THF (4 mL) was added a solution of LiOH (42 mg, 1.06 mmol) in H$_2$O (1 mL). The mixture was stirred at room temperature for 16 h, diluted with H$_2$O (10 mL) and washed with EtOAc (30 mL×2). Then the aqueous layer was acidified to pH=4 and extracted with EtOAc (50 mL×2). The combined extracts were washed successively with water (50 mL×2) and brine (80 mL), dried over anhydrous Na$_2$SO$_4$ and concentrated in vacuo. The residue was further purified by prep-HPLC (acetonitrile+0.75%0 trifluoroacetic acid in water) to afford free acid (20 mg, yield: 11.2%) as a white solid. Then to a solution of the free acid (20 mg, 0.034 mmol) in DMSO (2 mL) was added a solution of NaOH (0.5 M, 0.067 mL, 0.034 mmol). Then the mixture was stirred at room temperature for 30 minutes. After the solid was dissolved completely, the solution was filtered and the filtrate was concentrated to dryness with lyophilization to afford the title compound (9.5 mg, yield: 45.2%) as a white solid. For free acid: LCMS (ESI) calc'd for C$_{27}$H$_{10}$ClF$_5$N$_3$O$_5$ [M+H]$^+$: 596. found: 596; $^1$H NMR (400 MHz, DMSO-d$_6$) δ 3.26 (3H, s), 3.91 (1H, d, J=8.03 Hz), 4.25-4.38 (3H, m), 4.56 (1H, br s), 5.93 (2H, s), 6.62 (1H, d, J=6.02 Hz), 7.18 (1H, d, J=11.04 Hz), 7.47 (1H, d, J=10.04 Hz), 7.64-7.72 (1H, m), 7.89 (2H, d, J=8.03 Hz), 8.05 (s, 1H).

The following examples shown in TABLE 6 were prepared following similar procedures described for Example 10A in Scheme K which can be achieved by those of ordinary skill in the art of organic synthesis in light of the present disclosure.

TABLE 6

| | Chemical Name | Structure | LCMS [M + H]$^+$ Found |
|---|---|---|---|
| 10B | 4-(6-(azetidine-1-carbonyl)-1-(2-chloro-6-(trifluoromethyl)-benzyl)-4-fluoro-1H-indazol-3-yl)-5-fluoro-2-hydroxybenzoic acid | 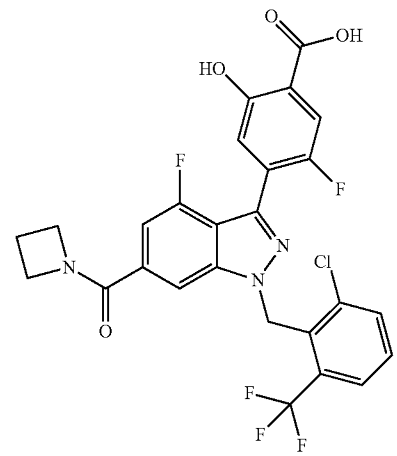 [SMILES: O=C(O)c1cc(F)c(-c2nn(Cc3c(Cl)cccc3C(F)(F)F)c3cc(C(=O)N4CCC4)cc(F)c23)cc1O] | 566 |
| 10C | 4-(6-(azetidine-1-carbonyl)-1-(2-chloro-6-(trifluoromethyl)-benzyl)-4-fluoro-1H-indazol-3-yl)-3-fluorobenzoic acid | 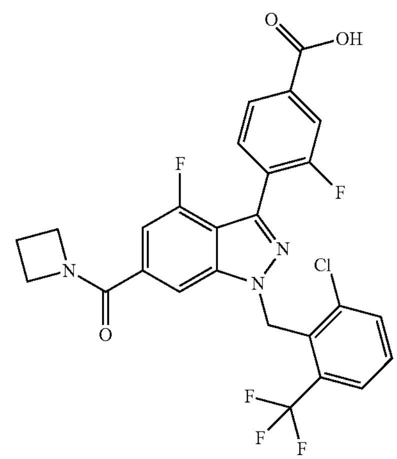 [SMILES: O=C(O)c1ccc(-c2nn(Cc3c(Cl)cccc3C(F)(F)F)c3cc(C(=O)N4CCC4)cc(F)c23)c(F)c1] | 550 |

Biological Assays

The compounds of the invention inhibit RORgammaT activity. Activation of RORgammaT activity can be measured using, e.g., biochemical TR-FRET assay. In such an assay, interaction of cofactor-derived peptides with human RORgammaT-Ligand Binding Domain (LBD) can be measured. The TR-FRET technique is a sensitive biochemical proximity assay that will give information concerning the interaction of a ligand with the LBD, in the presence of cofactor-derived peptides (Zhou et al., Methods 25:54-61, 2001).

To identify novel antagonists of RORgammaT, an assay was developed which employs the interaction of RORgammaT with its co-activator peptide SRC1_2. This peptide mimics the recruitment of co-activators to RORgammaT through its interaction with the LXXLL (SEQ ID NO:1) (e.g., NR box) motifs (Xie et al., J. Immunol. 175: 3800-09, 2005; Kurebayashi et al., Biochem. Biophys. Res. Commun.

315: 919-27, 2004; Jin et al., Mol. Endocrinology 24:923-29, 2010). The RORγ-Ligand Binding Domain TR-FRET Assay was run according to the following protocol.
HIS-tagged RORγ-LBD protein was expressed in SF9 cells using a baculovirus expression system. The RORγ-LBD protein was purified by glutathione sepharose chromatography. Separately, SF9 cells not expressing any recombinant protein were lysed and the lysate was added to the purified RORγ-LBD at 0.25 µl lysate (from 10,000 SF9 cells)/nM purified protein. The mixture was then diluted in assay buffer (50 mM Tris pH 7.0, 50 mM KCl, 1 mM EDTA, 0.1 mM DTT) to obtain RORγ-LBD final concentration of 3 nM in 384-well assay plate.

Compounds to be tested were injected to the assay plate using Acoustic Droplet Ejection technology by Echo 550 liquid handler (Labcyte, CA).
A stock of biotinylated-LXXLL peptide from coactivator SRC1 (Biotin-CPSSHSSLTERHKILHRLLQEGSPS) (SEQ ID NO:2) was prepared in assay buffer and added to each well (100 nM final concentration). A solution of Europium tagged anti-HIS antibody (1.25 nM final concentration) and APC conjugated streptavidin (8 nM final concentration) were also added to each well.

The final assay mixture was incubated overnight at 4° C., and the fluorescence signal was measured on an Envision plate reader: (Excitation filter=340 nm; APC emission=665 nm; Europium emission=615 nm; dichroic mirror=D400/D630; delay time=100 µs, integration time=200 µs). IC50 values for test compounds were calculated from the quotient of the fluorescence signal at 665 nm divided by the fluorescence signal at 615 nm.

Biological Data

The following table tabulates the biological data disclosed for the instant invention.

| Examples | Fret IC$_{50}$ (nM) |
|---|---|
| 1A | 142 |
| 1B | 2293 |
| 1C | 39 |
| 1D | 65 |
| 1E | 219 |
| 1F | 1553 |
| 1G | 725 |
| 1H | 358 |
| 1I | 8228 |
| 1J | >10000 |
| 1K | >10000 |
| 1L | 2122 |
| 1M | 3102 |
| 1N | >10000 |
| 1O | 1188 |
| 1P | >10000 |
| 1Q | 3792 |
| 1R | 4306 |
| 1S | 3708 |
| 1T | 1916 |
| 1U | 9120 |
| 1V | 2170 |
| 1W | 4199 |
| 1X | 3264 |
| 1Y | 599 |
| 1Z | 380 |
| 1AA | 4 |
| 2A | 283 |
| 2B | 33 |
| 3A | 4855 |
| 3B | 7174 |
| 3C | 1375 |
| 3D | 2735 |
| 3E | 959 |
| 3F | 3861 |
| 3G | 89 |
| 3H | 775 |
| 4A | 4 |
| 4B | 72 |
| 4C | 4443 |
| 4D | 497 |
| 4E | 659 |
| 4F | 211 |
| 4G | 345 |
| 4H | 323 |
| 4I | 1338 |
| 4J | 531 |
| 4M | 13 |
| 4K | 3350 |
| 4L | 15 |
| 5A | 30 |
| 6A | 24 |
| 7A | 380 |
| 8A | 15 |
| 8B | 93 |
| 9A | 175 |
| 9B | 17 |
| 10A | 4 |
| 10B | 1 |
| 10C | 3 |

The invention claimed is:

1. A compound according to Formula I

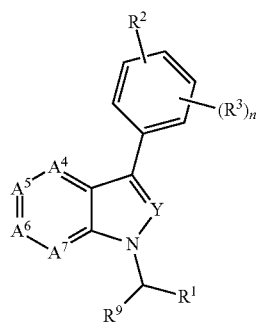

I or a pharmaceutically acceptable salt or solvate thereof, wherein:

Y is CH, N or $CR^a$;
n=0, 1, 2, 3 or 4;
$A^4$ is $CR^4$ or N,
$A^5$ is $CR^5$,
$A^6$ is $CR^6$,
$A^7$ is $CR^7$,
$R^a$ is $(C_{1-4})$alkyl;
$R^1$ is one of the following:
  (a) phenyl substituted with one, two, or three $R^8$;
  (b) phenyl that is (i) substituted with an unsubstituted $(C_{3-5})$heterocycloalkyl, unsubstituted $(C_{3-5})$heteroaryl, or $(C_{3-7})$cycloalkyl optionally substituted with hydroxy, and (ii) optionally substituted with one or two $R^8$;
  (c) pyridinyl, quinolinyl, benzooxadiazolyl, thiophenyl, isoxazolyl, or benzothiophenyl, each optionally substituted with one, two, or three $R^8$; or
  (d) pyridinyl, quinolinyl, benzooxadiazolyl, thiophenyl, isoxazolyl, or benzothiophenyl, that is (i) substituted with an unsubstituted $(C_{3-5})$heterocycloalkyl, unsubstituted $(C_{3-5})$heteroaryl, or $(C_{3-7})$cycloalkyl optionally substituted with hydroxy, and (ii) optionally substituted with one or two $R^8$;
$R^2$ is hydroxycarbonyl, hydroxycarbonyl$(C_{1-10})$alkyl, $(C_{1-10})$alkylsulfoxyaminocarbonyl, or carbamoyl;
$R^3$ is hydrogen, halogen, cyano, nitro, hydroxy, (C1-3)alkylC(O)O—, $(C_{1-4})$alkyl, or $(C_{1-4})$alkoxy, wherein $(C_{1-4})$alkyl and $(C_{1-4})$alkoxy are optionally substituted with one or more halogen;

$R^4$, $R^5$, $R^6$ and $R^7$ independently are H, halogen, amino, cyano, $(C_{1-4})$alkyl, $(C_{0-10})$alkyl)aminocarbonyl, or (di)$(C_{1-6})$alkylaminocarbonyl, wherein $(C_{1-3})$alkoxy and $(C_{1-4})$-alkyl are optionally substituted with one or more halogen, hydroxyl or $(C_{1-3})$alkoxy; or a group having the formula

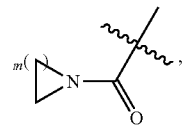

optionally substituted with one or more of the following: $(C_{1-10})$alkyl, halogen, hydroxy, and $(C_{1-3})$alkoxy, wherein m is 1, 2, 3, or 4;
$R^8$ is halogen, cyano, hydroxy, $(C_{1-3})$alkoxycarbonyl, $(C_{1-4})$alkyl, or $(C_{1-3})$alkoxy, wherein $(C_{1-3})$alkoxycarbonyl, $(C_{1-4})$alkyl, and $(C_{1-3})$alkoxy are optionally substituted with hydroxy or one, two or three halogens; and
$R^9$ is hydrogen or $(C_{1-4})$alkyl.

2. The compound of claim 1 having Formula Ia

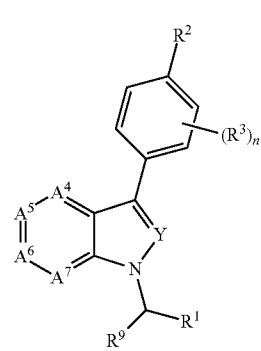

Ia or a pharmaceutically acceptable salt or solvate thereof.

3. The compound of claim 1 having Formula Ib

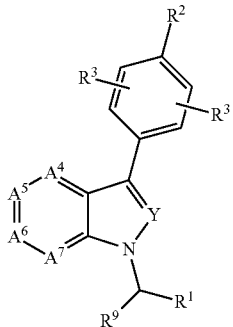

or a pharmaceutically acceptable salt or solvate thereof.

4. The compound of claim 3, wherein Y is N.

5. The compound of claim 3 having Formula Ic

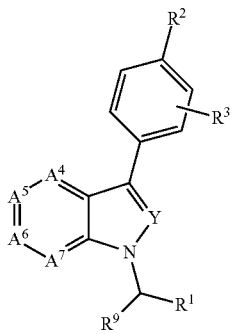

or a pharmaceutically acceptable salt or solvate thereof.

6. The compound of claim 5 having Formula Id

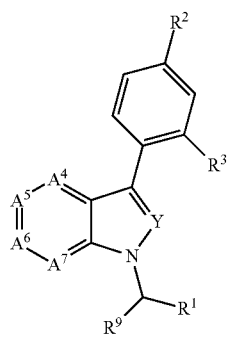

or a pharmaceutically acceptable salt or solvate thereof.

7. The compound of claim 6, wherein Y is N.

8. The compound of claim 2 having Formula Ie

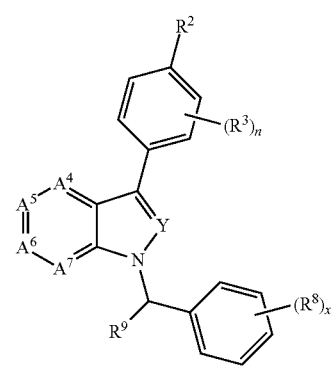

wherein x is 1, 2, or 3, or a pharmaceutically acceptable salt or solvate thereof.

9. The compound of claim 8 having Formula If

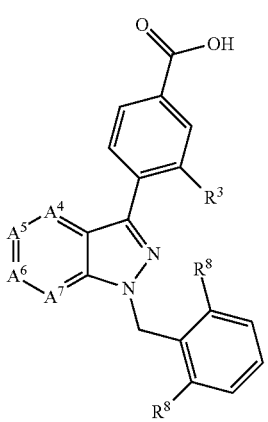

or a pharmaceutically acceptable salt or solvate thereof.

10. The compound of claim 9 having Formula Ig or a pharmaceutically acceptable salt or solvate thereof.

11. The compound of claim 10 having Formula Ih

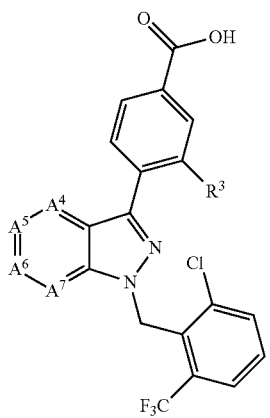

or a pharmaceutically acceptable salt or solvate thereof.

12. The compound of claim 1, wherein $R^1$ is phenyl substituted with one or two $R^8$.

13. The compound of claim 1, wherein $R^1$ is phenyl substituted with one, two or three $R^8$.

14. The compound of claim 13, wherein $R^2$ is C(O)OH.

15. A compound selected from:

4-{1-[2-chloro-6-(trifluoromethyl)benzyl]-1H-pyrazolo[3,4-c]pyridin-3-yl}-3-fluorobenzoic acid;

4-[1-(2-bromo-6-fluorobenzyl)-1H-pyrazolo[4,3-b]pyridin-3-yl]-3-fluorobenzoic acid;

4-{-1-[2-chloro-6-(trifluoromethyl)benzyl]-4-fluoro-1H-indazol-3-yl}-3-fluorobenzoic acid;

4-{-1-[2-chloro-6-(trifluoromethyl)benzyl]-4-fluoro-1H-indazol-3-yl}benzoic acid;

4-{-1-[2-chloro-6-(trifluoromethyl)benzyl]-4-fluoro-1H-indazol-3-yl}-2,5-difluorobenzoic acid;

4-(1-{1-[2-chloro-6-(trifluoromethyl)phenyl]ethyl}-4-fluoro-1H-indazol-3-yl)-3-fluorobenzoic acid;

4-(1-{(1R or 1S)-1-[2-chloro-6-(trifluoromethyl)phenyl]ethyl}-4-fluoro-1H-indazol-3-yl)-3-fluorobenzoic acid;

4-(1-{(1S or 1R)-1-[2-chloro-6-(trifluoromethyl)phenyl]ethyl}-4-fluoro-1H-indazol-3-yl)-3-fluorobenzoic acid;

4-[1-(2-bromo-3-fluorobenzyl)-1H-pyrazolo[4,3-b]pyridin-3-yl]-3-fluorobenzoic acid;

4-[1-(5-chloro-2-cyanobenzyl)-1H-pyrazolo[4,3-b]pyridin-3-yl]-3-fluorobenzoic acid;

3-fluoro-4-(1-{-1-[2-(trifluoromethyl)phenyl]ethyl}-1H-pyrazolo[4,3-b]pyridin-3-yl)benzoic acid;

4-[1-(6-chloro-2-fluoro-3-methylbenzyl)-1H-pyrazolo[4,3-b]pyridin-3-yl]-3-fluorobenzoic acid;

4-[1-(2-chloro-3,6-difluorobenzyl)-1H-pyrazolo[4,3-b]pyridin-3-yl]-3-fluorobenzoic acid;

3-fluoro-4-[1-(2,3,6-trifluorobenzyl)-1H-pyrazolo[4,3-b]pyridin-3-yl]benzoic acid;

3-fluoro-4-{1-[2-fluoro-6-(trifluoromethyl)benzyl]-1H-pyrazolo[4,3-b]pyridin-3-yl}benzoic acid;

4-[1-(2,6-difluorobenzyl)-1H-pyrazolo[4,3-b]pyridin-3-yl]-3-fluorobenzoic acid;

4-[1-(2-chloro-6-fluorobenzyl)-1H-pyrazolo[4,3-b]pyridin-3-yl]-3-fluorobenzoic acid;

4-[1-(6-chloro-2-fluoro-3-methoxybenzyl)-1H-pyrazolo[4,3-b]pyridin-3-yl]-3-fluorobenzoic acid;

4-[1-(2-chloro-6-fluoro-3-methoxybenzyl)-1H-pyrazolo[4,3-b]pyridin-3-yl]-3-fluorobenzoic acid;

4-[1-(2,3-dichloro-6-fluorobenzyl)-1H-pyrazolo[4,3-b]pyridin-3-yl]-3-fluorobenzoic acid;

4-[1-(1-benzothiophen-7-ylmethyl)-1H-pyrazolo[4,3-b]pyridin-3-yl]-3-fluorobenzoic acid;

4-{1-[2,6-dichloro-3-(trifluoromethyl)benzyl]-1H-pyrazolo[4,3-b]pyridin-3-yl}-3-fluorobenzoic acid;

4-[1-(3,6-dichloro-2-fluorobenzyl)-1H-pyrazolo[4,3-b]pyridin-3-yl]-3-fluorobenzoic acid;

4-{1-[2-chloro-6-(methoxycarbonyl)benzyl]-1H-pyrazolo[4,3-b]pyridin-3-yl}-3-fluorobenzoic acid;

4-[1-(2-bromo-6-chlorobenzyl)-1H-pyrazolo[4,3-b]pyridin-3-yl]-3-fluorobenzoic acid;

4-{1-[2-chloro-6-(trifluoromethyl)benzyl]-1H-pyrazolo[4,3-b]pyridin-3-yl}-3-fluorobenzoic acid;

4-{1-[2-chloro-6-(trifluoromethyl)benzyl]-1H-pyrrolo[3,2-b]pyridin-3-yl}-3-fluorobenzoic acid;

4-{1-[2-chloro-6-(trifluoromethyl)benzyl]-1H-pyrrolo[2,3-c]pyridin-3-yl}-3-fluorobenzoic acid;

4-(1-(2-chloro-6-(trifluoromethyl)benzyl)-1H-indazol-3-yl)-2-hydroxybenzoic acid;

3-Fluoro-4-[4-fluoro-1-(2-fluoro-6-methoxybenzyl)-1H-indazol-3-yl]benzoic acid;

3-fluoro-4-(4-fluoro-1-(3-(trifluoromethoxy)benzyl)-1H-indazol-3-yl)benzoic acid;

3-fluoro-4-[4-fluoro-1-(2-methoxybenzyl)-1H-indazol-3-yl]benzoic acid;

3-fluoro-4-{4-fluoro-1-[2-(1H-pyrazol-1-yl)benzyl]-1H-indazol-3-yl}benzoic acid;

4-[1-(2-cyanobenzyl)-4-fluoro-1H-indazol-3-yl]-3-fluorobenzoic acid;

3-fluoro-4-{4-fluoro-1-[2-fluoro-5-(trifluoromethoxy)benzyl]-1H-indazol-3-yl}benzoic acid;

4-[1-(2,6-dichlorobenzyl)-4-fluoro-1H-indazol-3-yl]-3-fluorobenzoic acid;

4-(1-(2,6-dichlorobenzyl)-1H-pyrazolo[4,3-b]pyridin-3-yl)-3-fluorobenzoic acid;

4-(1-(2-bromo-6-(trifluoromethyl)benzyl)-4-fluoro-1H-indazol-3-yl)-5-fluoro-2-hydroxybenzoic acid;

4-(1-(2-chloro-6-fluorobenzyl)-4-fluoro-1H-indazol-3-yl)-5-fluoro-2-hydroxybenzoic acid;

4-(1-benzyl-4-fluoro-1H-indazol-3-yl)-5-fluoro-2-hydroxybenzoic acid;

4-(1-(2-chloro-5-fluorobenzyl)-4-fluoro-1H-indazol-3-yl)-5-fluoro-2-hydroxybenzoic acid;

4-(1-(2-chloro-4-fluorobenzyl)-4-fluoro-1H-indazol-3-yl)-5-fluoro-2-hydroxybenzoic acid;

4-(1-(2-bromo-5-fluorobenzyl)-4-fluoro-1H-indazol-3-yl)-5-fluoro-2-hydroxybenzoic acid;

4-(1-(3-chloro-5-fluorobenzyl)-4-fluoro-1H-indazol-3-yl)-5-fluoro-2-hydroxybenzoic acid;

4-(1-(3, 5-dichlorobenzyl)-4-fluoro-1H-indazol-3-yl)-5-fluoro-2-hydroxybenzoic acid;

4-(1-(4-bromo-2-fluorobenzyl)-4-fluoro-1H-indazol-3-yl)-5-fluoro-2-hydroxybenzoic acid;

4-(1-(2,5-dichlorobenzyl)-4-fluoro-1H-indazol-3-yl)-5-fluoro-2-hydroxybenzoic acid;

5-fluoro-4-(4-fluoro-1-(3-fluoro-5-(trifluoromethyl)benzyl)-1H-indazol-3-yl)-2-hydroxybenzoic acid;

5-fluoro-4-(4-fluoro-1-(2-fluoro-6-(trifluoromethyl)benzyl)-1H-indazol-3-yl)-2-hydroxybenzoic acid;

4-(1-(2-chloro-6-cyclopropylbenzyl)-4-fluoro-1H-indazol-3-yl)-5-fluoro-2-hydroxybenzoic acid;

4-(1-(2-chloro-6-methylbenzyl)-4-fluoro-1H-indazol-3-yl)-5-fluoro-2-hydroxybenzoic acid;

4-(1-(2-chloro-6-(1-hydroxycyclobutyl)benzyl)-4-fluoro-1H-indazol-3-yl)-3-fluorobenzoic acid;

5-fluoro-4-(4-fluoro-1-(2-methyl-6-(trifluoromethyl)benzyl)-1H-indazol-3-yl)-2-hydroxybenzoic acid;

5-fluoro-4-(4-fluoro-1-(2-(trifluoromethyl)benzyl)-1H-indazol-3-yl)-2-hydroxybenzoic acid;

4-(1-(2-ethyl-6-(trifluoromethyl)benzyl)-4-fluoro-1H-indazol-3-yl)-5-fluoro-2-hydroxybenzoic acid;

4-(1-(2-chloro-6-fluorobenzyl)-4-fluoro-1H-indazol-3-yl)-5-fluoro-2-hydroxybenzoic acid;

sodium 4-(1-(2-chloro-6-(trifluoromethyl)benzyl)-4-fluoro-6-(3-methoxyazetidine-1-carbonyl)-1H-indazol-3-yl)-5-fluoro-2-hydroxybenzoate;

4-(6-(azetidine-1-carbonyl)-1-(2-chloro-6-(trifluoromethyl)benzyl)-4-fluoro-1H-indazol-3-yl)-5-fluoro-2-hydroxybenzoic acid; and 4-(6-(azetidine-1-carbonyl)-1-(2-chloro-6-(trifluoromethyl)benzyl)-4-fluoro-1H-indazol-3-yl)-3-fluorobenzoic acid.

16. A pharmaceutical composition comprising a compound of claim 1 or a pharmaceutically acceptable salt or solvate thereof, and one or more pharmaceutically acceptable excipients.

17. The pharmaceutical composition of claim 16, further comprising at least one additional therapeutically active agent.

18. A method for treating a disease or condition mediated by RORgammaT in a subject comprising administering to the subject an amount of a compound of claim 1, or a pharmaceutically acceptable salt or solvate thereof, that is effective for treating the disease or condition mediated by RORgammaT in the subject, wherein the disease or condition is an autoimmune disease and wherein the compound of claim 1 is effective for treating an autoimmune disease in that subject.

19. A method for treating a disease or condition mediated by RORgammaT in a subject comprising administering to the subject an amount of a compound of claim 1, or a pharmaceutically acceptable salt or solvate thereof, that is effective for treating the disease or condition mediated by RORgammaT in the subject, wherein the disease or condition is multiple sclerosis, inflammatory bowel disease, Crohn's disease, ankylosing spondylitis, psoriasis, rheumatoid arthritis, asthma, osteoarthritis, Kawasaki disease, Hashimoto's thyroiditis or mucosal leishmaniasis.

20. The compound of claim 1, wherein the compound is

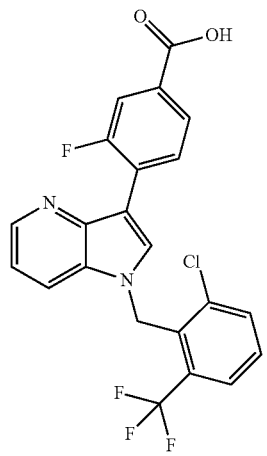 [SMILES: O=C(O)c1ccc(-c2cn(Cc3c(Cl)cccc3C(F)(F)F)c3cccnc23)c(F)c1]

or a pharmaceutically acceptable salt thereof.

21. A pharmaceutical composition comprising a compound of claim 20 and one or more pharmaceutically acceptable excipients.

22. The compound of claim 1, wherein the compound is

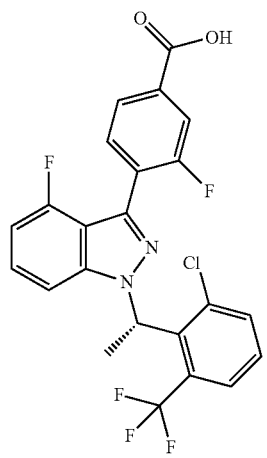 [SMILES: C[C@@H](c1c(Cl)cccc1C(F)(F)F)n1nc(-c2ccc(C(=O)O)cc2F)c2c(F)cccc21]

or a pharmaceutically acceptable salt thereof.

23. A pharmaceutical composition comprising a compound of claim 22 and one or more pharmaceutically acceptable excipients.

* * * * *